US008921522B2

(12) United States Patent
Grosveld et al.

(10) Patent No.: US 8,921,522 B2
(45) Date of Patent: *Dec. 30, 2014

(54) BINDING MOLECULES

(75) Inventors: Franklin Gerardus Grosveld, Rotterdam (NL); Richard Willhelm Janssens, Rotterdam (NL); Dubravka Drabek, Rotterdam (NL); Roger Kingdon Craig, Sandbach (GB)

(73) Assignee: Erasmus University Medical Centre, Rotterdam (NL)

( * ) Notice: Subject to any disclaimer, the term of this patent is extended or adjusted under 35 U.S.C. 154(b) by 518 days.

This patent is subject to a terminal disclaimer.

(21) Appl. No.: 12/645,653

(22) Filed: Dec. 23, 2009

(65) Prior Publication Data

US 2010/0216974 A1    Aug. 26, 2010

Related U.S. Application Data

(63) Continuation of application No. 11/658,361, filed as application No. PCT/GB2005/002892 on Jul. 22, 2005, now abandoned.

(30) Foreign Application Priority Data

Jul. 22, 2004  (GB) .................................. 0416392.9
Jun. 10, 2005  (GB) .................................. 0511881.5

(51) Int. Cl.
| *C07K 16/00* | (2006.01) |
| *C12P 21/00* | (2006.01) |
| *C12N 15/63* | (2006.01) |
| *C07K 16/24* | (2006.01) |
| *C07K 16/10* | (2006.01) |
| *C07K 16/12* | (2006.01) |

(52) U.S. Cl.
CPC .............. *C07K 16/241* (2013.01); *C07K 16/00* (2013.01); *C07K 16/1054* (2013.01); *C07K 16/1063* (2013.01); *C07K 16/1232* (2013.01); *C07K 2317/22* (2013.01); *C07K 2317/31* (2013.01); *C07K 2317/53* (2013.01); *C07K 2317/569* (2013.01); *C07K 2319/00* (2013.01)
USPC .................................... 530/387.1; 530/391.1

(58) Field of Classification Search
USPC .......................................... 530/387.1, 391.1
See application file for complete search history.

(56) References Cited

U.S. PATENT DOCUMENTS

| 5,487,890 | A | 1/1996 | Taylor et al. | |
| 2003/0058074 | A1 | 3/2003 | Valle et al. | |
| 2009/0271880 | A1* | 10/2009 | Grosveld et al. | 800/6 |
| 2009/0307787 | A1* | 12/2009 | Grosveld et al. | 800/6 |
| 2010/0197897 | A1* | 8/2010 | Grosveld et al. | 530/387.3 |

FOREIGN PATENT DOCUMENTS

| EP | 0143151 A2 | 6/1985 |
| EP | 0368684 B2 | 3/1994 |
| EP | 0463151 B1 | 6/1996 |
| EP | 0436597 B1 | 4/1997 |
| EP | 0623679 B1 | 6/2003 |
| RU | 2335507 C2 | 10/2008 |
| WO | WO94/04678 | 3/1994 |
| WO | WO02/12437 A2 | 2/2002 |
| WO | WO02/085944 A2 | 10/2002 |
| WO | WO 02/085945 * | 10/2002 |
| WO | WO02/085945 A2 | 10/2002 |
| WO | WO 02/100348 | 12/2002 |
| WO | WO03/000737 A3 | 1/2003 |
| WO | WO03/002609 A2 | 1/2003 |
| WO | WO2004/003019 A2 | 1/2004 |
| WO | WO 2004/003019 * | 6/2004 |
| WO | WO2004/049794 A2 | 6/2004 |
| WO | WO2004/058820 A2 | 7/2004 |
| WO | WO2011/072204 A1 | 6/2011 |

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Biburger, M., et al., "A Novel Bispecific Tetravalent Antibody Fusion Protein to Target Costimulatory Activity for T-cell Activation to Tumor Cells Overexpressing ErbB2/HER2", J. Mol. Biol., vol. 346, pp. 1299-1311, 2005.
Boder, E.T., et al., "Yeast surface display for screening combinatorial polypeptide libraries", Nat. Biotechnol., vol. 15, No. 6, pp. 553-557, 1997.
Bond, C.J., et al., "Contributions of CDR3 to $V_hH$ Domain Stability and the Design of Monobody Scaffolds for Naive Antibody Libraries", J. Mol. Biol, vol. 332, pp. 643-655, 2003.

(Continued)

*Primary Examiner* — Lynn Bristol
(74) *Attorney, Agent, or Firm* — Saul Ewing LLP; Doreen Y. Trujillo

(57) ABSTRACT

The present invention relates to the manufacture of a diverse repertoire of functional heavy chain-only antibodies that undergo affinity maturation, and uses thereof. The invention also relates to the manufacture and use of a diverse repertoire of class-specific heavy chain-only antibodies and to the manufacture and use of multivalent polypeptide complexes with antibody heavy chain functionality, preferably antibody heavy chain binding functionality, constant region effector activity and, optionally, additional effector functions.
The present invention also relates to a method of generation of fully functional heavy chain-only antibodies in transgenic mice in response to antigen challenge. In particular, the present invention relates to a method for the generation of human antigen-specific, high affinity, heavy chain-only antibodies of any class, or mixture of classes and the isolation and expression of fully functional VH antigen-binding domains.

5 Claims, 26 Drawing Sheets

(56) References Cited

OTHER PUBLICATIONS

Brandt, C.R., et al., Loss of a Consensus Splice Signal in a Mutant Immunoglobulin Gene Eliminates the $CH_1$ Domain Exon from the mRNA, Molecular and Cellular Biology, vol. 4, No. 7, pp. 1270-1277, 1984.
Brophy, B., et al., "Cloned transgenic cattle produce milk with higher levels of β-casein and κ-casein", Nature Biotechnology, vol. 21, pp. 157-162, 2003.
Brüggemann, M., et al., "A repertoire of monoclonal antibodies with human heavy chains from transgenic mice", Proc. Natl. Acad. Sci. USA, vol. 86, pp. 6709-6713, 1989.
Brüggemann, M., et al., "Strategies for expressing human antibody repertoires in transgenic mice", Immunology Today, vol. 17, No. 8, pp. 391-397, 1996.
Carter, B., et al., "Bispecific human IgG by design," Journal of Immunological Methods, vol. 248, Nos. 1-2, pp. 7-15, 2001.
Damak, S., et al., "Improved Wool Production in Transgenic Sheep Expressing Insulin-like Growth Factor 1", Bio/technology, vol. 14, pp. 185-188, 1996.
Davies, J., et al., "'Camelising' human antibody fragments: NMR studies on VH domains", FEBS Letters, vol. 339, pp. 285-290, 1994.
Davies, J., et al., "Single antibody domains as small recognition units: design and in vitro antigen selection of camelized human VH domains with improved protein stability", Protein Engineering, vol. 9, No. 6, pp. 531-537, 1996.
De Genst, E., et al., "Strong in Vivo Maturation Compensates for Structurally Restricted H3 Loops in Antibody Repertoires", J. Biol. Chem., vol. 280, No. 14, pp. 14114-14121, 2005.
Dekker, S., et al., "Intracellularly Expressed Single-Domain Antibody against p15 Matrix Protein Prevents the Production of Porcine Retroviruses", J Virol., vol. 77, No. 22, pp. 12132-12139, 2003.
Desmyter, A., et al., "Crystal structure of a camel single-domain $V_H$ antibody fragment in complex with lysozyme", Nature Structural Biology, vol. 3, No. 9, pp. 803-811, 1996.
Echelard, Y., "Year of the ox", Nature Biotechnology, vol. 27, No. 2, pp. 146-147, 2009.
Ferguson, P.J., et al., "Antigen-Based Heteropolymers", Arthritis and Rheumatism, vol. 38, pp. 190-200, 1995.
Glennie, M.J., et al., "Renaissance of cancer therapeutic antibodies", Drug Discovery Today, vol. 8, pp. 503-510, 2003.
Hamers-Casterman, C., et al., "Naturally occurring antibodies devoid of light chains", Nature. 363, pp. 446-448, 1993.
Hammer, R.E., et al., "Spontaneous Inflammatory Disease in Transgenic Rats Expressing HLA-B27 and Human $β_2$m: an Animal Model of HLA-B27-Associated Human Disorders", Cell, vol. 63, pp. 1099-1112, 1990.
Harmsen, M.M., et al., "Llama heavy-chain V regions consist of at least four distinct subfamilies revealing novel sequence features", Molecular Immunology, vol. 37, pp. 579-590, 2000.
Hendershot, L., et al., Assembly and secretion of heavy chains that do not associate post-translationally with immunoglobulin heavy chain-binding protein, J. Cell Biol., vol. 104, pp. 761-767, 1987.
Holliger, P., et al., "Diabodies': Small bivalent and bispecific antibody fragments", Proc. Natl. Acad. Sci. USA, vol. 90, pp. 6444-6448, Jul. 1993.
Hudson, P.J., "Recombinant antibody constructs in cancer therapy", Curr. Opin. Immunol., vol. 11, pp. 548-557, 1999.
Imam, A.M.A., et al., "Modification of human β-globin locus PAC clones by homologous recombination in *Escherichia coli*", Nucleic Acids Research, vol. 18, No. 12, pp. e65 i-e65 vi, 2000.
Janssens, R., et al., "Generation of heavy-chain-only antibodies in mice", PNAS, vol. 103, No. 41, pp. 15130-15135, 2006.
Jaton, J., et al., "Recovery of Antibody Activity upon Reoxidation of Completely Reduced Polyalanyl Heavy Chain and Its Fd Fragment Derived from Anti-2,4-dinitrophenyl Antibody", Biochemistry, vol. 7, No. 12, pp. 4185-4195, Dec. 1968.
Kellermann, S., et al., "Antibody discovery: the use of transgenic mice to generate human monoclonal antibodies for therapeutics", Current Opinion in Biotechnology, vol. 13, pp. 593-597, 2002.
Kitamura, D., et al., "A B cell-deficient mouse by targeted disruption of the membrane exon of the immunoglobulin .mu. chain gene," Nature vol. 350, pp. 423-426, 1991.
Kokubu, F., et al., "Diverse organization of immunoglobulin VH gene loci in a primitive vertebrate", EMBO. J., vol. 7, pp. 3413-3422, 1988.
Kuroiwa, Y., et al., "Cloned transchromosomic calves producing human immunoglobulin", Nature Biotechnology, vol. 20, No. 9, pp. 889-894, 2002.
Leenan, P.J., et al., "Heterogeneity of Mouse Spleen Dendritic Cells: In Vivo Phagocytic Activity, Expression of Macrophage Markers, and Subpopulation Turnover", The Journal of Immunology, vol. 160, pp. 2166-2173, 1998.
Lefranc, M., et al., "IMGT, the international ImMunoGeneTics database", Nucleic Acids Research, vol. 27, No. 1, pp. 209-212, 1999.
Leher, H., et al., "Monoclonal IgA antibodies protect against Acanthamoeba keratitis", Exp. Eye. Res., vol. 69, No. 1, pp. 75-84, 1999.
Lonberg, N., "Human antibodies from transgenic animals", Nature Biotechnology, vol. 23, No. 9, pp. 1117-1125, 2005.
Lu, D., et al., "Di-Diabody: A Novel Tetravalent Bispecific Antibody Molecule by Design", J. Immunol. Methods, vol. 279, Nos. 1-2, pp. 219-232, 2003.
Lyden, D., et al., "Impaired recruitment of bone-marrow-derived endothelial and hematopoietic precursor cells blocks tumor angiogenesis and growth", Nat. Med., vol. 7, No. 11, pp. 1194-1201, 2001.
Marian, A.J., et al., "A transgenic rabbit model for human hypertrophic cardiomyopathy", The Journal of Clinical Investigation, vol. 104, No. 12, pp. 1683-1692, 1999.
Mills, F.C., et al., "Enhancer Complexes Located Downstream of Both Human Immunoglobulin Ca Genes", The Journal of Experimental Medicine, vol. 186, No. 6, pp. 845-858, 1997.
Muller, K.M., et al., "The first constant domain (C(H)1 and C(L)) of an antibody used as heterodimerization domain for bispecific miniantibodies", FEBS Letters, vol. 422, Issue 2, pp. 259-264, 1998.
Mullins, J.J., et al., "Fulminant hypertension in transgenic rats harbouring the mouse Ren-2 gene", Letters to Nature, vol. 344, pp. 541-544, 1990.
Muyldermans, S., et al., "Sequence and structure of $V_H$ domain from naturally occurring camel heavy chain immunoglobulins lacking light chains", Protein Engineering, vol. 7, No. 9, pp. 1129-1135, 1994.
Muyldermans, S., "Single domain camel antibodies: current status", Molecular Biotechnology, vol. 74, pp. 277-302, 2001.
Nicholson, I.C., et al., "Antibody Repertoires of Four- and Five-Feature Translocus Mice Carrying Human Immunoglobulin Heavy Chain and {kappa} and {lambda} Light Chain Yeast Artificial Chromosomes", The Journal of Immunology 163 (12), pp. 6898-6906 (Dec. 15, 1999), The William and Wilkins Co, Baltimore, MD.
O'Donnell, J.K., et al., "Production of human hemoglobin in transgenic swine: an approach to a blood substitute", vol. 17, No. 2, pp. 307-312, 1993.
O'Neill, T.P., "HLA-B27 transgenic rats: animal model of human HLA-B27-associated disorders", Toxicologic Pathology, vol. 25, No. 4, pp. 407-408, 1997.
Riechmann L., et al., "Single domain antibodies: comparison of camel VH and camelised human VH domains", Journal of Immunological Methods, vol. 231, pp. 25-38, 1999.
Segal, D.M., et al., "Introduction: Bispecific Antibodies", J. Immunol. Methods, vol. 248, pp. 1-6, 2001.
Sitia, R., et al., "Developmental regulation of IgM secretion: The role of the carboxy-terminal cysteine", Cell, vol. 60, No. 5, pp. 781-790, 1990.
Stanfield, R.L., et al., "Crystal Structure of a Shark Single-Domain Antibody V Region in Complex with Lysozyme", vol. 305, No. 5691, pp. 1770-1773, 2004.
Sung, C., et al., "Yeast surface display for screening combinatorial polypeptide libraries", J. Interferon Cytokine Res., vol. 23, No. 1, pp. 25-36, 2003.
Suresh, M.R., et al., "Advantages of bispecific hybridomas in one-step immunocytochemistry and immunoassays", PNAS, vol. 83, No. 20, pp. 7989-7993, 1986.

(56) References Cited

OTHER PUBLICATIONS

Tacken, P.J., et al., "Effective Targeting of Pathogens to Neutrophils via Chimeric Surfactant Protein D/Anti-CD89 Protein", The Journal of Immunology, vol. 172, No. 8, pp. 4934-4940, Apr. 15, 2004.
Tanha, J., et al., "Optimal Design Features of Camelized Human Single-domain Antibody Libraries", The Journal of Biological Chemistry, vol. 276, No. 27, pp. 24774-24780, Jul. 6, 2001.
Tanha, J., et al., "Selection by phage display of llama conventional $V_H$ fragments with heavy chain antibody $V_HH$ properties", Journal of Immunological Methods, vol. 263, pp. 97-109, 2002.
To, R., et al., "Isolation of Monomeric Human $V_HS$ by a Phage Selection", The Journal of Biological Chemistry, vol. 280, No. 50, pp. 41395-41403, 2005.
Van Dijk, M.A., "Human antibodies as next generation therapeutics", Curr. Opin. Chem. Biol., vol. 5, No. 4, pp. 368-374, 2001.
Van Spriel, A.B., Et Al., "Effective Phagocytosis and Killing of *Candida albicans* via Targeting FcγRI (CD64) or FcαRI (CD89) on Neutrophils", Journal of Infectious Diseases, vol. 179, No. 3, pp. 661-669, 1999.
Van Spriel A.B., et al., "Immunotherapeutic perspective for bispecific antibodies", Immunology Today, vol. 21, No. 8, pp. 391-397, 2000.
Vranken, W., et al., "Solution structure of a llama single-domain antibody with hydrophobic residues typical of the VH/VL interface", Biochemistry, Vol, 41, pp. 8570-8579, 2002.
Wang, B., et al., "Transgenic goats produced by DNA pronuclear microinjection of in vitro derived zygotes", Molecular Reproduction and Development, vol. 63, pp. 437-443, 2002.
Ward, E.S., et al., "Binding activities of a repertoire of single immunoglobulin variable domains secreted from *Escherichia coli*", Nature, vol. 341, pp. 544-546, 1989.
Wright, G., et al., "High level expression of active human alpha-1-antitrypsin in the milk of transgenic sheep", Bio/technology, vol. 9, pp. 830-834, 1991.
Xu, J.L., et al., "Diversity in the CDR3 Region of VH Is Sufficient for Most Antibody Specificities", Immunity, vol. 13, pp. 37-45, 2000.

Yau, K.Y.F., et al., "Affinity maturation of a V(H)H by mutational hotspot randomization", J. Imunol. Methods, vol. 297, Nos. 1-2, pp. 213-224, 2005.
International Search Report based on PCT/GB2005/002892 mailed Apr. 7, 2006.
Holt, L.J. et al., "Domain Antibodies: Proteins for Therapy," Trends in Biotechnology, vol. 21, No. 11, pp. 484-490, 2003.
Worn, A. and Pluckthun, A., "Different equilibrium stability behavior of ScFv fragments: identification, classification, and improvement by protein engineering," Biochemistry, vol. 38, No. 27, pp. 8739-8750, 1999.
Co-pending U.S. Appl. No. 12/645,684, filed Dec. 23, 2009.
Co-pending U.S. Appl. No. 13/013,156, filed Jan. 25, 2011.
Co-pending U.S. Appl. No. 13/837,520, filed Mar. 15, 2013.
Co-pending U.S. Appl. No. 13/837,402, filed Mar. 15, 2013.
EP Communication dated Feb. 27, 2014 regarding European Patent Application No. 10179784.3.
"Shin-Seikagaku Jikken Kouza 12, Bunshi-Men'ekigaku III -Kougen, Koutai, Hotai-" (New Biochemical Experimental Seminar 12, Molecular Immnology III -antigen, antibody, and complement-) 1992, K.K. Tokyo Kagaku Dojin, pp. 1-11, English Translation Excerpts.
Japanese Patent Office Inquiry dispatched on Mar. 11, 2014. English translation.
Pharma Focus Asia, "VelocImmune—A novel platform," 2009, retrieved from the Internet, URL: http://www.pharmafocusasia.com/clinical_trials/human_antibody_discovery.htm, retrieved on Jul. 30, 2014.
Inquiry by Japanese Patent Office dated Jun. 24, 2014, regarding Russian Patent Application No. 2011/166561, filed on Jul. 29, 2011.
Kriangkum, J. et al., "Bispecific and bifunctional single chain recombinant antibodies," Biomolecular Engineering, vol. 18, pp. 31-40 (2001).
Decision of Grant by Russian Patent Office dated May 21, 2014, regarding Russian Patent Application No. 2011/142759, filed on Mar. 19, 2010.

\* cited by examiner

Bivalent secretory IgA

Multivalent IgM like

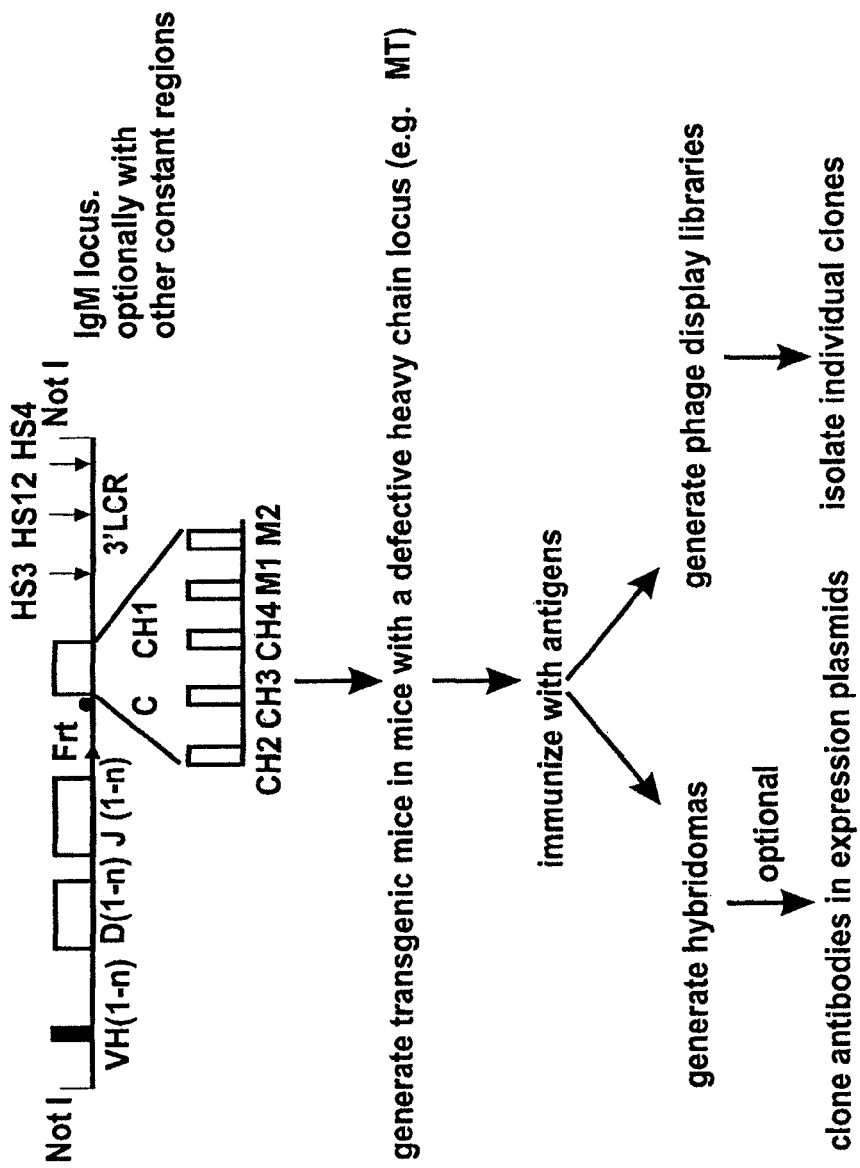

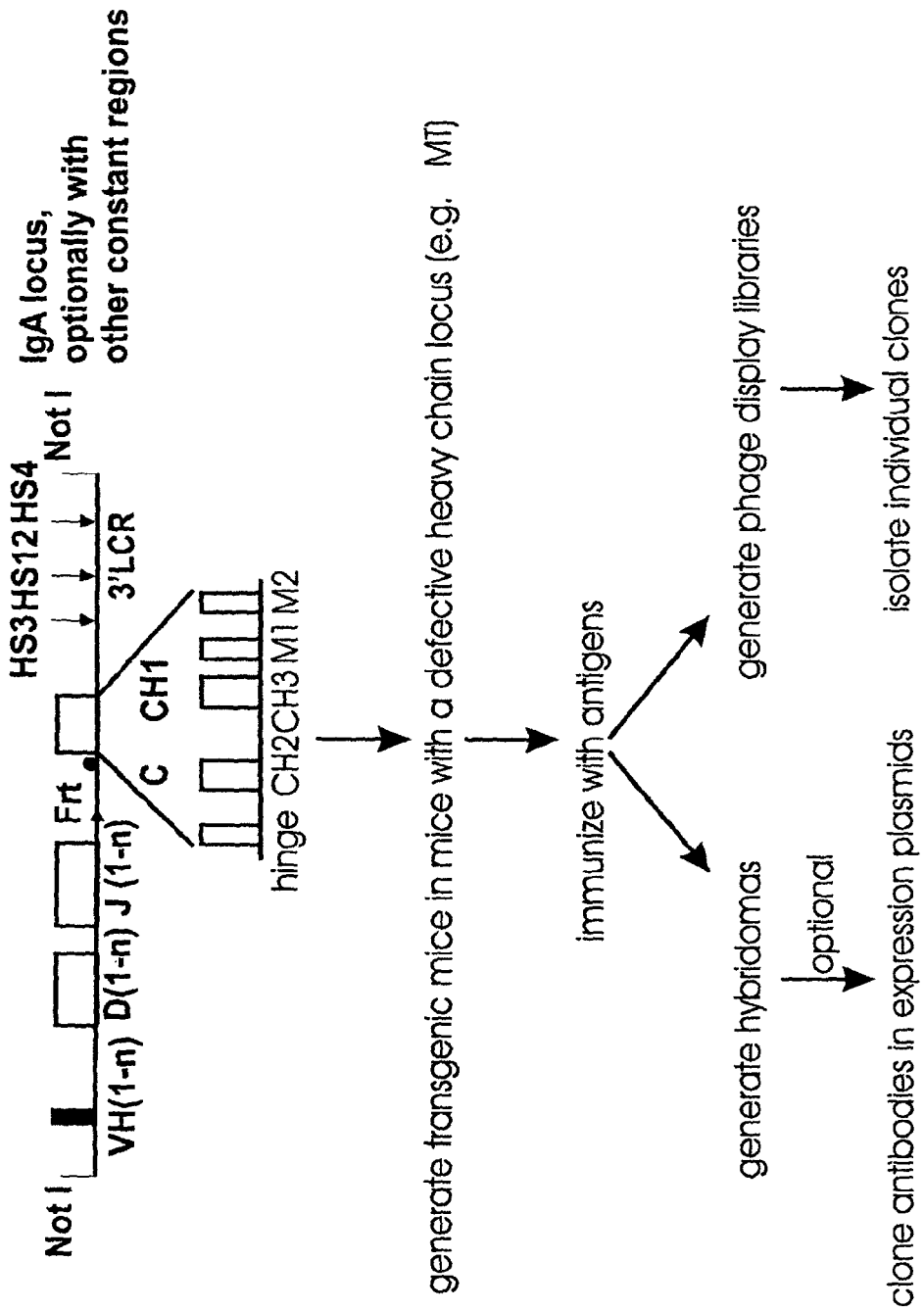

FIG. 9

```
            VHH                    D                              J
VDJg*1  GACACGGCCGTGTAGTATCTGTAAGGCAGATGG.................GGTAGTACTATGGTTCG....GGGA.
VDJg*2  GAC.............................................ATTCCCACTTCGATC....T....
VDJg*3  GACACGGCCGTCTATTACTGTAATGCCACTACG................ATATTTTGACTGGTTAT....TATA.
VDJg*4  GACACGGCCGTCCAATCGGAtACAG........................CTATGGTTACGTACTTT
VDJg*5  GACACGGCCGTCTATTACTGTAATGCAGATGTATTACTATGGTTCGGGGAGCCTATAGCCTTACTACTACTACGGTATG.

J                          CH1
VDJg*1  GTCCACCACTGCGGCTAGAGGGGCAGGGAACACTGGTCGCGGTGTCATCAGCCTCCACCAAGGGCCCATCGGTCTTCCC
VDJg*2  ................CTGGGGCCGTGGCACCCTGGTCACTGTCTCCTCAGCCTCCACCAAGGGCCCATCGGTCTTCCC
VDJg*3  GAC........GCTACTGGGGCCAGGGAACCCTGGTCACCGTCTCCTCAGCCTCCGCCAAGGGCCCATCGGTCTTCCC
VDJg*4  GACTA.........CTGGGGCCAGGGAACCCTGGTCACCGTCTCCTCAGCCTCCACCAAGGGCCCATCGGTCTTCCC
VDJg*5  GACGT.........CTGGGGCCAAGGGACCACGGTCACCGTCTCCTCAGCCTCCACCAAGGGCCCATCGGTCTTCCC
                                       CH1
VDJg*1  CCTGGCGCCCTGCTCCAGGAGCACCTCCGAGAGCACAGCGGCCCTGGGCTGCCTGGTCAAGGACTACTTCCCCGAACCGG
VDJg*2  CCTGGCGCCCTGCTCCAGGAGCACCTCCGAGAGCACAGCGGCCCTGGGCTGCCTGGTCAAGGACTACTTCCCCGAACCGG
VDJg*3  CCTGGCGCCCTGCTCCAGGAGCACCTCCGAGAGCACAGCGGCCCTGGGCTGCCTGGTCAAGGACTACTTCCCCGAACCGG
VDJg*4  CCTGGCGCCCTGCTCCAGGAGCACCTCCGAGAGCACAGCGGCCCTGGGCTGCCTGGTCAAGGACTACTTCCCCGAACCGG
VDJg*5  CCTGGCGCCCTGCTCCAGGAGCACCTCCGAGAGCACAGCGGCCCTGGGCTGCCTGGTCAAGGACTACTTCCCCGAACCGG
                                        CH1
VDJg*1  TGACGGTGTCGTGGAACTCAGGCGCTCTGACCAGCGGCGTGCACACCTTCCCAGCTGTCCTACAGTCCTCAGGACTCTAC
VDJg*2  TGACGGTGTCGTGGAACTCAGGCGCTCTGACCAGCGGCGTGCACACCTTCCCAGCTGTCCTACAGTCCTCAGGACTCTAC
VDJg*3  TGACGGTGTCGTGGAACTCAGGCGCTCTGACCAGCGGCGTGCACACCTTCCCAGCTGTCCTACAGTCCTCAGGACTCTAC
VDJg*4  TGACGGTGTCGTGGAACTCAGGCGCTCTGACCAGCGGCGTGCACACCTTCCCAGCTGTCCTACAGTCCTCAGGACTCTAC
VDJg*5  TGACGGTGTCGTGGAACTCAGGCGCTCTGACCAGCGGCGTGCACACCTTCCCAGCTGTCCTACAGTCCTCAGGACTCTAC
                                        CH1
VDJg*1  TCCCTCAGCAGCGTGGTGACCGTGCCCTCCAGCAACTTCGGCACCCAGACCTACACCTGCAACGTAGATCACAAGCCCAG
VDJg*2  TCCCTCAGCAGCGTGGTGACCGTGCCCTCCAGCAACTTCGGCACCCAGACCTACACCTGCAACGTAGATCACAAGCCCAG
VDJg*3  TCCCTCAGCAGCGTGGTGACCGTGCCCTCCAGCAACTTCGGCACCCAGACCTACACCTGCAACGTAGATCACAAGCCCAG
VDJg*4  TCCCTCAGCAGCGTGGTGACCGTGCCCTCCAGCAACTTCGGCACCCAGACCTACACCTGCAACGTAGATCACAAGCCCAG
VDJg*5  TCCCTCAGCAGCGTGGTGACCGTGCCCTCCAGCAACTTCGGCACCCAGACCTACACCTGCAACGTAGATCACAAGCCCAG
            CH1          Hinge
VDJg*1  CAACACCAAGAGCGCAAATGTTGTGTCGAG
VDJg*2  CAACACCAAGAGCGCAAATGTTGTGTCGAG
VDJg*3  CAACACCAAGAGCGCAAATGTTGTGTCGAG          GGTGGACAAGACAGTT
VDJg*4  CAACACCAAGAGCGCAAATGTTGTGTCGAG
VDJg*5  CAACACCAAGAGCGCAAATGTTGTGTCGAG
```

FIG. 16

B. Pertussis

1 RLSCAASGSIFSINAMGWYRQAPGKQRELVAAITSGGSTNYADSVKGRFTISRDNAKNTVYLQMNSLKPEDTAVYYCNAKGPITHVRG
2 RLSCAASGSIFSINAMGWYRQAPGKQRELVAAITSGGSTNYADSVKGRFTISRDNAKNTVYLQMNSLKPEDTAVYYCNAKTPITHIRG
3 RLSCAASGSIFSINAMGWYRQAPGKQRELVAAITSGGSTNYADSVKGRFTISRDNAKNTVYLQMNSLKPEDTAVYYCNARTPITVVRG
4 RLSCAASGSIFSINAMGWYRQAPGKQRELVAAITSGGSTNYADSVKGRFTISR(D)KAKNTVYLQMNSLKPE(D)SAVYYCNRTGPITHVRG
5 RLSCAASGSIFSINAMGWYRQAPGKQRELVAAITSGGST(N)(A)DSVKGRFTISRDNAKNTVYLQMNSLKPEDTAVYYCNAESPITKVRG

ELISA of VH against pertussis antigen fingerprint by restriction digestion of positive ELISA clones

| CDR3 | HINGE |
|---|---|
| ....VHYWGQGTLVTVSSERKCCV... | |
| ....VHHNGQGTLVTVSSERKCCV... | |
| ....VHYWGQGTLVTVSSERKCCV... | |
| ....VDYWGRGTLVTVSSERKCCV... | |
| ....VSYWGQGTLVTVSSERKCCV... | |

Sequence of clones indicated by an asterix in the fingerprint, note the short CDR3 region FIG. 18
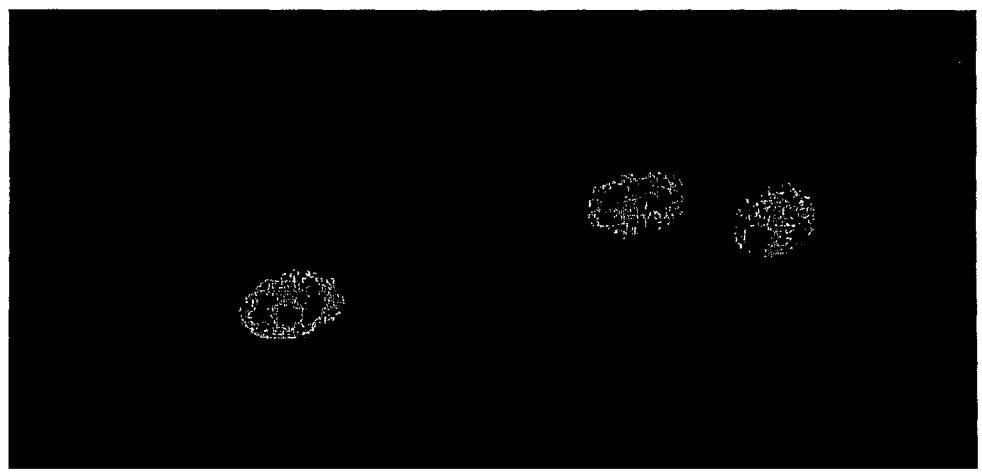
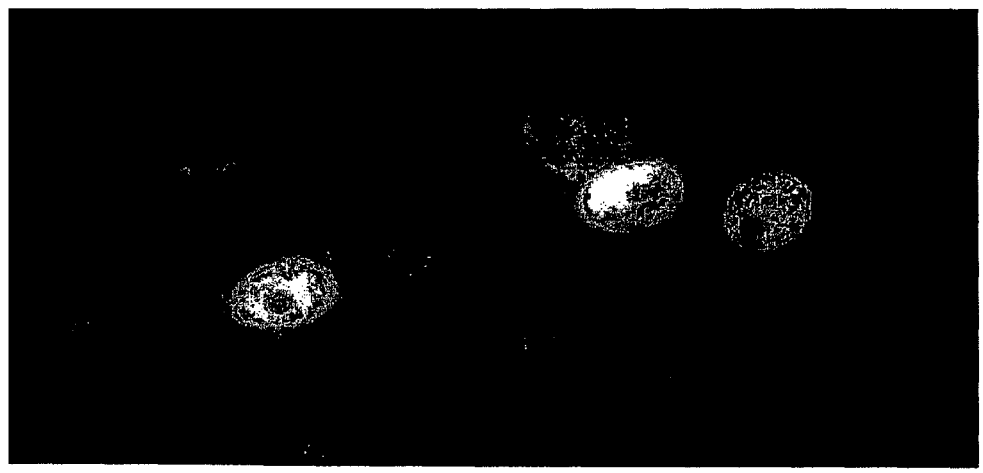

ELISA of single chain IgM and IgG antibodies raised against human TNF

Generation of the diabody expression plasmid

Generation of heavy chain only IgA

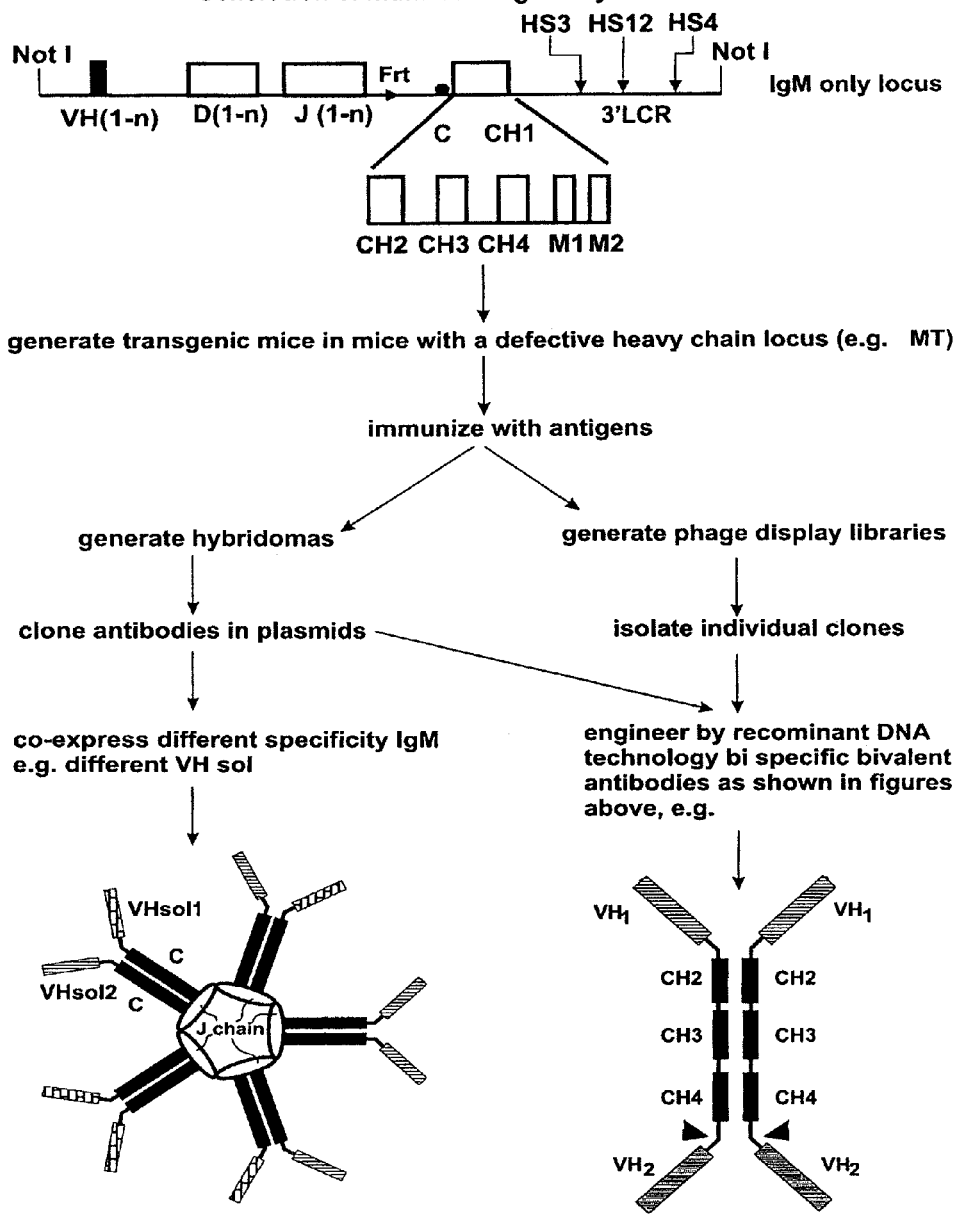

_

BINDING MOLECULES

CROSS-REFERENCE TO RELATED APPLICATIONS

The present application is a continuation of application Ser. No. 11/658,361, filed Oct. 10, 2008, now abandoned, which is a national stage of PCT International Application No. PCT/GB2005/002892, International Filing Date, Jul. 22, 2005, which claims priority under 35 U.S.C. 119(a) to Great Britain Application No. 0416392.9, Filed Jul. 22, 2004; Great Britain Application No. 0511881.5, Filed Jun. 10, 2005, each of which are incorporated herein by reference in their entireties.

FIELD OF THE INVENTION

The present invention relates to the manufacture of a diverse repertoire of functional heavy chain-only antibodies that undergo affinity maturation, and uses thereof. The invention also relates to the manufacture and use of a diverse repertoire of class-specific heavy chain-only antibodies and to the manufacture and use of multivalent polypeptide complexes with antibody heavy chain functionality, preferably antibody heavy chain binding functionality, constant region effector activity and, optionally, additional effector functions.

The present invention also relates to a method of generation of fully functional heavy chain-only antibodies in transgenic mice in response to antigen challenge. In particular, the present invention relates to a method for the generation of human antigen-specific, high affinity, heavy chain-only antibodies of any class, or mixture of classes and the isolation and expression of fully functional VH antigen-binding domains.

The present invention also relates to the generation of multivalent polypeptide complexes comprising heavy chain functionality, preferably heavy chain effector activity and other binding and effector functions.

Heavy chain-only antibodies and other multivalent binding complexes generated using the methods of the present invention and uses thereof are also described.

BACKGROUND TO THE INVENTION

Monoclonal antibodies or variants thereof will represent a high proportion of new medicines launched in the 20$^{st}$ century. Monoclonal antibody therapy is already accepted as a preferred route for the treatment for rheumatoid arthritis and Crohn's disease and there is impressive progress in the treatment of cancer. Antibody-based products are also in development for the treatment of cardiovascular and infectious diseases. Most marketed monoclonal antibody products recognise and bind a single, well-defined epitope on the target ligand (eg TNFα). Manufacture of human monoclonal antibodies for therapy remains dependent on mammalian cell culture. The assembly of a complex consisting of two heavy chains and two light chains (the $H_2L_2$ complex) and subsequent post-translational glycosylation processes preclude the use of bacterial systems. Production costs and capital costs for antibody manufacture by mammalian cell culture are high and threaten to limit the potential of antibody based therapies in the absence of acceptable alternatives. A variety of transgenic organisms are capable of expressing fully functional antibodies. These include plants, insects, chickens, goats and cattle but none as yet has been used to manufacture marketed therapeutic products.

Functional antibody fragments can be manufactured in *E. coli* but the product generally has low serum stability unless pegylated during the manufacturing process.

Bispecific antibody complexes are engineered Ig-based molecules capable of binding two different epitopes on the either the same or different antigens. Bispecific binding proteins incorporating antibodies alone or in combination with other binding agents show promise for treatment modalities where captured human immune functions elicit a therapeutic effect, for example the elimination of pathogens (Van Spriel et al., (1999) *J. Infect. Diseases*, 179, 661-669; Tacken et al., (2004) *J. Immunol.*, 172, 4934-4940; U.S. Pat. No. 5,487,890), the treatment of cancer (Glennie and van der Winkel, (2003) *Drug Discovery Today*, 8, 503-5100); and immunotherapy (Van Spriel et al., (2000) *Immunol. Today*, 21, 391-397; Segal et al., (2001) *J. Immunol. Methods*, 248, 1-6; Lyden et al., (2001) *Nat. Med.*, 7, 1194-1201).

Manufacturing issues are compounded where a bi-specific antibody product is based on two or more $H_2L_2$ complexes. For example, co-expression of two or more sets of heavy and light chain genes can result in the formation of up to 10 different combinations, only one of which is the desired heterodimer (Suresh et al., (1986) *Methods Enzymol.*, 121, 210-228).

To address this issue, a number of strategies have been developed for the production in mammalian cells of full length bispecific IgG formats (BsIgG) which retain heavy chain effector function. BsIgGs require engineered "knob and hole" heavy chains to prevent heterodimer formation and utilise identical L-chains to avoid L-chain mispairing (Carter, (2001) *J. Immunol. Methods*, 248, 7-15). Alternative chemical cross-linking strategies have also been described for the production of complexes from antibody fragments each recognising different antigens (Ferguson et al., (1995) Arthritis and Rheumatism, 38, 190-200) or the cross-linking of other binding proteins, for example collectins, to antibody fragments (Tacken et al., (2004) *J. Immunol.*, 172, 4934-4940).

The development of diabodies or mini antibodies (BsAb) generally lacking heavy chain effector functions also overcomes heterodimer redundancy. These comprise minimal single chain antibodies incorporating VH and VL binding sites (scFv) which subsequently fold and dimerise to form a divalent bispecific antibody monovalent to each of their target antigens (Holliger et al., (1993) *PNAS*, 90, 6444-6448; Muller et al., (1998) *FEBS Lett.*, 422, 259-264). In one instance, CH1 and L-constant domains have been used as heterodimerisation domains for bi-specific mini-antibody formation (Muller et al., (1998) *FEBS Lett.*, 259-264). A variety of recombinant methods based on *E. coli* expression systems have been developed for the production of BsAbs (Hudson, (1999) *Curr. Opin. Immunol.*, 11, 548-557), though it would appear that the cost and scale of production of clinical grade multivalent antibody material remains the primary impediment to clinical development (Segal et al., (2001) *J. Immunol. Methods*, 248, 1-6).

Recently, the BsAb concept has been extended to encompass Di-diabodies, tetravalent bispecific antibodies where the $V_H$ and $V_L$ domains on each H and L chain have been replaced by engineered pairs of scFv binding domains. Such constructs, whilst complex to engineer, can be assembled in mammalian cells in culture in the absence of hetero-dimer redundancy (Lu et al., (2003) *J. Immunol. Methods*, 279, 219-232).

The structure of immunoglobulins is well known in the art. Most natural immunoglobulins comprise two heavy chains and two light chains. The heavy chains are joined to each other via disulphide bonds between hinge domains located approximately half way along each heavy chain. A light chain is associated with each heavy chain on the N-terminal side of the hinge domain. Each light chain is normally bound to its respective heavy chain by a disulphide bond close to the hinge domain.

When an Ig molecule is correctly folded, each chain folds into a number of distinct globular domains joined by a more linear polypeptide sequence. For example, the light chain folds into a variable ($V_L$) and a constant ($C_L$) domain. Heavy chains have a single variable domain $V_H$, adjacent the variable domain of the light chain, a first constant domain, a hinge domain and two or three further constant domains. Interaction of the heavy ($V_H$) and light ($V_L$) chain variable domains results in the formation of an antigen binding region (Fv). Generally, both $V_H$ and $V_L$ are required for antigen binding, although heavy chain dimers and amino-terminal fragments have been shown to retain activity in the absence of light chain (Jaton et al., (1968) *Biochemistry*, 7, 4185-4195).

With the advent of new molecular biology techniques, the presence of heavy chain-only antibody (devoid of light chain) was identified in B-cell proliferative disorders in man (Heavy Chain Disease) and in murine model systems. Analysis of heavy chain disease at the molecular level showed that mutations and deletions at the level of the genome could result in inappropriate expression of the heavy chain $C_H1$ domain, giving rise to the expression of heavy chain-only antibody lacking the ability to bind light chain (see Hendershot et al., (1987) *J. Cell Biol.*, 104, 761-767; Brandt et al., (1984) *Mol. Cell. Biol.*, 4, 1270-1277).

Separate studies on isolated human $V_H$ domains derived from phage libraries demonstrated antigen-specific binding of $V_H$ domains but these $V_H$ domains proved to be of low solubility. Furthermore, it was suggested that the selection of human $V_H$ domains with specific binding characteristics displayed on phage arrays could form the building blocks for engineered antibodies (Ward et al., (1989) *Nature*, 341, 544-546).

Studies using other vertebrate species have shown that camelids, as a result of natural gene mutations, produce functional IgG2 and IgG3 heavy chain-only dimers which are unable to bind light chain due to the absence of the $C_H1$ light chain-binding region (Hamers-Casterman et al., (1993) *Nature*, 363, 446-448) and that species such as shark produce a heavy chain-only-like binding protein family, probably related to the mammalian T-cell receptor or immunoglobulin light chain (Stanfield et al., (2004) *Science*, 305, 1770-1773).

A characterising feature of the camelid heavy chain-only antibody is the camelid $V_H$ domain, which provides improved solubility relative to the human $V_H$ domain. Human $V_H$ may be engineered for improved solubility characteristics (see Davies and Riechmann, (1996) *Protein Eng.*, 9 (6), 531-537; Lutz and Muyldermans, (1999) *J. Immuno. Methods*, 231, 25-38) or solubility maybe be acquired by natural selection in vivo (see Tanha et al., (2001) *J. Biol. Chem.*, 276, 24774-24780). However, where $V_H$ binding domains have been derived from phage libraries, intrinsic affinities for antigen remain in the low micromolar to high nanomolar range, in spite of the application of affinity improvement strategies involving, for example, affinity hot spot randomisation (Yau et al., (2005) *J. Immunol. Methods*, 297, 213-224).

Camelid $V_H$ antibodies are also characterised by a modified CDR3 loop. This CDR3 loop is, on average, longer than those found in non-camelid antibodies and is a feature considered to be a major influence on overall antigen affinity and specificity, which compensates for the absence of a $V_L$ domain in the camelid heavy chain-only antibody species (Desmyter et al., (1996) *Nat. Struct. Biol.*, 3, 803-811, Riechmann and Muyldermans, (1999) *J. Immunol. Methods*, 23, 25-28).

Recent structural studies on camelid antibody suggests that antibody diversity is largely driven by in vivo maturation processes with dependency on V(D)J recombination events and somatic mutation, (De Genst et al., (2005) *J. Biol. Chem.*, 280 (14), 14114-14121).

Recently, methods for the production of heavy-chain-only antibodies in transgenic mammals have been developed (see WO02/085945 and WO02/085944). Functional heavy chain-only antibody of potentially any class (IgM, IgG, IgD, IgA or IgE) and derived from any mammal (including man) can be produced from transgenic mammals (preferably mice) as a result of antigen challenge.

The normal immunoglobulin heavy chain locus comprises a plurality of V gene segments, a number of D gene segments and a number of J gene segments. Each V gene segment encodes from the N terminal almost to the C terminal of a V domain. The C terminal end of each V domain is encoded by a D gene segment and a J gene segment. VDJ rearrangement in B-cells followed by affinity maturation provides $V_H$ binding domains which then, with $V_L$ binding domains, form an antigen recognition or binding site. Interaction of the heavy and light chains is facilitated by the $C_H1$ region of the heavy chain and the κ or λ region of the light chain.

For the production of heavy chain-only antibody, the heavy chain locus in the germline comprises gene segments encoding some or all of the possible constant regions. During maturation, a re-arranged $V_H$ binding domain is spliced onto the $C_H2$ constant region-encoding segment, to provide a re-arranged gene encoding a heavy chain which lacks a $C_H1$ domain and is therefore unable to associate with an immunoglobulin light chain.

Heavy chain-only monoclonal antibodies can be recovered from B-cells of the spleen by standard cloning technology or recovered from B-cell mRNA by phage display technology (Ward et al., (1989) *Nature*, 341, 544-546). Heavy chain-only antibodies derived from camelids or transgenic animals are of high affinity. Sequence analysis of normal $H_2L_2$ tetramers demonstrates that diversity results primarily from a combination of VDJ rearrangement and somatic hypermutation (Xu and Davies, (2000) *Immunity*, 13, 37-45). Sequence analysis of expressed heavy chain-only mRNA, whether produced in camelids or transgenic animals, supports this observation (De Genst et al., (2005) *J. Biol. Chem.*, 280, 14114-14121).

An important and common feature of natural camelid and human $V_H$ regions is that each region binds as a monomer with no dependency on dimerisation with a $V_L$ region for optimal solubility and binding affinity. These features have previously been recognised as particularly suited to the production of blocking agents and tissue penetration agents.

Homo- or hetero-dimers can also be generated by enzymatic cleavage of heavy chain-only antibodies or by synthetic routes (Jaton et al., (1968) *Biochemistry*, 7, 4185-4195 and US2003/0058074 A1). However the benefits of a monomeric antibody binding domain have yet to be used to advantage in design of multimeric proteins as reagents, therapeutics and diagnostics.

Human $V_H$ or camelid $V_{HH}$ produced by phage display technology lacks the advantage of improved characteristics as a result of somatic mutations and the additional diversity provided by D and J region recombination in the CDR3 region of the normal antibody binding site (Xu and Davies, (2000) *Immunity*, 13, 37-45). Camelid $V_{HH}$, whilst showing benefits in solubility relative to human $V_H$, is antigenic in man and must be generated by immunisation of camelids or by phage display technology.

The incorporation of $V_H$ binding domains has clear advantage over the use of scFvs which must be engineered from $V_H$ and $V_L$ domains with the associated potential of loss of specificity and avidity. $V_H$ binding domains derived from related gene families such as T-cell receptors or the shark immunogloblin family also provide alternatives to scFv for the generation of bi- or multi-specific binding molecules. Other naturally occurring binding proteins and domains thereof including, for example, soluble receptor fragments may also be used.

Antibody classes differ in their physiological function. For example, IgG plays a dominant role in a mature immune response. IgM is involved in complement fixing and agglutination. IgA is the major class of Ig in secretions—tears, saliva, colostrum, mucus—and thus plays a role in local immunity. The inclusion of class-specific heavy chain constant regions when engineering multivalent binding complexes provides the therapeutic benefits of effector function in vivo dependent on the functionality required. Engineering of individual effector regions can also result in the addition or deletion of functionality (Van Dijk and van der Winkel, *Curr. Opin. Chem. Biol.*, (2001) August 5 (4), 368-374). It seems likely that the optimal production and selection of heavy chain-only antibodies comprising high affinity $V_H$ binding domains (whether of human or camelid or other origin) will benefit from alternative approaches to those dependent on selection from randomised phage libraries which do not facilitate in vivo recombination and affinity maturation.

Thus, the inclusion of IgA constant region functionality would provide improved mucosal function against pathogens (Leher et al., (1999) *Exp. Eye. Res.*, 69, 75-84), whilst the presence of IgG1 constant region functionality provides enhanced serum stability in vivo. The presence of heavy chain $C_H2$ and $C_H3$ constant domains provides the basis for stable dimerisation as seen in natural antibodies, and provides recognition sites for post-translational glycosylation. The presence of $C_H2$ and $C_H3$ also allows for secondary antibody recognition when bispecific and multivalent complexes are used as reagents and diagnostics.

Isolated, pre-rearranged camelid heavy chain-only variable region sequences have previously been cloned in front of a hinge region and human IgG1 effector domain, inserted into vectors and expressed in COS cells to generate antibody. The antibodies expressed in this in vitro environment have already undergone the processes of class (isotype) switching and affinity maturation (hypermutation) in vivo in the camel and can bind to antigen (Riechmann and Muyldermans, (1999) *J. Immunol. Methods*, 231, 25-38).

There remains a need in the art to maximise heavy chain-only antibody diversity and B-cell response in vivo and, in particular, to generate a functional repertoire of class specific human heavy chain-only antibodies and functional $V_H$ heavy chain-only binding domains which retain maximum antigen-binding potential for use in diverse clinical, industrial and research applications.

There also remains a need in the art to produce a soluble, bi-valent or multi-valent polypeptide binding complex comprising at least part of an antibody heavy chain, alone or in combination with an effector (light) chain, which is physiologically stable and has effector function.

BRIEF SUMMARY OF THE INVENTION

The present invention provides a method for the production of a VH heavy chain-only or a camelid $V_H$ ($V_{HH}$) heavy chain-only antibody in a transgenic mammal comprising the step of expressing a heterologous $V_H$ or camelid $V_H$ ($V_{HH}$) heavy chain locus in that mammal, wherein the $V_H$ or camelid $V_H$ ($V_{HH}$) heavy chain locus comprises a heavy chain constant region which does not encode a $C_H1$ domain and which locus, when expressed, is capable of forming heavy chain-only antibodies of defined class or classes.

The $V_H$ or camelid $V_H$ ($V_{HH}$) heavy chain locus may comprise one or more camelid or non-camelid V gene segments. Preferably, the V gene segment has been selected or engineered to show improved solubility characteristics. Preferably the V gene segment is derived from a human.

The heavy chain constant region of the heavy chain locus may comprise a $C\alpha_1$ and/or a $C\alpha_2$, a $C\epsilon$, a $C\delta$, a $C\gamma$ and/or a $C\mu$, heavy chain constant region gene. Furthermore, the heavy chain constant region of the heavy chain locus may comprise more than one of the following heavy chain constant regions: $C\alpha_1$, $C\alpha_2$, $C\epsilon$, $C\delta$, $C\gamma$ $C\mu$.

Preferably, the $V_H$ heavy chain locus comprises a variable region comprising at least one human or camelid V gene segment, at least one D segment and at least one J segment wherein a human or camelid V gene segment, a D gene segment and a J gene segment are capable of recombining to form a VDJ coding sequence. The heavy chain locus preferably comprises twenty or more D gene segments and/or five or more J gene segments. Preferably, D and J segments are of vertebrate origin, preferably human. The CDR3 loop may be derived using D and J gene segments derived from any vertebrate and are preferably human D and J gene segments.

The $V_H$ heavy chain locus may also comprise a recombination sequence (rss) capable of recombining a J gene segment directly with a heavy chain constant region gene.

The heavy chain constant region of the heterologous heavy chain locus is of human origin or vertebrate origin e.g. of camelid origin. Alternatively the constant region may not be of immunoglobulin heavy chain origin.

Preferably, the methods of the invention result in essentially normal B-cell maturation. The present invention also provides a heavy chain-only antibody, or a fragment thereof, or a mixture of classes of heavy chain-only antibodies obtained or obtainable according to a method of the invention. This heavy chain-only antibody may be a monoclonal antibody, or fragment thereof, such as a human or camelid $V_H$ binding domain. The $V_H$ binding domain of the invention may lack an extended camelid-like CDR3 loop or, alternatively, may comprise an extended camelid-like CDR3 loop.

The present invention also provides a vector comprising a heterologous heavy chain locus of the invention and a host cell transformed with such a vector.

The invention also provides a transgenic mammal expressing a heterologous heavy chain locus described herein. Preferably, the transgenic mammal of the invention has a reduced capacity to produce antibodies that include light chains.

Also provided is the use of a heavy chain-only antibody, or fragment thereof, according to the invention, in the preparation of a medicament for immunotherapy. The heavy chain-only antibodies of the invention may also be used as diagnostics, reagents, abzymes or inhibitory agents. Also provided is a pharmaceutical composition comprising the heavy chain-only antibody or fragment thereof according to the invention, and a pharmacologically appropriate carrier.

The invention also provides a method of production and selection of heavy chain-only antibodies comprising the steps of:
 (a) injecting an antigen into the transgenic mammal as described herein;
 b) isolating a cell or tissue expressing an antigen-specific, heavy chain-only antibody of interest; and
 c) producing a hybridoma from the cell or tissue of step (b) and d) optionally cloning the heavy chain-only antibody mRNA from said hybridoma for subsequent production in a heterologous expression system such as a mammalian, plant, insect, microbial, fungal or alternative system.

$V_H$ binding domains may then be produced by identifying and isolating an antigen-specific $V_H$ domain from the cloned mRNA of step c).

$V_H$ binding domains of the invention may also be produced by:
(a) injecting an antigen into the transgenic mammal described herein;
b) isolating a cell or tissue expressing an antigen-specific, heavy chain-only antibody of interest;
c) cloning the $V_H$ locus from mRNA derived from the isolated cell or tissue;
d) displaying the encoded protein using a phage or similar library;
e) identifying antigen-specific $V_H$ domain(s); and
f) expressing the $V_H$ domain(s) alone or as a fusion protein in bacterial, yeast or alternative expression systems.

DETAILED DESCRIPTION OF THE INVENTION

The present inventors have overcome the limitations of the prior art and shown that transgenic animals, in particular mice, can be generated using "micro loci" to produce class-specific, heavy chain-only antibodies, or a mixture of different classes of heavy chain-only antibodies which are secreted by plasma or B cells. These can then be used either to generate a reliable supply of class-specific, heavy chain-only antibody using established hybridoma technology or as a source of functional camelid $V_H$ ($V_{HH}$) binding domains or $V_H$ heavy chain-only binding domains, preferably a soluble $V_H$ heavy chain-only binding domains of human origin, which are free of effector functions but which retain binding function.

Heavy chain-only antibodies (including camelid antibodies) that can be generated by the methods of the invention show high binding affinity, resulting from V, D and J gene segment rearrangements and somatic mutations, generally in the absence of an enlarged CDR3 loop. Essentially normal B-cell maturation is observed with high levels of heavy chain-only antibody present in isolated plasma (provided that the $C_H1$ domain has been eliminated from all antibody classes present in the recombinant locus). B-cell maturation and the secretion of assembled dimers (eg IgG) or multimers (eg IgM) has no dependency on the presence or expression of light chain genes.

Nucleotide sequence analysis of antigen-specific mRNA encoding an antigen-specific heavy chain isolated from hybridomas derived from transgenic mice has demonstrated that heavy chain antibody diversity is primarily a function of VDJ recombination. Furthermore, the present inventors have shown that antibody diversity is generated in the CDR3 region of the functional antigen-binding domain of the heavy chain-only antibody with a more limited contribution from somatic mutations in the $V_H$ domains. Using the methods described herein, functional $V_H$ domains can be cloned and expressed in bacterial systems to generate $V_H$ binding domains with full retention of antigen binding, specificity and affinity. In addition, class-specific heavy chain dimers and multimers can be secreted by hybridoma cell lines in culture.

The invention also teaches that transgenic mice can be programmed to produce preferred classes of heavy chain-only antibody in response to antigen challenge, eg only IgG as opposed to only IgM or, for example, mixtures of IgA, IgG and IgM.

The inventors have previously described (see WO02/085945 and WO02/085944) the generation of transgenic mice expressing a minimal human IgG heavy chain constant region locus devoid of the $C_H1$ exon and linked by human D and J segments with two llama VHH genes. These produce functional, high affinity, antigen-specific IgG heavy chain-only antibody when challenged with antigen. Mixtures of heavy chain-only antibody classes (IgM and IgG) can be obtained by class switching in vivo through utilisation of gene constructs incorporating heavy chain constant regions in tandem (provided that all constant region genes lack a $C_H1$ domain and, when present, a $C_H4$ domain).

The improvements described herein show that a mouse constructed with the same IgG constant region locus linked by human D and J segments with two llama $V_{HH}$ genes and a human IgM constant region locus devoid of a $C_H1$ exon linked by the same human D and J gene segments with two llama $V_{HH}$ genes, also produces high molecular weight (multimeric) IgM heavy chain-only antibody and IgG (dimer) heavy chain-only antibody. Surprisingly, essentially normal B-cell maturation and antibody production is dependent on the complete absence of $C_H1$ sequences from each heavy chain constant region present in the transgenic locus. Moreover, there is no requirement for the removal of the $C_H4$ exon if present.

Thus, for example, a transgenic animal carrying a human IgM heavy chain locus with a functional $C_H1$ exon linked by the same human D and J gene segments to two llama V gene segments, and IgG constant heavy chain region locus devoid of the $C_H1$ exon linked by the same human D and J gene segments to two llama V gene segments, produces very low levels of heavy chain-only antibody and shows no evidence for B-cell maturation.

Other effector domains, including the $C_H4$ domain, may be incorporated or not, as desired, to introduce to, or eliminate from, the resultant heavy chain-only antibody, effector features.

The inventors have found that productive expression of antibody (ie B-cell maturation) can result from the use of any V gene segment present in the construct. Isolation and sequencing of antibody mRNA derived from B-cells shows that D and J gene segment recombination occurs to generate CDR3 diversity. Sequence comparison of resultant $V_H$ domains reveals somatic mutations, indicating that affinity maturation events have occurred in the recombined D and J gene segments and also in the $V_H$ domain of the resultant expressed antibody mRNA.

Preferred constructs incorporate V gene segments selected or engineered for improved solubility and linked to a D and J chain cluster for recombination and CDR3 generation. Preferably, the VDJ sequences are linked to constant effector domain(s) of choice in tandem, each devoid of a $C_H1$ exon.

The invention is not limited to the derivation and production of human or camelid class-specific, heavy chain-only antibody or human $V_H$ binding domains (preferably soluble $V_H$ binding domains) (alone or linked to the effector domain of choice), but encompasses the production of chaemeric combinations of any V gene segment of vertebrate origin (optionally engineered to improve solubility characteristics) linked to D and J gene segments. Preferably, the V gene segments are of human origin and are not V gene segments derived from a camelid. The resultant $V_H$ domains may not comprise an enlarged camelid-like CDR3 loop unless the D and J segments have been derived from a camelid. This results in a $V_H$ domain exhibiting CDR3 diversity and affinity maturation operationally linked to an effector constant region. The latter ensures functional secretion and optionally assembly in the parent transgenic vertebrate of choice and also provides subsequent selectable effector function should this be required.

These observations have important implications for the improved and simplified engineering of class-specific, heavy chain-only antibodies and the derivation of high affinity, soluble $V_H$ domains which incorporate affinity maturation via somatic mutation. Incorporation of select heavy chain constant region effector functions (devoid of $C_H1$) or mixtures thereof permits the production of any class of heavy chain-only antibodies or any mixture of heavy chain-only antibodies without the requirement of additional antibody engineering. $V_H$ domains can be expressed alone in bacterial or other micro-organism systems or as functional heavy chain-only antibody incorporating effector domains secreted by hybridomas or transfected cells in culture. Antibodies and $V_H$ binding domains of human origin have wide ranging applications in the field of healthcare as medicines, diagnostics and reagents, with parallel agricultural, environmental and industrial applications.

Thus, in a first aspect, the present invention provides a method for the production of a $V_H$ heavy chain-only antibody in a transgenic mammal comprising the step of expressing a heterologous $V_H$ heavy chain locus in that mammal. Preferably, the $V_H$ heavy chain locus comprises a heavy chain constant region which does not encode a CH1 domain and which locus is capable of forming a diverse repertoire of complete heavy chain-only antibodies when expressed.

The first aspect of the present invention also provides a method for the production of a camelid $V_H$ heavy chain-only antibody in a transgenic mammal comprising the step of expressing a camelid $V_H$ heavy chain locus in that mammal, wherein the $V_H$ heavy chain locus comprises a heavy chain constant region which does not encode a $C_H1$ domain and which locus, when expressed, is capable of forming a diverse repertoire of complete heavy chain-only antibodies incorporating VDJ rearrangement and affinity maturation in response to antigen challenge.

Heavy chain effector molecules may be engineered to be free of functional domains, for example the carboxy-terminal $C_H4$ domains, provided that engineering does not affect secretory mechanisms preventing cell surface assembly and consequently B-cell maturation. The $C_H1$ exons alone are deleted from the heterologous locus or are absent from the locus. Additional features maybe engineered into the locus, for example to improve glycosylation, or add function.

Preferably, the heterologous locus, when expressed, is capable of forming functional IgA, IgE, IgG, IgD or IgM molecules or isotypes thereof. Individual antibody classes or mixtures of antibody classes or isotypes thereof may also be produced.

Accordingly, the heterologous heavy chain locus is designed to produce preferred classes or mixtures of heavy chain-only antibody depending on the antibody class(es) required, with essentially normal B-cell maturation. The utilisation of camelid V, D and J gene segments and camelid effector regions will produce camelid antibodies with features peculiar to camelids, such as enlarged CDR3 loops. The use of human V, D and J gene segments comprising V gene segments randomly selected, or selected or engineered for enhanced solubility, will produce functional human heavy chain-only antibodies.

Antibodies obtained according to the invention have the advantage over those of the prior art in that they are of substantially any single or known class and preferably of human origin. Antibodies are of high affinity resulting from a combination of VDJ recombination and affinity maturation in vivo. Antibodies and fragments thereof may be may be isolated, characterised and manufactured using well-established methods known to those skilled in the art.

The Heterologous Heavy Chain Locus

In the context of the present invention, the term 'heterologous' means a nucleotide sequence or a locus as herein described which is not endogenous to the mammal in which it is located.

A "$V_H$ heavy chain locus" in the context of the present invention relates to a minimal micro-locus encoding a $V_H$ domain comprising one or more V gene segments, one or more D gene segments and one or more J gene segments, operationally linked to one or more heavy chain effector regions (each devoid of a $C_H1$ domain). Preferably, the primary source of antibody repertoire variability is the CDR3 region formed by the selection of D and J gene segments by the V-D and D-J junctions.

The advantage of the present invention is that antibody repertoire and diversity obtained in the rearranged $V_H$ gene sequences can be maximised through the use of multiple D and J gene segments. Subsequent somatic mutation is achieved whilst using a minimal locus (micro-locus) without the need for a large number of V gene segments or the $V_L$ and $L_C$ (light chain) immunoglobulin loci.

Preferably, the $V_H$ heavy chain locus comprises from two to five V (2, 3, 4 or 5) gene segments derived from any vertebrate species.

Preferably, the V gene segments are of human origin, optionally selected or engineered for improved solubility.

Preferably, the $V_H$ heavy chain locus comprises from two to forty (2, 3, 4, 5, 6, 7, 8, 9, 10, 12, 14, 16, 18, 20, 30 or 40) or more D gene segments. The D gene segments may be derived from any vertebrate species but, most preferably, the D gene segments are human D gene segments (normally 25 functional D gene segments).

Preferably, the $V_H$ heavy chain locus comprises from two to twenty (2, 3, 4, 5, 6, 7, 8, 9, 10, 12, 14, 16, 18 or 20) or more J gene segments. The J gene segments may be derived from any vertebrate species but, most preferably, the J gene segments are human J gene segments (normally 6 J gene segments).

Preferably, the $V_H$ heavy chain locus comprises two or more V gene segments, twenty-five functional human D gene segments and 6 human J gene segments.

The term 'V gene segment' encompasses a naturally occurring V gene segment derived from a vertebrate, including camelids and human, which have optionally been selected, mutated, or engineered for improved characteristics, such as solubility. V gene segments are also found in other species such as shark (see Kokubu et al., (1988) *EMBO. J.,* 7, 3413-3422) or have evolved to provide diverse $V_H$-like families of binding proteins exemplified, for example, in the evolution of the immunoglobulin light chain $V_L$ repertoire or the T-cell receptor $V_H$ repertoire.

Preferred methods of improving solubility of a $V_H$ domain incorporate rational, as opposed to only random, means and are exemplified in Davies and Reichmann, (1996) *Protein Eng.,* 9 (6), 531-537 and Riechmann and Muyldermans, (1999) *J. Immunol. Methods,* 231, 25-38. Natural selection can also occur in vivo through affinity maturation and the incorporation of favourable mutations in the $V_H$ gene following VDJ re-arrangement.

The V gene segment must be capable of recombining with a D gene segment, a J gene segment and a heavy chain constant (effector) region (which may comprise several exons but excludes a $C_H1$ exon) according to the present invention to generate a $V_H$ heavy chain-only antibody when the nucleic acid is expressed.

A V gene segment according to the present invention also includes within its scope any gene sequence encoding a homologue, derivative or protein fragment, which is capable of recombining with a D gene segment, a J gene segment and a heavy chain constant region (comprising one or more exons but not a $C_H1$ exon) according to the present invention to generate a heavy chain-only antibody as defined herein.

Thus $V_H$ coding sequences may be derived from a naturally occurring source or they may be synthesised using methods familiar to those skilled in the art.

A "$V_H$ domain" in the context of the present invention refers to an expression product of a V gene segment when recombined with a D gene segment and a J gene segment as defined above. Preferably, the $V_H$ domain as used herein remains in solution and is active in a physiological medium without the need for any other factor to maintain solubility. Preferably, the ability of the soluble $V_H$ domain to bind antigen has been improved by VDJ recombination and somatic mutation. There is no dependency on the presence or absence of the enlarged CDR3 loop peculiar to the camelid species. The $V_H$ domain is able to bind antigen as a monomer and, when combined with effector constant regions, may be produced in mono-specific, bi-specific, multi-specific, bi-valent or multivalent forms, dependent on the choice and engineering of the effector molecules used (eg IgG, IgA IgM etc.) or alternative mechanisms of dimerisation and multimerisation. Any likelihood of binding with a $V_L$ domain when expressed as part of a soluble heavy chain-only antibody complex has been eliminated by removal of the $C_H1$ exon (see Sitia et al., (1990) Cell, 60, 781-790). The $V_H$ domain alone can also be engineered with diverse protein domains to produce fusion proteins for targeted therapeutic and diagnostic purpose, for example with toxins, enzymes and imaging agents.

In the context of the present invention the terms 'a D gene segment' and 'a J gene segment' includes naturally occurring sequences of D and J gene segments. Preferably, the D and J gene segments are derived from the same vertebrate from which the V gene segment is derived. For example, if a V gene segment is derived from a human and then solubilised or engineered, the D and J gene segments are preferably also derived from a human. Alternatively the V gene segments maybe derived, for example, from camel and the D and J gene segments from human or vice versa.

The terms D gene segment and J gene segment also include within their scope derivatives, homologues and fragments thereof as long as the resultant segment can recombine with the remaining components of a heavy chain antibody locus as herein described to generate a heavy chain-only antibody as herein described. D and J gene segments may be derived from naturally occurring sources or they may be synthesised using methods familiar to those skilled in the art and described herein. The V, D and J gene segments are capable of recombination and preferably undergo somatic mutation.

The V, D and J gene segments are preferably derived from a single vertebrate species. This may be any vertebrate species but is preferably a human.

In addition, a heterologous heavy chain locus according to the present invention comprises a region of DNA encoding a heavy chain constant region providing effector functions in vivo (eg IgG, IgM, IgA, IgE, IgD or isotypes thereof).

The invention also provides an antigen-specific, heavy chain-only antibody obtained or obtainable by the methods of the present invention.

The Heavy Chain Constant Region

Operationally, a heavy chain constant region is encoded by a naturally occurring or engineered gene segment that is capable of recombining with a V gene segment, a D gene segment and a J gene segment in a B cell. Preferably the heavy chain constant region is derived from an immunoglobulin locus.

According to this aspect of the invention, each heavy chain constant region essentially comprises at least one heavy chain constant region gene, which is expressed without a functional $C_H1$ domain so that generation of heavy chain-only antibody can occur. Each heavy chain constant region may also comprise one or more additional heavy chain constant region exons, which are selected from the group consisting of Cδ, $C\gamma_{1-4}$, Cμ, Cε and $C\alpha_{1-2}$ with the proviso that the additional heavy chain constant region genes also do not express a functional $C_H1$ domain. The heavy chain constant region gene segments are selected depending on the preferred class or mixture of antibody classes required. Optionally, the heterologous heavy chain locus is Cμ- and Cδ-deficient.

For instance, Ig molecules of class M are known to play an important role in the activation of macrophages and the complement pathway. Due to the close proximity of its binding sites, IgM has a high avidity for pathogens, including viruses. However, IgM is also known to be difficult for use in rapid immunoassay techniques whereas Ig of class G can be readily used in these techniques. For such uses, it would be useful to select for the preferred antibody class, ie IgG or IgM.

The expression of all or part of a heterologous heavy chain $C_\gamma$ locus devoid of $C_H1$ will produce optionally some or all IgG isotypes, dependent on the IgG1, IgG2, IgG3 and IgG4 isotypes present in the heterologous IgG locus. Alternatively the heavy chains may comprise Cε genes. The resulting IgE molecule might also be used in therapy.

Alternatively, selected mixtures of antibodies may be obtained. For example, IgA and IgM may be obtained when the heavy chain constant region comprises a Cα and a Cμ gene.

Preferably, the heavy chain constant region according to the present invention is of human origin, in particular when the heavy chain antibody is to be used for therapeutic applications in humans. Where the heavy chain antibodies are to be used for diagnostic or veterinary purposes, the heavy chain constant region is preferably derived from the target organism, vertebrate or mammal in or on which diagnosis or veterinary therapy is to be performed.

When expressed, the heavy chain constant region lacks a functional $C_H1$ domain. The $C_H1$ exon and, optionally, Cμ and Cδ constant regions, may be mutated, deleted or substituted. Preferably, the $C_H1$ exon is deleted. The presence, for example, of IgM with a functional $C_H1$ domain inhibits B-cell maturation and consequently limits the productive expression of heavy chain only IgG (devoid of $C_H1$) within the same locus, as B-cell maturation is inhibited.

A 'heavy chain constant region exon' ('$C_H$ exon') as herein defined includes the sequences of naturally occurring vertebrate, but especially mammalian, $C_H$ exons. This varies in a class specific manner. For example, IgG and IgA are naturally devoid of a $C_H4$ domain. The term '$C_H$ exon' also includes within its scope derivatives, homologues and fragments thereof in so far as the $C_H$ exon is able to form a functional heavy chain-only antibody as herein defined when it is a component of a heavy chain constant region.

Optionally, when present, the $C_H4$ or other functional domains maybe engineered or deleted within the transgene provided such a process does not inhibit the intracellular secretory process, B-cell maturation or the binding activity of the resultant antibody polypeptide.

Mammals

The transgenic mammal used in the methods of the invention is not a human. The transgenic mammal is preferably a rodent such as a rabbit, guinea pig, rat or mouse. Mice are especially preferred. Alternative mammals such as goats, sheep, cats, dogs or other animals may also be employed.

Preferably transgenic animals are generated using established oocyte injection technology and, where established, ES cell technology or cloning.

Advantageously, immunoglobulin heavy and optionally light chain loci endogenous to the mammal are deleted or silenced when a heavy chain-only antibody is expressed according to the methods of the invention.

This approach of generating heavy chain-only antibodies as described above maybe of particular use in the generation of antibodies for human therapeutic use as often the administration of antibodies to a species of vertebrate which is of different origin from the source of the antibodies results in the onset of an immune response against those administered antibodies.

Therefore, in a further aspect, the present invention provides a transgenic mammal expressing a heterologous heavy chain locus according to the present invention.

The transgenic mammal may be engineered to have a reduced capacity to produce antibodies that include light chains.

Antibody-producing cells may be derived from transgenic animals according to the present invention and used, for example, in the preparation of hybridomas for the production of heavy chain-only antibodies as herein defined. In addition or alternatively, nucleic acid sequences may be isolated from transgenic mammals according to the present invention and used to produce $V_H$ domain heavy chain-only chain antibodies or bi-specific/bi-functional complexes thereof, using recombinant DNA techniques which are familiar to those skilled in the art.

Alternatively or in addition, antigen-specific heavy chain-only antibodies may be generated by immunisation of a transgenic animal according to the present invention.

Thus in a further aspect, the present invention provides a method for the production of heavy chain-only antibodies by immunising a transgenic mammal according to the present invention with an antigen.

In a preferred embodiment of this aspect of the invention, the mammal is a mouse.

Heavy Chain-Only Antibodies and Fragments Thereof.

In a further aspect, the present invention provides a heavy chain-only antibody obtainable according to a method of the present invention and functional fragments and derivatives thereof. Fragments encompassing the VH binding domain can be derived by enzymic cleavage or cyanogen bromide cleavage of a heavy chain-only antibody of the invention ie devoid of light chains (Jaton et al., (1968) *Biochemistry*, 7, 4185-4195).

A preferred functional fragment is an antigen-specific, heavy chain-only binding domain, ie a $V_H$ binding domain, as expressed by the $V_H$ locus as a result of recombination between single V, D and J gene segments followed subsequently by somatic mutation. According to this aspect of the invention $V_H$ loci can be cloned from, eg, mRNA isolated from an antibody-producing cell of an immunised transgenic animal as described above. Cloned sequences can then be displayed using a phage (Ward et al., (1989) *Nature*, 341, 544-546) or similar display libraries, for example using yeast-based systems (Boder and Wittrup, (1997) *Nat. Biotechnol.*, 15, 553-7) and antigen-specific $V_H$ binding domains identified. Antigen-specific heavy chain binding domains can then be manufactured either alone or as fusion proteins in scalable bacterial, yeast or alternative expression systems. Sequences encoding $V_H$ binding domains can also be cloned from characterised hybridomas derived by classical procedures from immunised transgenic mice. These can then be used for the production of $V_H$ binding domains and derivatives thereof including the engineering of defined antibody classes (eg IgE or IgA) and variants thereof with differing effector functions.

Accordingly, the invention also provides a method of producing a $V_H$ binding domain comprising the steps of:
 a) isolating a cell or tissue expressing an antigen-specific heavy chain-only antibody of interest (preferably a soluble, antigen-specific heavy chain-only antibody of interest);
 b) cloning the sequence encoding the $V_H$ binding domain from mRNA derived from the isolated cell or tissue;
 c) displaying the encoded protein using a phage or similar library;
 d) identifying antigen-specific $V_H$ binding domains, and
 e) expressing the $V_H$ binding domains alone or as a fusion protein in bacterial, yeast, mammalian or alternative expression systems.

Alternatively, $V_H$ domain-containing fragments can be generated from heavy chain-only antibodies of the invention using enzymic or chemical cleavage technology and subsequent separation of the $V_H$ domain-containing fragment from the other cleavage products.

Where the $V_H$ binding domain is isolated from a characterised hybridoma, the cloned $V_H$ binding domain sequence derived from mRNA can be directly cloned into an expression vector without recourse to additional selection steps using phage and other display systems.

Production systems for heavy chain only-antibody incorporating effector regions include mammalian cells in culture (eg CHO cells), plants (eg maize), transgenic goats, rabbits, cattle, sheep, chickens and insect larvae suited to mass rearing technology. Other production systems, including virus infection (eg baculovirus in insect larvae and cell-lines) are alternatives to cell culture and germline approaches. Other production methods will also be familiar to those skilled in the art. Where there is a requirement for heavy chain-only IgA or IgM assembly, the co-expression of a "J chain" is beneficial. Suitable methods for the production of camelid heavy chain-only antibody or $V_H$ binding domains alone are known in the art. For example camelid $V_H$ binding domains have been produced in bacterial systems and camelid heavy chain-only homodimers have been produced in hybridomas and transfected mammalian cells (see Reichmann and Muyldermans, (1999) *J. Immunol. Methods*, 231, 25-38).

Methods are also well established for the expression of engineered human $V_H$ binding domains derived using phage display technology (Tanha et al., (2001) *J. Biol. Chem.*, 276, 24774-24780 and references therein).

Insect larvae from transgenic fly lines have been shown to produce functional heavy chain-only antibody fragments in haemolymph with characteristics indistinguishable from the same antibody produced by mammalian cells (PCT/GB2003/0003319). The present invention also provides an antigen-specific monomeric or dimeric $V_H$ binding domain obtainable according to the method of this aspect of present invention.

The present invention also provides a polynucleotide sequence consisting of the heterologous heavy chain locus, an isolated polynucleotide encoding a heavy chain-only antibody of the invention and a vector comprising a heterologous heavy chain locus, or fragment thereof, or isolated polynucleotide encoding a heavy chain-only antibody according to the present invention.

The present invention also provides a host cell transformed with a heterologous heavy chain locus, or fragment thereof, or isolated polynucleotide encoding the heavy chain-only antibody or antibody fragment, according to the present invention.

In a second aspect, the present invention provides a polypeptide complex comprising an antigen-specific $V_H$ binding domain according to the present invention having attached to it an effector moiety which provides effector activity. This effector activity may be in addition to that provided by the heavy chain constant region and may be situated at the amino or carboxy terminus of the molecule. These polypeptide complexes retain the physiological function conferred by the antigen-specific $V_H$ binding domain in combination with additional targeting or effector functions of the effector moieties. Such polypeptide complexes may be in the form of functional monomers or, dependent on the design and interaction of the effector moieties, dimers, tetramers, pentamers, multimers or other complexes incorporating different $V_H$ binding domains, so imparting multi-valency and multi-specificity. $V_H$ binding domains may be present at the amino or carboxy terminus of the binding molecule (see FIG. 1 for dimeric example).

If the effector moiety comprises a binding domain, it may have a different specificity from the antigen-specific $V_H$ binding domain. The advantage of this arrangement is that the polypeptide complex can facilitate cross-linking of different targets. For example, a bispecific polypeptide complex may be utilised to enhance cell-cell interactions and cell/pathogen interactions. In this embodiment, the polypeptide complexes of the invention can be utilised, for example, to bridge between two cell types such as a pathogen and a macrophage (see Biburger et al., (2005) *J. Mol. Biol.*, 346, 1299-1311). The use of $V_H$ binding domains is preferable to the use of scFV binding domains in such bi-specific designs. $V_H$ binding domains have high binding affinity and can be incorporated into such polypeptide complexes with minimal vector construction and in the absence of design considerations necessary to maintain the specificity and affinity of scFVs relative to their tetrameric parental molecule. Where dimers or multimeric polypeptide complexes are envisaged dimerisation domains are incorporated, for example the inclusion of $C_H2$ and $C_H3$ domains derived from immunoglobulin heavy chain constant regions (see FIG. 2).

The term 'effector moiety' as used herein includes any moiety that mediates a desired biological effect on a cell. The effector moiety is preferably soluble and may be a peptide, polypeptide or protein or may be a non-peptidic structure. For example, the effector moiety may be an enzyme, hormone, cytokine, drug, pro-drug, toxin, in particular a protein toxin, a radionuclide in a chelating structure, a binding domain, a dimerising or interaction domain, an imaging agent, albumin or an inhibitory agent.

Albumin may be utilised as an effector moiety to increase the stability or pharmacokinetic and/or pharmacodynamic properties of the antigen-specific $V_H$ binding domain (Sung et al., (2003) *J. Interferon Cytokine Res.*, 23 (1): 25-36). Alternatively, the effector moiety may be a PEGylated structure or a naturally glycosylated structure so as to improve pharmacodynamic properties.

The effector moiety may be peptide bonded to the antigen-specific $V_H$ binding domain or it may be chemically bonded to the antigen-specific heavy $V_H$ domain, for example by using a chemical linking structure such as a maleimide linker. Alternatively, the polypeptide complexes of the invention may be expressed as fusion proteins. As such, the present invention also encompasses a polynucleotide sequence consisting of the heterologous heavy chain locus, or an isolated polynucleotide encoding the heavy chain-only antibody, of the present invention wherein the polynucleotide further comprises, in reading frame, one or more exon(s) encoding an effector moiety. This exon may be at the 5' or 3' end of the polynucleotide. For example, the polynucleotide may comprise, in the following order and in reading frame, a $V_H$ and a binding domain\effector moiety gene segment.

In the case of genetic fusions, the attachment of the various domains may be achieved using a recombinant DNA construct that encodes the amino acid sequence of the fusion protein, with the DNA encoding the various domains placed in the same reading frame. Such constructs are of value as diagnostics and therapeutics. As diagnostics, the effector domain can be a fluorescent protein (eg GFP) or enzyme (eg β-gal). Alternatively, the effector domain can be a tag for enhanced binding to a substrate (eg polyhistidine or a biotin), an antigen to provide a site of attachment for secondary antibodies or a leucine zipper or similar binding motif which may serve as a site for the attachment of fluorescent markers.

Polypeptide Complexes

The present inventors have also realised that it is possible to produce a bi-valent or multi-valent polypeptide complex comprising at least part of an antibody heavy chain, alone or in combination with a separate effector (light) chain comprising a complementary assembly domain and having additional effector activity. Polypeptide complexes according to the present invention retain the physiological function conferred by the heavy chain constant region in combination with additional effector moiety functions associated with the effector chain (FIG. 3).

As such, in a third aspect, the polypeptide complex comprises heavy chains in combination with one or more effector chains (light chains). The second aspect of the present invention provides a polypeptide complex comprising a pair of heavy chains and a pair of effector chains, wherein:

the pair of heavy chains are associated with each other;
one of the effector chains is associated with one of the heavy chains and the other of the effector chains is associated with the other of the heavy chains;
each heavy chain comprises a binding domain, a dimerization domain, preferably comprising at least $C_H2$, $C_H3$ and, optionally, $C_H4$ constant region domains, and an effector moiety capable of binding to a complementary assembly domain of the effector chain; and
the effector chain comprises a complementary assembly domain having attached to it an effector moiety,
wherein the assembly domain and the complementary assembly domain associate with one another through non-covalent interactions.

Preferably, the effector moiety in the heavy chain is different to the effector moiety in the effector chain.

Optionally, the polypeptide complex includes a flexible hinge-like domain at the carboxyl terminus of the $C_H3$ domain (or $C_H4$ domain, if present) linking it to the assembly domain. Preferably, the polypeptide complex includes a natural hinge domain or a flexible engineered hinge-like domain between the binding domain and the $C_H2$ domain. The presence of hinge regions facilitates the independent function of binding domains and effector moieties in the resultant polypeptide complexes.

The effector moiety in the first polypeptide heavy chain optionally has a specificity different from the specificity of the effector moiety in the second polypeptide heavy chain.

According to the present invention, the effector moiety of the polypeptide complex may be replaced by a binding domain. Preferably, the binding domain comprises a $V_H$ domain (as defined in the first aspect of the invention) or a cell receptor binding domain. The resulting tetravalent dimeric binding protein (polypeptide complex) can comprise up to four different effector moieties. Preferably the effector moieties at the amino terminal end of the heavy chain are identical, and those at the carboxyl terminal end are identical (but recognise a different antigen or epitope to that at the amino terminal end), facilitating the assembly of a single homodimer. Such a molecule may prove advantageous for the capture of pathogens, effector functionality being provided by the inclusion of appropriate heavy chain functional domains (eg IgA or IgM).

An exemplary polypeptide complex according to the third aspect of the invention is useful for cytochemical labelling, targeting methods or therapy. For example if the effector molecule comprises an antigen-specific $V_H$ binding domain which targets a cancer cell surface marker and the effector moiety comprises a binding domain specific for a pro-drug converting enzyme (the effector chain). The antigen-specific $V_H$ binding domain binds to the target and brings the effector moiety into close proximity with the target such that on binding the effector chain it can exert a biological effect on the target in the presence of the pro-drug (eg nitroreductase with CB1954). The inclusion of immunoglobulin heavy chain effector function as the dimerisation domain may also be beneficial in elimination of the target cell.

The Effector Chain

The effector chain comprises a complementary binding domain and an effector moiety, which associates with a heavy chain through the heavy chain effector moiety to form the assembled polypeptide binding complex. The effector chain complementary assembly domain may be an integral component of the effector moiety or a protein or alternative ligand fused or chemically linked to the effector moiety. The heavy chains of the assembled polypeptide binding complex bind to the target and bring the effector (light) chain moiety into close proximity with the target such that it can exert a biological effect of the target.

The Effector Moiety

The term 'effector moiety' as used herein includes any moiety that mediates a desired biological effect on a cell. The effector domain may be a cell, for example a T-cell, a peptide, polypeptide or protein or may be a non-peptidic structure. For example, the effector domain may be an enzyme, drug, pro-drug, toxin, in particular a protein toxin, a radionuclide in a chelating structure or binding domain. The effector moiety associated with the complementary assembly domain maybe cellular, proteinaceous, organic or inorganic in nature, dependent on the desired effect.

The term 'binding domain' as used herein in respect of all the above aspects of the present invention includes any polypeptide domain that is active in a physiological medium. Such a binding domain must also have the ability to bind to a target under physiological conditions.

Such binding domains include domains that can mediate binding or adhesion to a cell surface. Suitable domains which may be used in the polypeptide complexes of the invention are mammalian, prokaryotic and viral cell adhesion molecules, cytokines, growth factors, receptor antagonists or agonists, ligands, cell surface receptors, regulatory factors, structural proteins and peptides, serum proteins, secreted proteins, plasmalemma-associated proteins, viral antigens, bacterial antigens, protozoal antigens, parasitic antigens, lipoproteins, glycoproteins, hormones, neurotransmitters, clotting factors, engineered single chain Fvs and the like. Preferably the binding domain is a vertebrate $V_H$ domain, more preferably a mammalian $V_H$ domain such as a human $V_H$ domain.

A binding domain may comprise a camelid $V_H$ ($V_{HH}$) domain or may comprise a $V_H$ domain obtained from a non-camelid. Preferably, the binding domain is a human $V_H$ domain. $V_H$ binding domains are preferably of B-cell origin derived from transgenic animals or camelids (as described above) as opposed to $V_H$ domains derived from synthetic phage libraries, since the former will be of higher affinity due to their generation in response to antigen challenge in vivo via VDJ rearrangement and somatic mutation.

If the effector moiety comprises a binding domain, it preferably has different specificity from the binding domain in the heavy chain. The advantage of this arrangement is that polypeptide complex can facilitate cross-linking of different targets or bind different antigens on a target cell (eg pathogen).

The binding domain in the first heavy chain may have a specificity different from that of the binding domain in the second heavy chain. In this way, the polypeptide complex will be at least bivalent and will be able to crosslink different targets and the effector domain will be able to exert its effect on both targets. A multivalent polypeptide complex can be created through the association of these tetravalent heavy chains with effector chains comprising effector domains with yet different specificity(ies) and functionality. Also, the effector moiety in the first heavy chain may have a different specificity from the effector moiety in the second heavy chain, permitting the capture of more than one effector chain, each carrying a different functionality.

The Complementary Assembly Domain Binds to an Effector Moiety

When a heavy chain associates with an effector chain, the terms 'effector moiety' and 'complementary assembly domain' as used herein include any moieties that can form at least a non-covalent attachment to each other. For example, the effector moiety and the complementary assembly domain may be a protein, peptide fragment or consensus sequence capable of forming a protein-protein interaction, such as that seen between: the $C_H1$ domain of an immunoglobulin heavy chain and the constant region of an immunoglobulin light chain; leucine zippers; VCAM and VLA-4; integrins and extracellular matrix proteins; integrins and cell surface molecules such as CD54 or CD102; ALCAMs and SRCR domains; an scFv and antigen or $V_H$ binding domain and antigen.

The Heavy Chains

Where the dimerization domains of the heavy chains comprise immunoglobulin heavy chain constant regions, the constant regions ($C_H$ exons) may give further physiological functionality to the polypeptide binding complex. In particular, the immunoglobulin heavy chain constant domains may provide for, inter alia, complement fixation, macrophage activation and binding to Fc receptors, depending on the class or subclass of the antibody constant domains.

As discussed above, it is well documented that the class of heavy chain expressed has a major role in effector function in vivo. An established cell line may produce a polypeptide complex having a useful targeting and biological effect but the heavy chain constant region may be of a class which is diagnostically or therapeutically undesirable, or it may not be secreted in useful quantities. Accordingly, the heavy chain constant domains of the polypeptide complexes of the invention may be specifically altered or partially or completely omitted to introduce or remove components of immunoglobulin heavy chains.

For instance, Ig molecules of class M are known to play an important role in the activation of macrophages and the complement pathway. Due to the close proximity of its binding sites, IgM has a high avidity for pathogens, including viruses. However, IgM is also known to be difficult for use in rapid immunoassay techniques whereas Ig of class G can be readily used in these techniques. For such uses, it would be useful to switch the class of the heavy chain from μ to γ domains.

The expression of the heavy chain Cγ locus alone will produce IgG, including IgG1, IgG2, IgG3 and IgG4 isotypes, some of which will also activate complement. IgG antibodies bind and activate macrophages and granulocytes, and can cross the placenta.

Additional applications of various antibody classes have been discussed previously.

The constant regions of the heavy chains of the polypeptide complexes of the present invention may be of human, rabbit, rat or mouse origin as herein defined. Preferably, they are of human origin.

The polypeptide complexes of the present invention can also be used solely to block binding of ligands to their receptors by using dimerisation domains which provide no effector functions. Multiple receptors can be blocked by a multi-specific polypeptide complex.

In a fourth aspect of the invention, the effector molecule may comprise a dimerization domain such that the effector molecule can associate with a separate effector molecule. This dimerization domain may comprise one or more of $C_H2$, $C_H3$ or $C_H4$ antibody constant region domains and/or a J chain. In this embodiment of the invention, two or more effector molecules may associate to produce an effector molecule dimer or multimer. The effector molecules may be the same (enabling the production of an effector molecule homodimer or homomultimer) or different (enabling the production of an effector molecule heterodimer or heteromultimer). Preferably, the effector molecule dimer or multimer is bi-valent or multi-valent. Preferably, the constant regions for the two or more effector molecules (ie the dimerization domains) are identical, thus reducing the possibility of product heterogeneity.

According to the fourth aspect of the present invention, there is provided a polypeptide complex comprising a dimer consisting of a first polypeptide heavy chain and a second polypeptide heavy chain wherein:

each polypeptide heavy chain comprises a binding domain and a dimerization domain which optionally comprises at least $C_H2$, $C_H3$ and, optionally, $C_H4$ antibody constant region domains; and, optionally, an effector moiety, wherein, preferably:

the binding domain in the first polypeptide heavy chain has the same specificity as the binding domain in the second polypeptide heavy chain; and the constant regions (dimerization domains) for the two polypeptide heavy chains are identical.

Preferably, the first and second chains have the same effector moiety.

Preferably, the dimerization domain comprises at least $C_H2$, $C_H3$ and, optionally, $C_H4$ antibody constant region domains The fourth aspect of the present invention also provides a polypeptide complex comprising a plurality of polypeptide heavy chain dimers and a J chain, wherein:

the plurality of polypeptide heavy chain dimers are assembled by the J chain;

each polypeptide heavy chain comprises a binding domain and identical μ, ε, α or γ $C_H2$, $C_H3$ and, optionally, $C_H4$ domains; and there is at least two binding domains having different specificities in the polypeptide complex (see FIGS. 4 and 5).

As defined for the first aspect of the invention above, each heavy chain constant region preferably comprises at least one heavy chain constant region gene, which is expressed without a functional $C_H1$ domain so that generation of heavy chain-only antibody can occur. Each heavy chain constant region may also comprise one or more additional heavy chain constant region genes, which are selected from the group consisting of Cδ, $Cγ_{1-4}$, Cμ, Cε and $Cα_{1-2}$ with the proviso that the additional heavy chain constant region genes also do not express a functional $C_H1$ domain. The heavy chain constant region genes are selected depending on the preferred class or mixture of antibody classes required.

Preferably, there are only two binding domains of different specificities in expressed IgA and IgM.

In one embodiment, the heavy chains each include a $C_H4$ domain, the constant domains are α domains and the polypeptide complex includes a J chain.

In another embodiment, the heavy chains each include a $C_H4$ domain, the constant domains are α domains and the antibody includes a J chain.

Assembly of the Polypeptide Complex

The modular domain arrangement of the polypeptide complexes of the present invention enables them to be constructed in a large number of possible permutations. Such alterations in the domain architecture and amino acid sequence of the polypeptide complex may be achieved by suitable mutation or partial synthesis and replacement of appropriate regions of the corresponding DNA coding sequences. Substitute or additional domains may be obtained from compatible recombinant DNA sequences. For example, the heavy chains may include a natural hinge or engineered flexible polypeptide domain both between the binding domain and the amino terminus of the $C_H2$ domain and between the effector domain and the C-terminal end of the heavy chain ($C_H3$ or $C_H4$).

The heavy chains in the polypeptide complex of the invention are expressed as fusion proteins. The effector chains in the polypeptide complex of this aspect of the invention may be expressed as fusion proteins or may be assembled by chemical means or, if cellular in nature, may be isolated from blood or tissue, or captured in vivo (for example albumin).

In the case of genetic fusions, the attachment of the various domains may be achieved using a recombinant DNA construct that encodes the amino acid sequence of the fusion protein, with the DNA encoding the various domains placed in the same reading frame.

The effector moiety, if present as part of a fusion protein, may be located at either the amino or carboxy terminus of the complementary assembly domain.

Alternatively, the domains in the effector chain may be assembled by normal peptide chemical methods, as already known in the art, rather than by being synthesised as a fusion protein.

Linkage may be through a peptide bond or through chemical linkage. For example, the effector moiety may be peptide bonded to the complementary assembly domain or it may be chemically bonded to the complementary assembly domain, for example by using a chemical linking structure such as a maleimide linker.

The effector moiety may be positioned at any location in the heavy chain. For example, the effector moiety may be situated at the C terminal end of the heavy chain or between the binding domain and either the $C_H2$ domain or the hinge domain of the polypeptide complex. It is preferred that the assembly domain is not situated between the $C_H2$ and $C_H3$ domains as this might interfere with an effector function and the dimerization domains. Preferably the effector moiety is attached to the amino terminal or carboxy end of the heavy chain via a peptidic flexible linker or hinge like region so as to facilitate independent binding/function of effector moieties.

Polynucleotide Sequences, Vectors and Host Cells

The present invention also provides a polynucleotide sequence encoding a heavy chain of any one of the polypeptide complexes of the present invention, a vector comprising one or more of the polynucleotide sequences referred to above and a host cell transformed with a vector encoding the heavy chain of a polypeptide complex of the present invention. The polynucleotides preferably include sequences which allow the expressed heavy chains to be secreted as homodimers into the medium in which the host cell is growing. The host cell may be of any origin, including baterial and yeast cells, but is preferably a vertebrate host cell, more preferable a mammalian host cell.

Transfection of the same host cell with a second vector encoding a heavy chain comprising a binding domain with specificity for a different target results in co-expression of the two constructs and the assembly of a mixture of homodimers and heterodimers. Homodimers will show specificity to the cognate antigen and heterodimers will bind both antigens.

The present invention also provides a host cell transformed with a vector encoding at least one effector chain of a polypeptide complex of the present invention. The host cell may be of any origin, including a bacterial or yeast cell, but is preferably a vertebrate host cell, more preferably a mammalian host cell. Alternatively the effector chain may be synthesised using methods which are known in the art.

The present invention also provides a host cell transformed with a vector encoding at least one heavy chain of a polypeptide complex of the present invention. The host cell may be of any origin, including a bacterial or yeast cell, but is preferably a vertebrate host cell, more preferable a mammalian host cell. Alternatively the heavy chain may be synthesised using methods which are known in the art.

The present invention also provides a host cell transformed with a vector encoding at least one heavy chain and at least one effector chain of a polypeptide complex of the present invention. The host cell may be of any origin, including a bacterial or yeast cell, but is preferably a vertebrate host cell, more preferable a mammalian host cell. Alternatively the chains may be synthesised independently and assembled using methods which are known in the art.

Furthermore, the present invention provides a transgenic organism expressing at least one heavy chain homo- or hetero-dimer polypeptide complex of the present invention. The transgenic organism maybe a non-human vertebrate or mammal, a plant or an insect.

The present invention also provides a method for the production of class-specific heavy chain-only antibodies and VH domains thereof, according to the first aspect of the invention, by immunising a transgenic organism of the present invention with an antigen.

In a preferred embodiment of this aspect of the invention, the organism is a mouse.

The production of antibodies and polypeptide complexes for healthcare applications requires large scale manufacturing systems, examples of which are discussed in detail above. Such systems include plants (e.g. maize), transgenic cattle and sheep, chickens and insect larvae suitable for mass rearing technology. Other production systems, including virus infection (eg baculovirus in insect larvae and cell-lines) as an alternative to cell culture and germline approaches will also be familiar to those skilled in the art.

These methods, and other suitable methods known in the art, can be used for the production of the polypeptide binding complexes of the invention. Production of homodimers and/or of heterodimers can be achieved using these methods.

Uses of the Heavy chain-Only Antibodies and Polypeptide Complexes of the Invention The heavy chain-only antibodies and polypeptide binding complexes of the invention have a great number of applications.

For example, the heavy chain-only antibodies and polypeptide complexes of the invention comprise bi- and multi-specific polypeptide complexes. These complexes are particularly advantageous, eg as therapeutics for the treatment and prevention of infectious diseases.

The heavy chain-only antibodies and polypeptide binding complexes of the invention are useful for cytochemical labelling, targeting methods, therapy and diagnostics.

In mono-antibody therapy, pathogen escape, for example due to a mutation leading to loss of a single binding site, will abolish the therapeutic effect of the antibody. The production of heterodimer polypeptide complexes recognising different antigens on the same pathogen can overcome this problem. The use of at least two binding domains having different specificities in the polypeptide complexes of the invention can also be utilised to enhance both cell-cell interactions and cell/pathogen interactions.

In this embodiment, the polypeptide complexes of the invention can be utilised, for example, to bridge polypeptide complexes between two cell types such as a pathogen and a macrophage, or a tumour cell and a T-cell. Alternatively the polypeptide complex may recognise two or more epitopes on the same pathogen with effector function being provided by the heavy chain constant region alone.

Alternatively, bi-specific polypeptide binding complexes may be used to target cells and tissues in vivo, then subsequently to capture circulating effector molecules or imaging agents. For example bi-specific tumour targeting agents can be used to capture pro-drug converting complexes for the subsequent localised conversion of pro-drug to reactive agent. Bi- and multi-specific binding complexes in combination with effector agents may also be used to bind and destroy one or more pathogens dependent on the selection of binding domains. Alternatively the presence of two or more binding domains which recognise different antigens on the same pathogen provide clinical advantages and reduce the likelihood of pathogen escape and drug redundancy as a result of mutation within the pathogen.

The present invention provides heavy chain-only antibodies or fragments thereof according to the first aspect of the invention, polypeptide chains and complexes according to the second aspect of the invention; and effector chains and polypeptide complexes according to the third aspect of the invention. All are suitable for pharmaceutical use in humans, and so the invention provides a pharmaceutical composition comprising a heavy chain-only antibody, polypeptide chain, effector chain or polypeptide complex of the present invention. The invention also provides the use of a heavy chain-only antibody, a polypeptide chain, an effector chain or a polypeptide complex of the present invention in the preparation of a medicament for the prophylaxis and/or treatment of disease. Heavy and effector chains may be formulated together or separately, dependent on the manner of administration and action of the medicament.

The pharmaceutical compositions and medicaments will typically be formulated before administration to patients.

For example, the heavy chain-only antibodies or polypeptide complexes may be mixed with stabilisers, particularly if they are to be lyophilised. Addition of sugars (eg mannitol, sucrose, or trehalose) is typical to give stability during lyophilisation, and a preferred stabiliser is mannitol. Human serum albumin (preferably recombinant) can also be added as a stabiliser. Mixtures of sugars can also be used, eg sucrose and mannitol, trehalose and mannitol, etc.

Buffer may be added to the composition, eg a Tris buffer, a histidine buffer, a glycine buffer or, preferably, a phosphate buffer (eg containing sodium dihydrogen phosphate and disodium hydrogen phosphate). Addition of buffer to give a pH between 7.2 and 7.8 is preferred, and in particular a pH of about 7.5.

For reconstitution after lyophilisation, sterile water for injection may be used. It is also possible to reconstitute a lyophilised cake with an aqueous composition comprising human serum albumin (preferably recombinant).

Generally, the heavy chain-only antibodies and polypeptide complexes will be utilised in purified form together with pharmacologically appropriate carriers.

The invention thus provides a method for treating a patient, comprising administering a pharmaceutical composition of the invention to the patient. The patient is preferably a human, and may be a child (eg a toddler or infant), a teenager or an adult, but will generally be an adult.

The invention also provides heavy chain-only antibodies, polypeptide chains, effector chains or a polypeptide complex of the invention for use as a medicament.

The invention also provides the use of the heavy chain-only antibodies, polypeptide chains, effector chains or chain polypeptide complexes of the invention in the manufacture of a medicament for treating a patient.

These uses, methods and medicaments are preferably for the treatment of one of the following diseases or disorders: wound healing, cell proliferative disorders, including neoplasm, melanoma, lung, colorectal, osteosarcoma, rectal, ovarian, sarcoma, cervical, oesophageal, breast, pancreas, bladder, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, immunodisorders and organ transplant rejection; cardiovascular and vascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection, pathological conditions associated with the placenta and other pathological conditions and for use in immonotherapy.

In a further aspect still, the present invention provides the use of a heavy chain-only antibody or polypeptide binding complex of the present invention as a diagnostic, prognostic, or therapeutic imaging agent. Furthermore, the present invention provides the use of a heavy chain homo- or hetero-dimer of the present invention alone or in combination with one or more effector (light) chains of the present invention as a therapeutic imaging agent, a cytochemical reagent or diagnostic agent.

The present invention provides the use of a heavy chain-only antibody or a fragment thereof as herein described as an intracellular binding reagent, or an abzyme.

Preferred heavy chain-only antibody fragments are soluble antigen-specific VH binding domains.

The present invention also provides, the use of an antigen-specific single chain antibody or VH binding domain according to the present invention as an enzyme inhibitor or receptor blocker. Preferred heavy chain-only antibody fragments are soluble antigen-specific VH binding domains.

The present invention also provides the use of a $V_H$ domain fused to an effector molecule for use as a therapeutic, imaging agent, diagnostic, abzyme or reagent.

Flexible linkers (←) and hinge ( ( ) regions are indicated.

Figure 1:
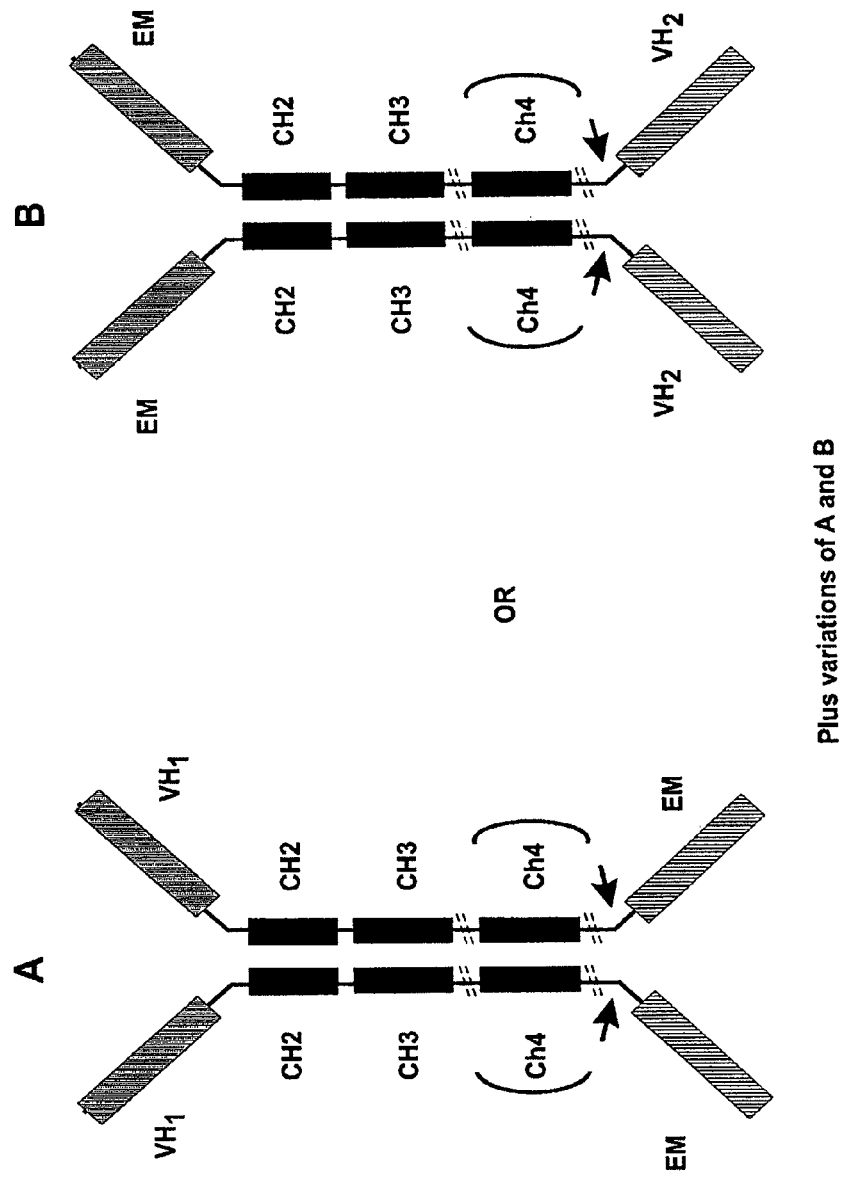
FIGS. 1A and 1B: shows a polypeptide complex comprising a binding domain ($V_H$) dimerization domain (optionally $C_H2$, $C_H3$ and $C_H4$) and a effector moiety (EM). Binding domains and effector moieties may be positioned at the amino or carboxy terminal ends of the dimerization domains.
Figure 2:
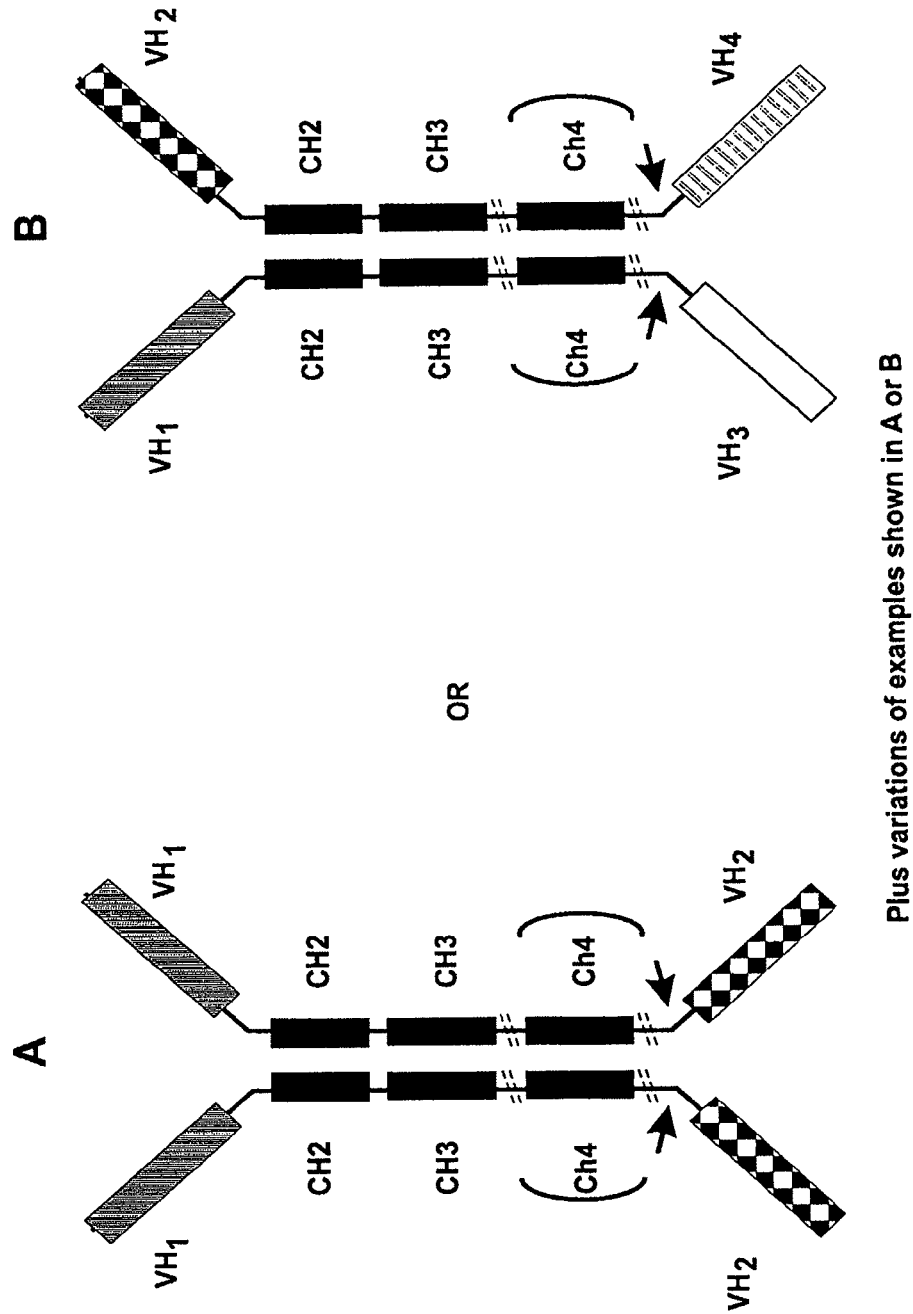

FIGS. 2A and 2B: shows different configurations of binding domains and the replacement of the effector moiety by further binding domains. A. Preferred option since homodimers are produced. No separation of products required. B. Mixture of homodimers and heterodimers are produced. Separation of products required.

Figure 3:
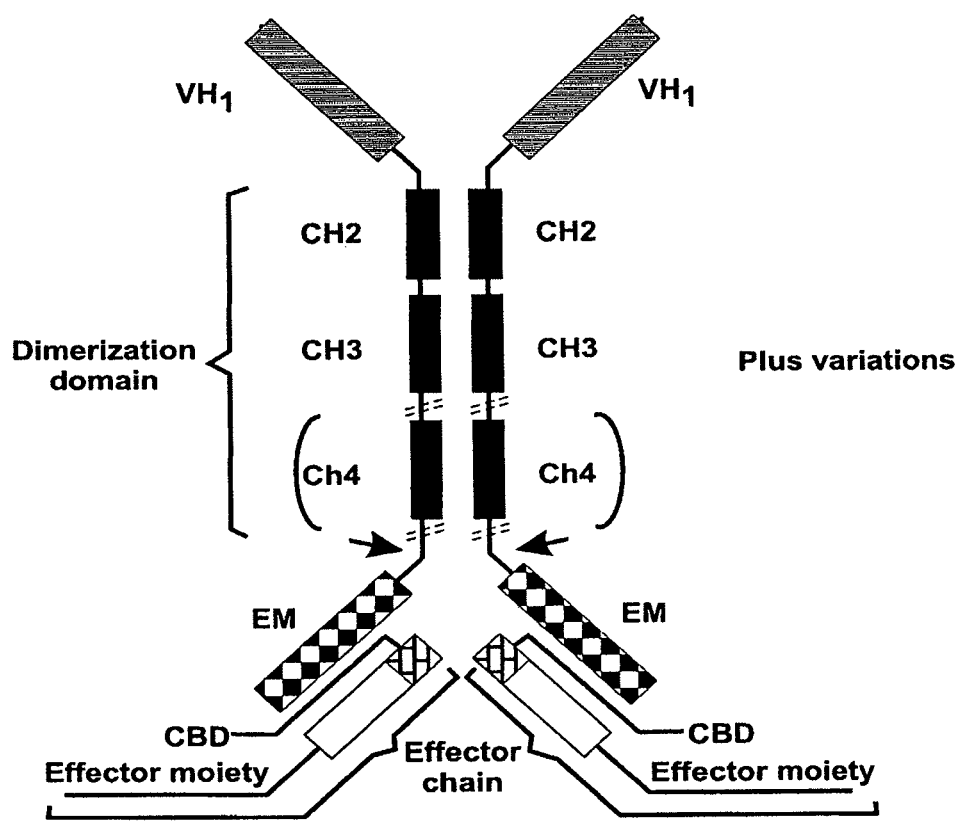

FIG. 3: shows a heavy chain polypeptide complex in association with an effector chain. The effector chain comprises a complementary binding domain (CBD) and an effector moiety (EM). CBD is recognised by EM of heavy chain. CBD is fused to or part of effector, e.g. enzyme, toxin, chelator, imaging agent. Effector chain can be synthesized separately from heavy chain.

Figure 4:
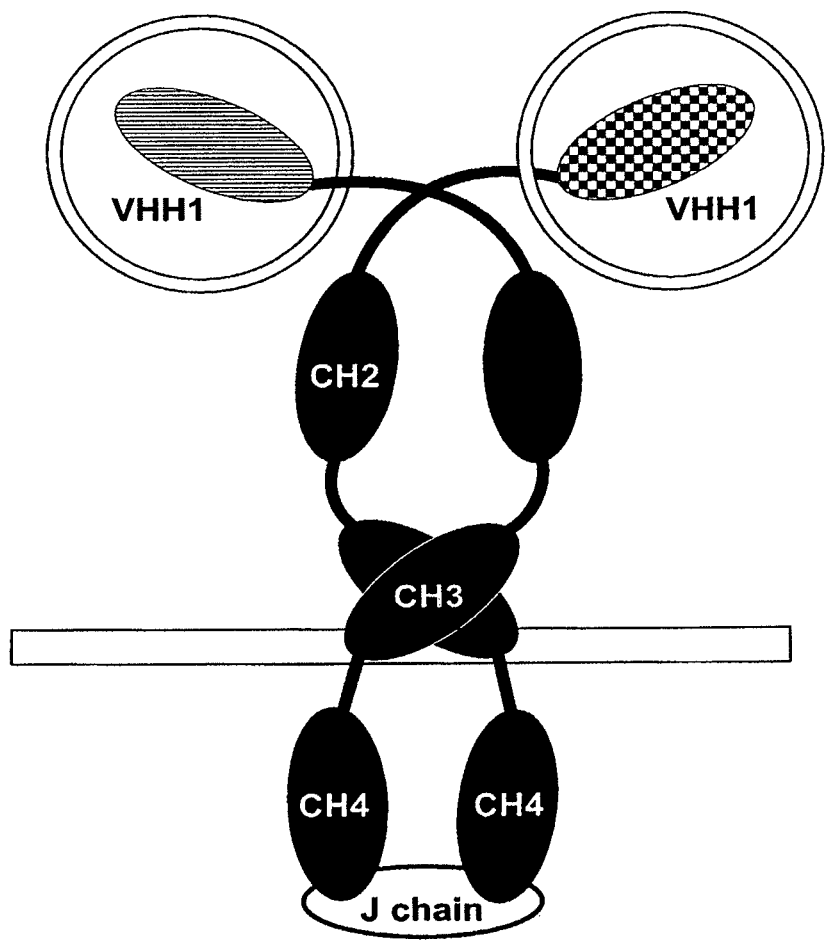

FIG. 4: shows a bivalent secretory IgA in association with a J chain.

Figure 5:
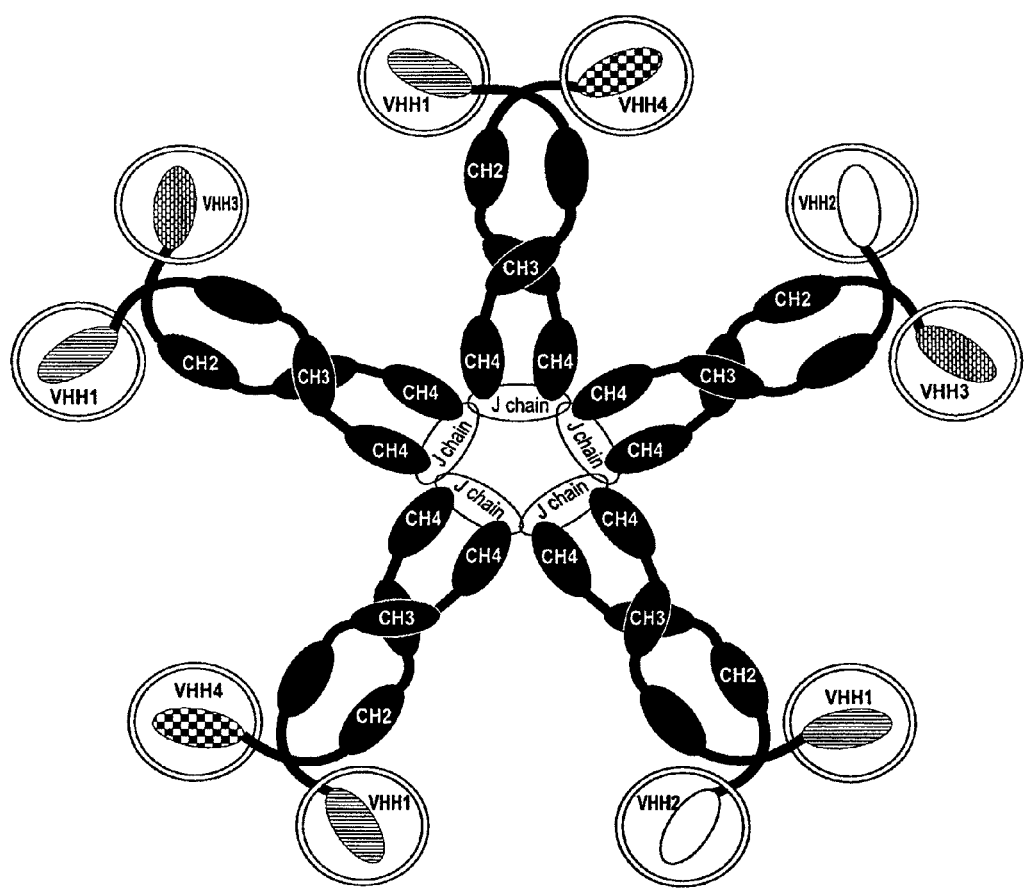

FIG. 5: shows a multivalent heavy chain-only IgM-like polypeptide complex assembled via a J chain.

Figure 6:
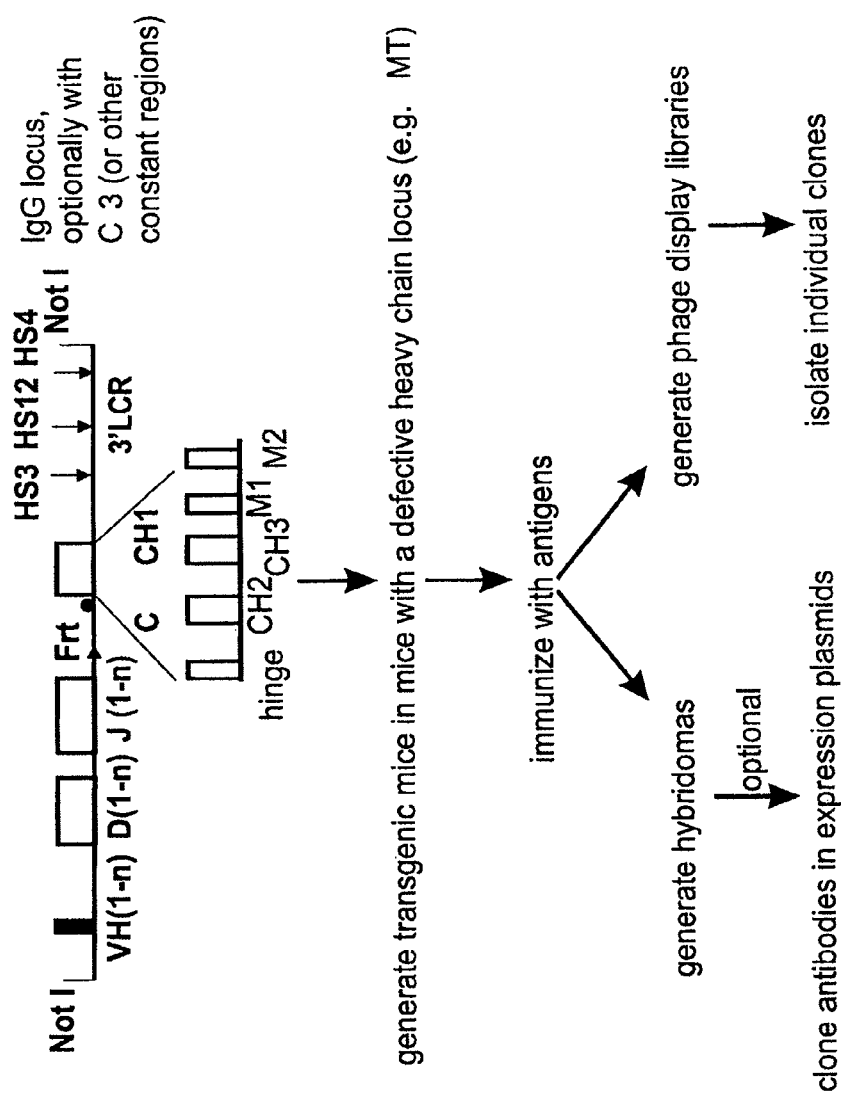

FIG. 6: shows the strategy for the generation of transgenic mice expressing an IgG locus and the functional generation of heavy chain-only antibodies and VH domains as a result of antigen challenge.

FIG. 7: shows the strategy for the generation of transgenic mice expressing an IgM locus and the functional generation of heavy chain-only antibodies and VH domains as a result of antigen challenge.

FIG. 8: shows the strategy for the generation of transgenic mice expressing an IgA locus and the functional generation of heavy chain-only antibodies and VH domains as a result of antigen challenge.

FIG. 9: Sequence alignment of the PCR products obtained from bone marrow cDNA using $V_{HH}1$ and $V_{HH}2$ primers in combination with human $C\gamma_2$ primer from mice containing a locus with constant regions that have a camelid splice mutation to remove CH1 (SEQ ID NOs:12-16). The results show that CH1 is not removed.

FIGS. 10-13: Structure of VH/camelid VH (VHH) constructs. 1-n stands for any number of VH genes, or D or J segments. The normal complement of the human locus is 51 V genes, 25 functional D segments (plus 2 non functional ones) and 6 J segments. In case of a Cµ (for IgM) or Cε (for IgE) region there is no H region and there is an additional CH4 exon between CH3 and M1. The VH genes(s) have been mutated to provide solubility as described in the public domain The VH genes, D and J segments and C exons are preferably human, but could be from any other species including camelids. In the latter case the camelid VH (VHH) genes would not be mutated as they are naturally soluble.

Figure 14:
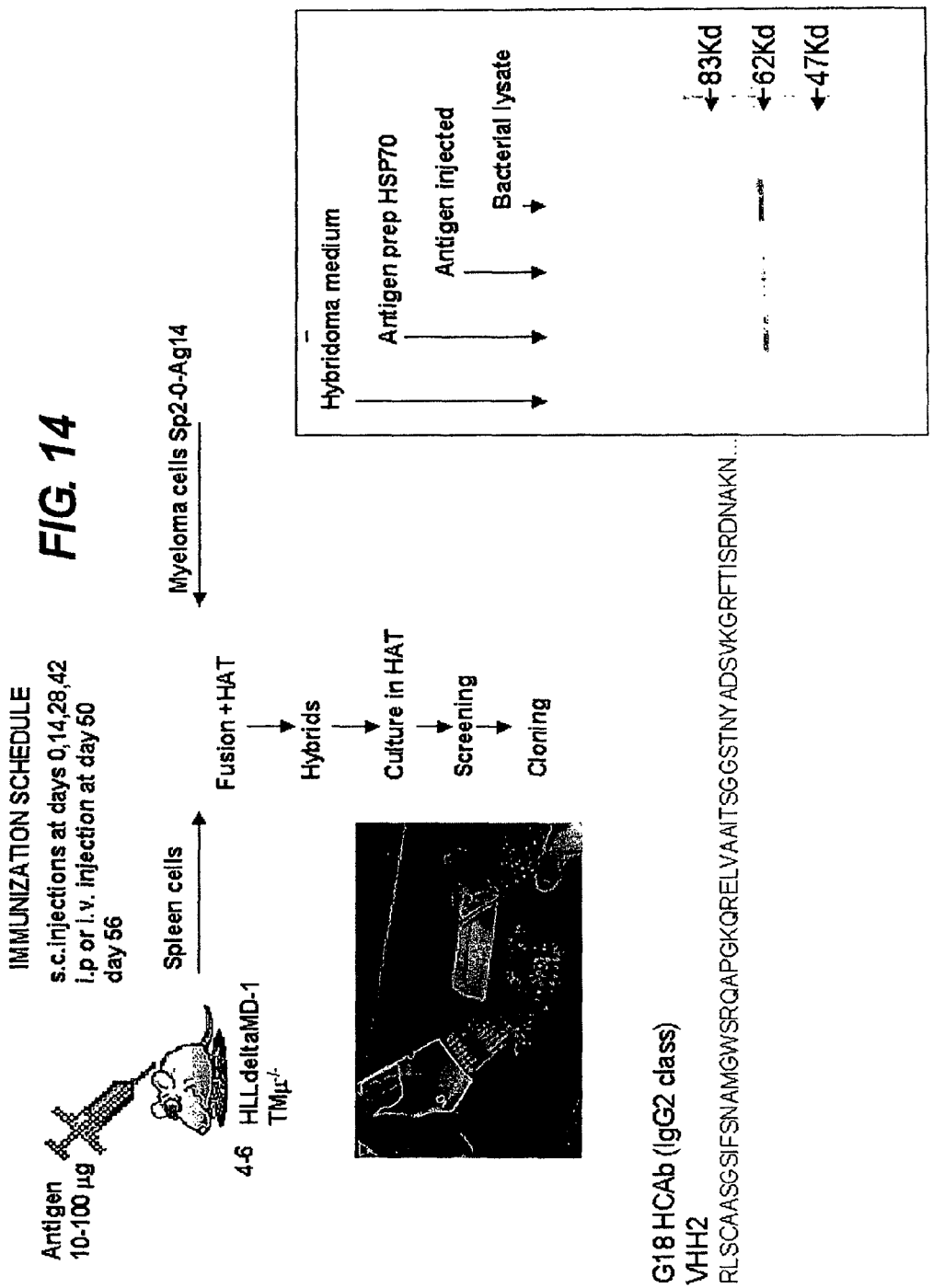

FIG. 14: Mouse immunization schedule and antibody assay for the generation of heavy chain-only IgG against *E. coli* HSP70 (SEQ ID NO:35).

Figure 15:
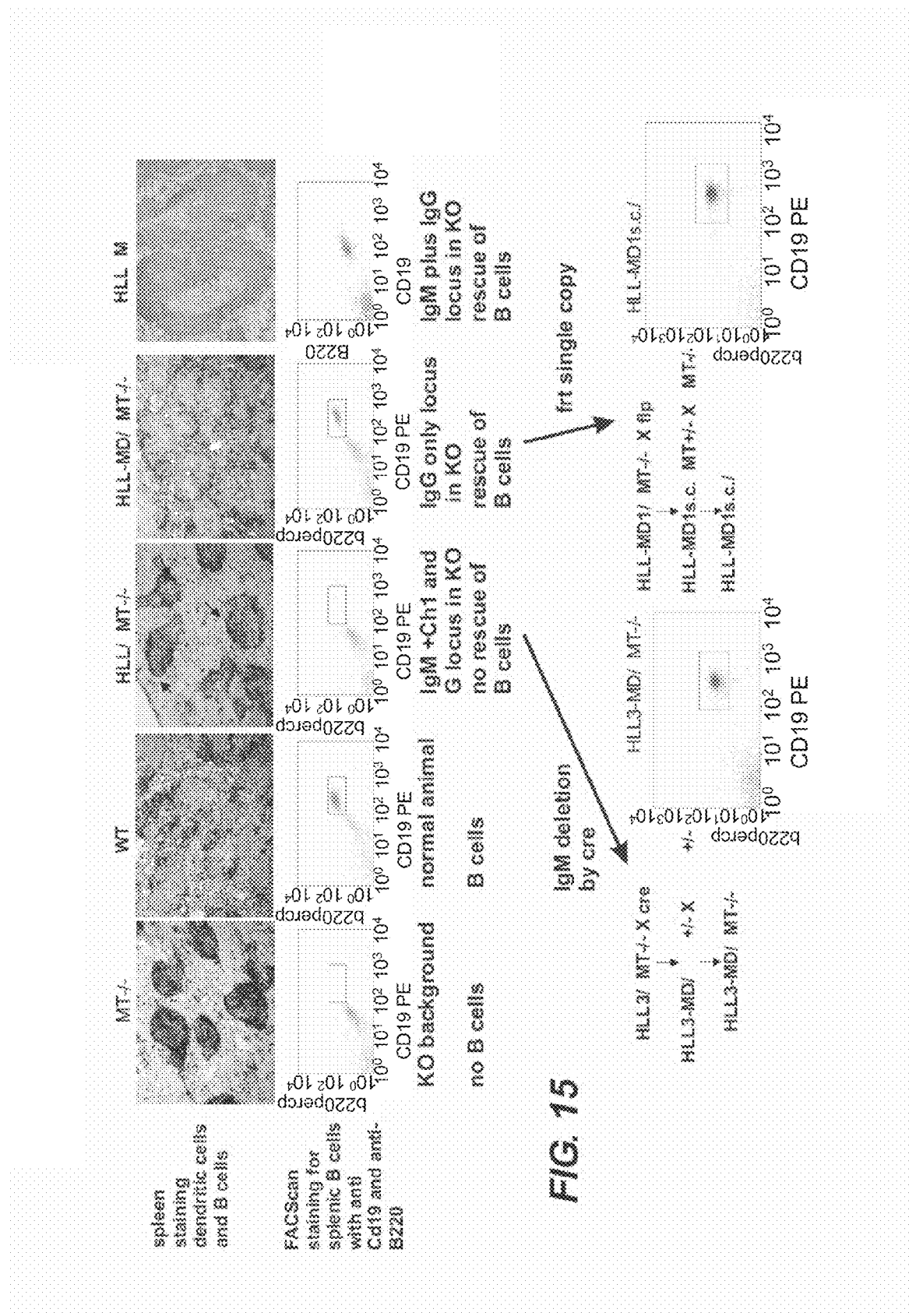

FIG. 15: Flow cytometric analysis and immunohistochemistry results for spleen cells derived from transgenic mice.

FIG. 16: Results of ELISA analysis of DKTP immunized transgenic mice and sequence analysis of resulting antibody library (SEQ ID NOs:17-21).

Figure 17:
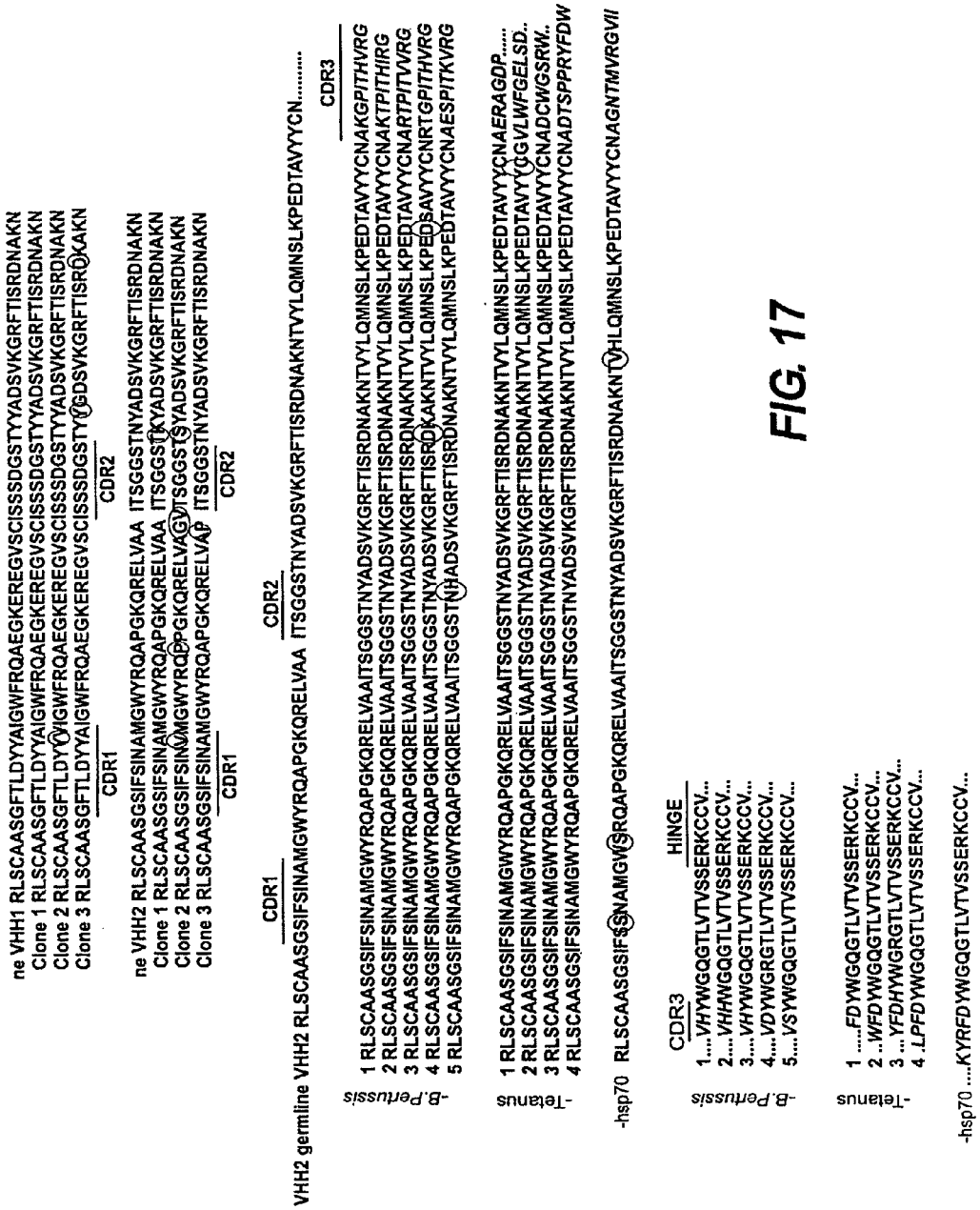

FIG. 17: Examples of somatic mutations and VDJ rearrangement seen in immunized transgenic mice (SEQ ID NOs: 22-29, SEQ ID NO:30, SEQ ID NOs:17-21 and SEQ ID NOs:31-A4

FIG. 18: Results of immunostaining assay on Tet-on cell line transfected with response plasmid containing A5 antibody.

Figure 19:
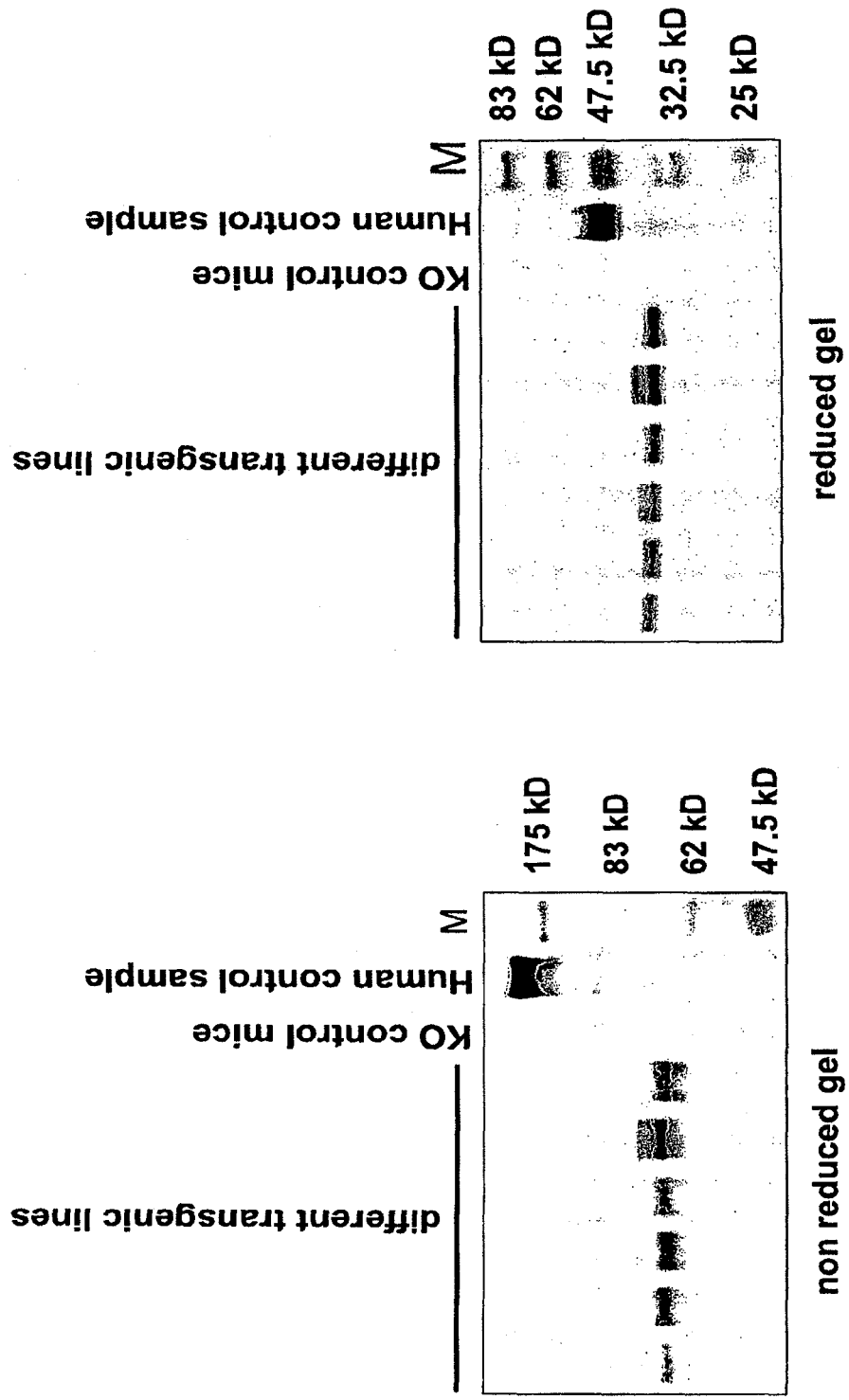

FIG. 19: Results of Western bolt analysis of sera of transgenic mouse lines.

Figure 20:
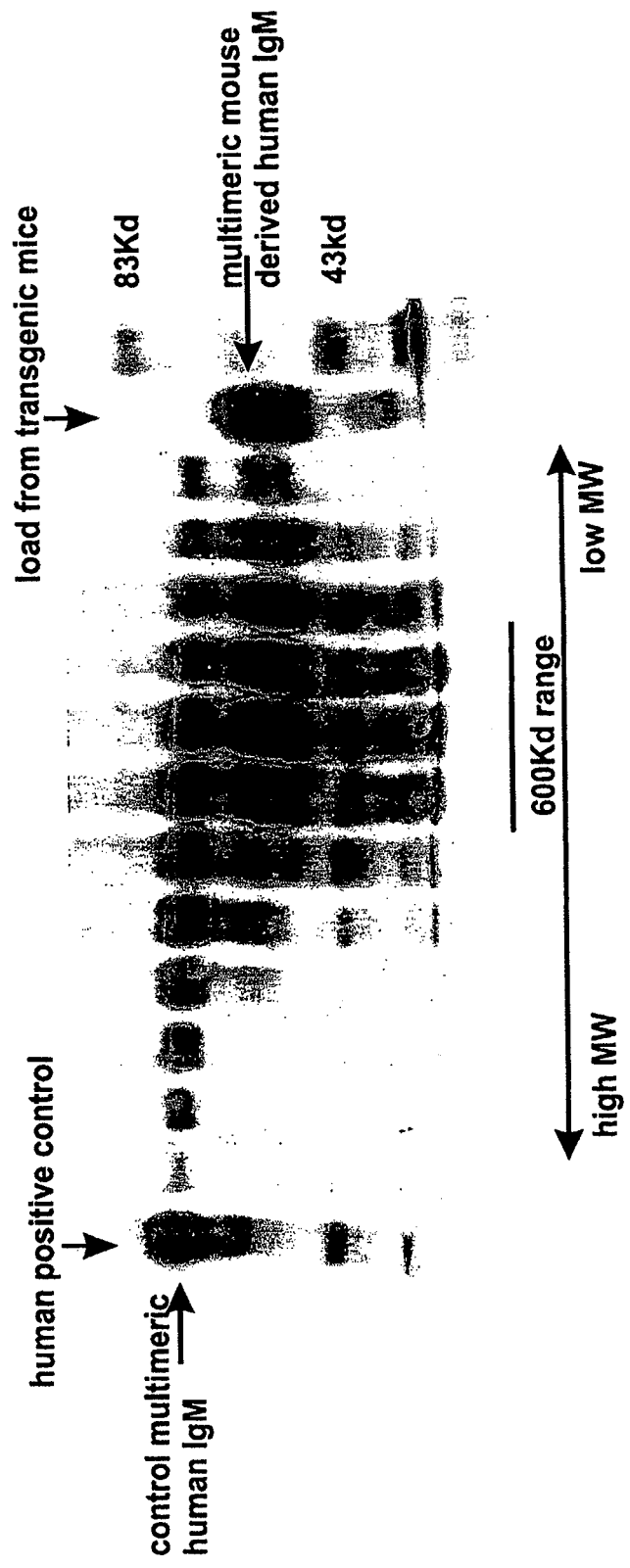

FIG. 20: Size fractionation of human IgM mixed with human single chain IgM produced by the IgM plus IgG locus mice.

Figure 21:
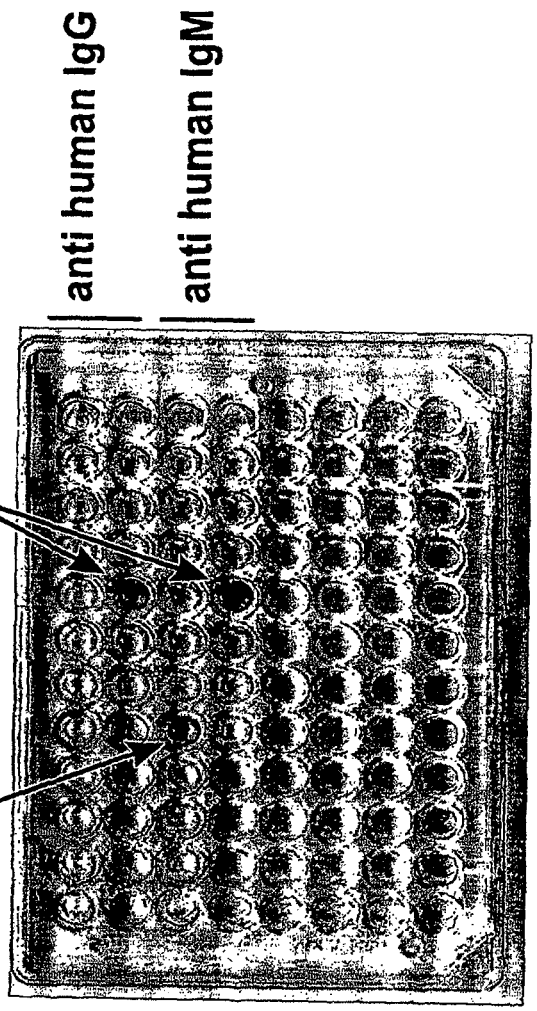

FIG. 21: Results of ELISA analysis of single chain IgM and IgG antibodies raised against human TNFα.

Figure 22:
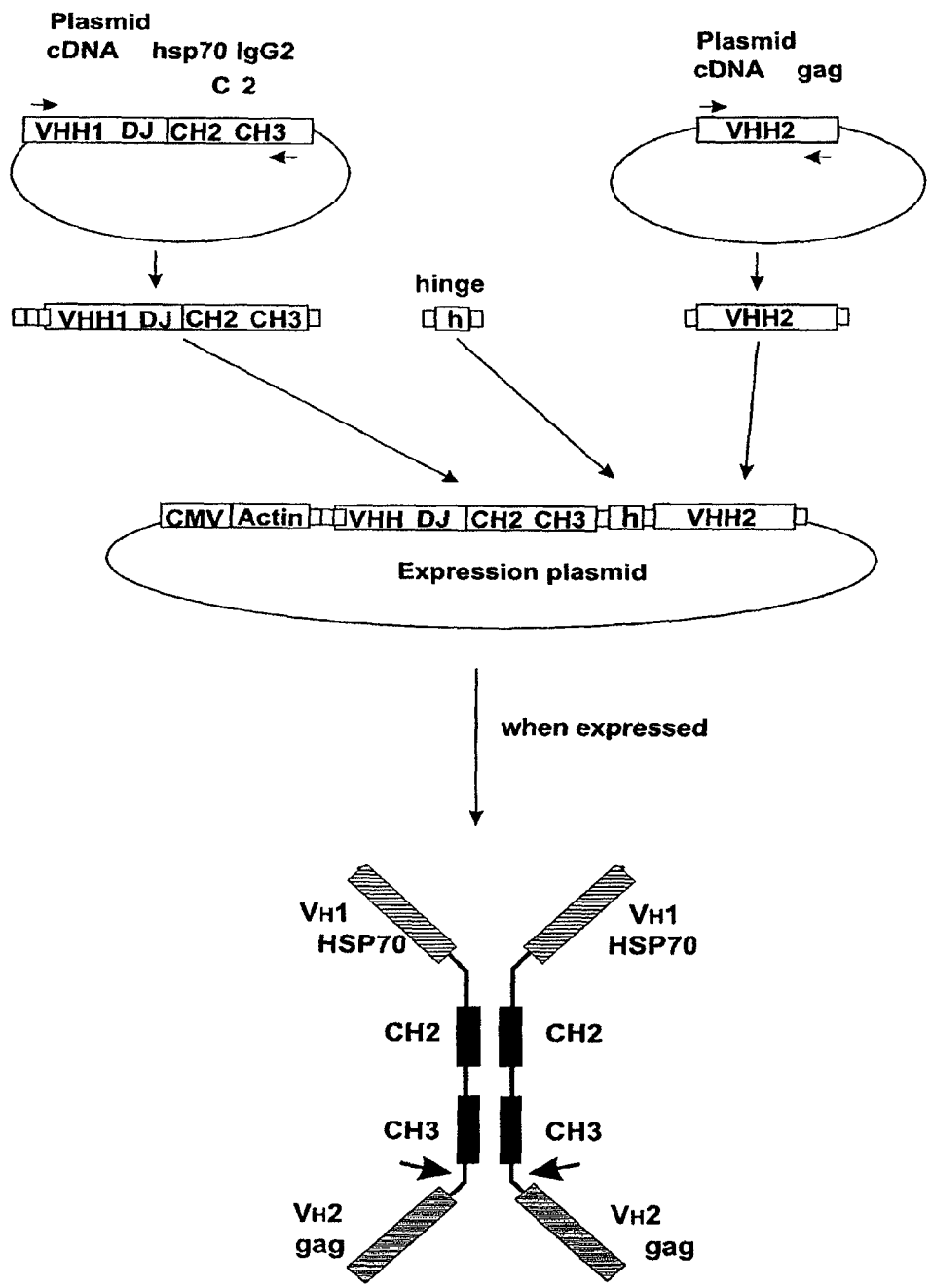

FIG. 22: shows a strategy for the generation of a homodimer plasmid with binding affinity for HSP70 and αGAG.

Figure 23:
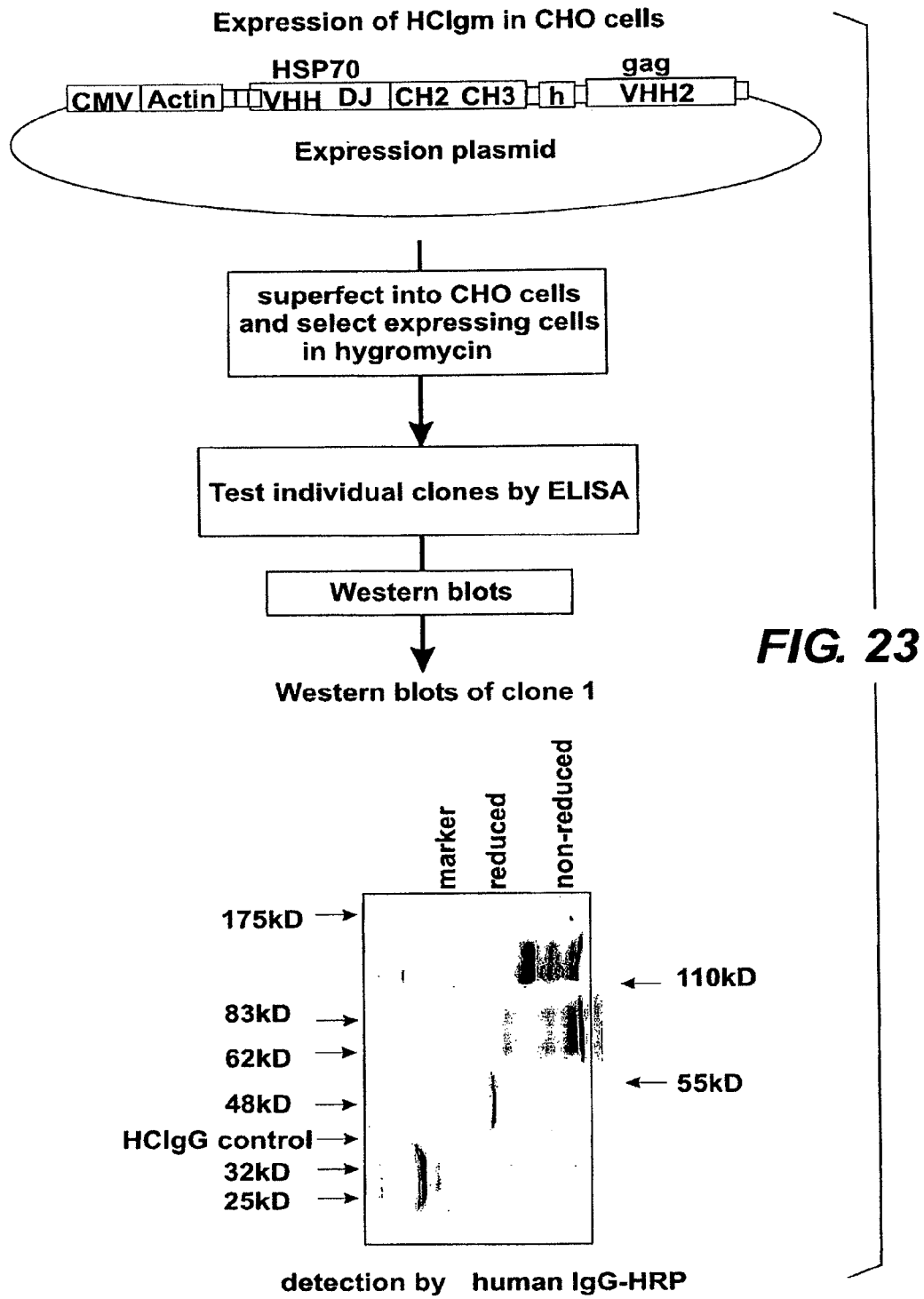

FIG. 23: Functional expression of homodimer polypeptide complex in CHO cells.

Figure 24:
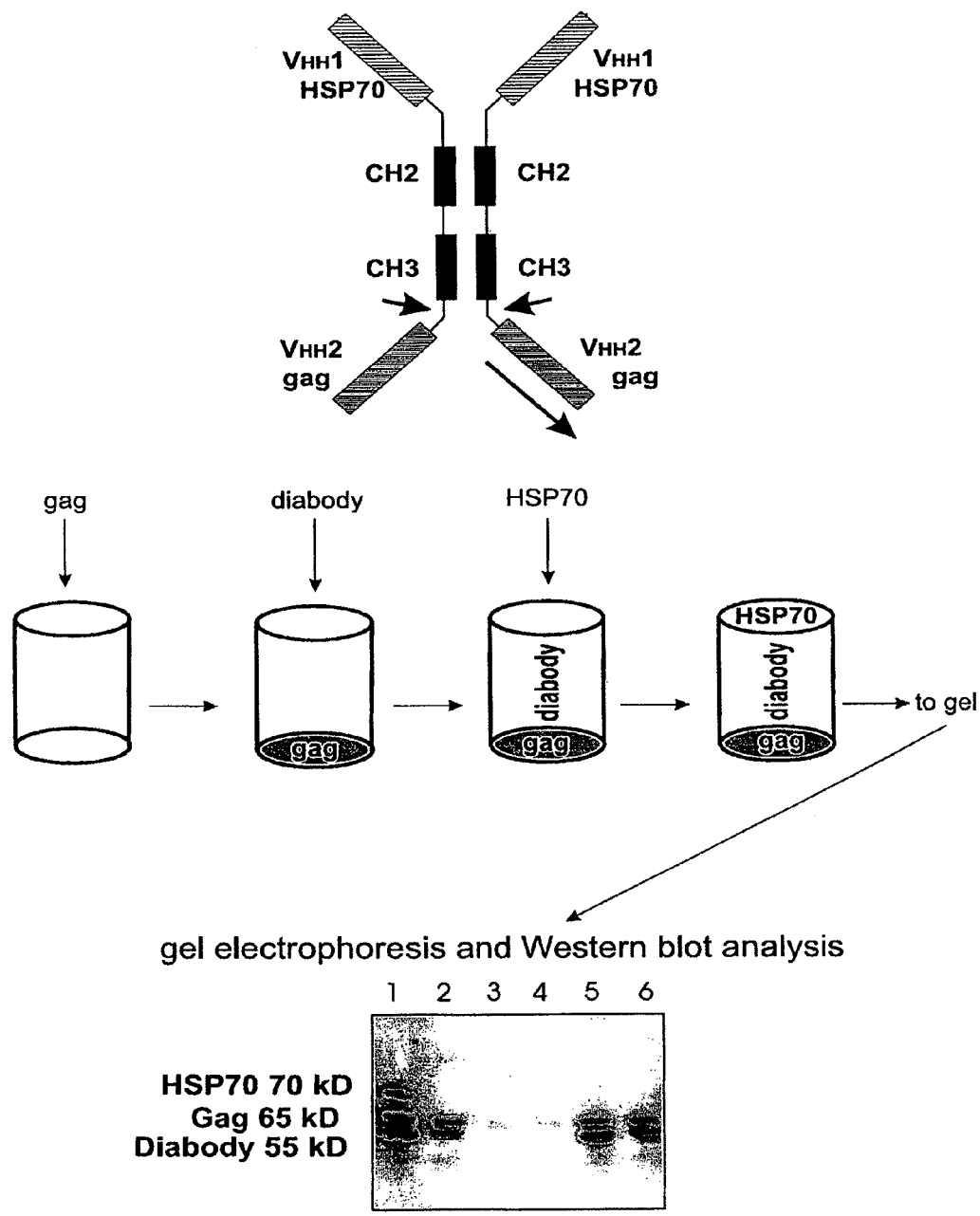

FIG. 24: demonstrates functional binding and simultaneous of homodimer polypeptide complex to alpha αGAG and HSP70. Schematic representation of a bivalent, bi-specific antibody. A second variable region (VHH2 directed against gag) is cloned onto the carboxyterminal end of a heavy chain only antibody containing the other specificity (VHH1 directed against HSP70). The hinge region between CH3 and VHH2 has been replaced by a linker region where all cysteines have been replaced by prolines (arrows). Coat ELISA plate with Gag, block with 1% milk/1% BSA in PBS, incubate first with diabody medium (1:2 dil.) and then with BI21 cell lysate (contains HSP70) (1:2 dil.). Elute bound proteins with sample buffer=2-mercaptoethanol and run on 8% gel. Stain with poly/monoclonal antibodies against Gag, diabody and HSP70. α Gag: Rabbit polyclonal/Swine α rabbit-AP (blue). α HSP70: monoclonal/Goat α Human IgG-HRP (brown). α Diabody: Goat α Human IgG-HRP (brown). Lane 1: Gag/Diabody/BI21 cell lysate. Lane 2: Gag/culture medium (is Diabody negative control)/BI21. Lane 3: -milk-BSA/Diabody/BI21. Lane 4: -milk-BSA/culture medium/BI21. Lane 5: Gag/Diabody/-milk-BSA. Lane 6: Gag/culture medium/-milk-BSA FIG. 25: shows the strategy for the generation of homodimer polypeptide complexes, optionally in association with effector chains carrying IgA effector function FIG. 26: shows the strategy for the generation of homodimer polypeptide complexes, optionally in association with effector chains carrying IgA effector function.

GENERAL TECHNIQUES

Unless defined otherwise, all technical and scientific terms used herein have the same meaning as commonly understood by one of ordinary skill in the art (e.g. in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2nd Ed. (1989) Cold Spring Harbor Laboratory Press, Cold Spring Harbor, N.Y. and Ausubel et al., Short Protocols in Molecular Biology (1999) 4th Ed., John Wiley & Sons, Inc.) and chemical methods. In addition Harlow & Lane, A Laboratory Manual, Cold Spring Harbor, N.Y., is referred to for standard Immunological Techniques.

Any suitable recombinant DNA technique may be used in the production of the bi- and multi-valent polypeptide complexes, single heavy chain antibodies, and fragments thereof, of the present invention. Typical expression vectors, such as plasmids, are constructed comprising DNA sequences coding for each of the chains of the polypeptide complex or antibody. Any suitable established techniques for enzymic and chemical fragmentation of immunoglobulins and separation of resultant fragments may be used.

The present invention also provides vectors including constructs for the expression of heavy chain-only antibodies in transgenic mice and the construction and expression of polypeptide complaxes of the present invention.

It will be appreciated that a single vector may be constructed which contains the DNA sequences coding for more than one polypeptide chain. For instance, the DNA sequences encoding two different heavy chains may be inserted at different positions on the same plasmid.

Alternatively, the DNA sequence coding for each polypeptide chain, may be inserted individually into a plasmid, thus producing a number of constructed plasmids, each coding for a particular polypeptide chain. Preferably, the plasmids into which the sequences are inserted are compatible.

Each plasmid is then used to transform a host cell so that each host cell contains DNA sequences coding for each of the polypeptide chains in the polypeptide complex.

Suitable expression vectors which may be used for cloning in bacterial systems include plasmids, such as Col E1, pcR1, pBR322, pACYC 184 and RP4, phage DNA or derivatives of any of these.

For use in cloning in yeast systems, suitable expression vectors include plasmids based on a 2 micron origin.

Any plasmid containing an appropriate mammalian gene promoter sequence may be used in cloning in mammalian systems. Insect or bacculoviral promoter sequences may be used fir insect cell gene expression. Such vectors include plasmids derived from, for instance, pBR322, bovine papilloma virus, retroviruses, DNA viruses and vaccinia viruses.

Suitable host cells which may be used for expression of the polypeptide complex or antibody include bacteria, yeasts and eukaryotic cells, such as insect or mammalian cell lines, transgenic plants, insects, mammalian and other invertebrate or vertebrate expression systems.

Polypeptide Complexes and Single Heavy Chain Antibodies of the Present Invention It will be understood that term 'polypeptide complex', 'a single heavy chain antibody' and 'heterlogous heavy chain locus' of the present invention also include homologous polypeptide and nucleic acid sequences obtained from any source, for example related cellular homologues, homologues from other species and variants or derivatives thereof.

Thus, the present invention encompasses variants, homologues or derivatives of the polypeptide complexes and antibodies as herein described.

In the context of the present invention, a homologous sequence is taken to include an amino acid sequence which is at least 80, 85, 90, 95, 96, 97, 98, 99, 99.5, 99.6, 99.7, 99.8, 99.9% identical, preferably at least 98 or 99%, identical, at the amino acid level over at least 30, preferably 50, 70, 90 or 100 amino acids. Although homology can also be considered in terms of similarity (i.e. amino acid residues having similar chemical properties/functions), in the context of the present invention it is preferred to express homology in terms of sequence identity.

The present invention also includes constructed expression vectors and transformed host cells for use in producing the polypeptide complexes and antibodies of the present invention.

After expression of the individual chains in the same host cell, they may be recovered to provide the complete polypeptide complex or heavy chain-only antibody in active form.

It is envisaged that, in preferred forms of the invention, the individual heavy chains will be processed by the host cell to form the complete polypeptide complex or antibody which advantageously is secreted therefrom. Preferably, the effector chain is produced separately either by a host cell or by synthetic means.

Techniques for the preparation of recombinant antibody polypeptide complexes is described in the above references and also in, for example, EP-A-0 623 679; EP-A-0 368 684 and EP-A-0 436 597.

Immunisation of a Transgenic Organism

In a further aspect, the present invention provides a method for the production of the antibodies of the present invention comprising administering an antigen to a transgenic organism of the present invention.

The antibodies and polypeptide complexes produced from transgenic animals of the present invention include polyclonal and monoclonal antibodies and fragments thereof. If polyclonal antibodies are desired, the transgenic animal (e.g. mouse, rabbit, goat, horse, etc.) may be immunised with an antigen and serum from the immunised animal, collected and treated by known procedures. If serum containing polyclonal antibodies contains antibodies to other antigens, the polyclonal antibodies of interest can be purified by immunoaffinity chromatography and such like techniques which will be familiar to those skilled in the art. Techniques for producing and processing polyclonal antisera are also known in the art.

Uses of the Polypeptide Binding Complexes and Antibodies of the Present Invention The polypeptide complexes and antibodies including fragments thereof of the present invention may be employed in: in vivo therapeutic and prophylactic applications, in vitro and in vivo diagnostic applications, in vitro assay and reagent applications, and the like.

Therapeutic and prophylactic uses of the polypeptide complexes and antibodies of the invention involve the administration of the above to a recipient mammal, such as a human.

Substantially pure polypeptide complexes and antibodies including fragments thereof of at least 90 to 95% homogeneity are preferred for administration to a mammal, and 98 to 99% or more homogeneity is most preferred for pharmaceutical uses, especially when the mammal is a human. Once purified, partially or to homogeneity as desired, the polypeptide complexes and heavy-chain-only antibodies as herein described may be used diagnostically or therapeutically (including extracorporeally) or in developing and performing assay procedures using methods known to those skilled in the art.

Generally, the polypeptide complexes and antibodies of the present invention will be utilised in purified form together with pharmacologically appropriate carriers. Typically, these carriers include aqueous or alcoholic/aqueous solutions, emulsions or suspensions, which may include saline and/or buffered media. Parenteral vehicles include sodium chloride solution, Ringer's dextrose, dextrose and sodium chloride and lactated Ringer's.

Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The polypeptide complexes and antibodies, including fragments thereof, of the present invention may be used as separately administered compositions or in conjunction with other agents. These can include various immunotherapeutic drugs, such as cyclosporine, methotrexate, adriamycin, cisplatinum or an immunotoxin. Alternatively, the polypeptide complexes can be used in conjunction with enzymes for the conversion of pro-drugs at their site of action.

Pharmaceutical compositions can include "cocktails" of various cytotoxic or other agents in conjunction with the selected antibodies of the present invention or even combinations of the selected antibodies of the present invention.

The route of administration of pharmaceutical compositions of the invention may be any of those commonly known to those of ordinary skill in the art. For therapy, including without limitation immunotherapy, the polypeptide complexes or antibodies of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

The polypeptide complexes and antibodies of this invention can be lyophilised for storage and reconstituted in a suitable carrier prior to use. Known lyophilisation and reconstitution techniques can be employed. It will be appreciated by those skilled in the art that lyophilisation and reconstitution can lead to varying degrees of functional activity loss and that use levels may have to be adjusted upward to compensate.

In addition, the polypeptide complexes and antibodies of the present invention may be used for diagnostic purposes. For example, antibodies as herein described may be generated or raised against antigens which are specifically expressed during disease states or whose levels change during a given disease states.

For certain purposes, such as diagnostic or tracing purposes, labels may be added. Suitable labels include, but are not limited to, any of the following: radioactive labels, NMR spin labels and fluorescent labels. Means for the detection of the labels will be familiar to those skilled in the art.

The compositions containing the polypeptide complexes and antibodies of the present invention or a cocktail thereof can be administered for prophylactic and/or therapeutic treatments.

A composition containing one or more polypeptide complexes or antibodies of the present invention may be utilised in prophylactic and therapeutic settings to aid in the alteration, inactivation, killing or removal of a select target cell population in a mammal. In addition, the selected repertoires of polypeptide complexes and antibodies described herein may be used extracorporeally or in vitro selectively to kill, deplete or otherwise effectively remove a target cell population from a heterogeneous collection of cells.

Example 1

In preliminary experiments, transgenic mice were prepared to express a heavy chain locus wherein two llama VHH exons were linked to the human heavy chain diversity (D) and joining (J) segments, followed by the Cμ, Cδ, Cγ2, Cγ3 human constant region genes and human heavy chain immunoglobulin 3' LCR. The human Cγ2 and Cγ3 genes contained a G to A splice mutation. The presence of the Frt site enabled the generation of a single copy transgenic mouse from a multi-copy transgene array by Flp mediated recombination. However, sequences from the transgenic locus with a G to A splice mutation, showed aberrant splicing but incomplete CH1 removal (FIG. 9).
Constructs To overcome this problem, a genomic cosmid library was screened for clones containing the VH genes using standard methods. One (or more) different germline VHs were randomly chosen based on their sequence (five genera classes in the case of human VH's). Hydrophilic amino acid codons were introduced at positions 42, 49, 50 and 52 according to IMGT numbering (Lefranc et al. (1999)). The VH genes were combined into a BAC vector by standard procedures such as direct cloning using custom made linkers or homologous recombination.

Two clones were selected from the human genomic Pac library RPCI-11 (BACPAC Recource Center, USA): clone 1065 N8 containing human heavy chain D and J segments, Cμ (IgM) and Cδ (IgD) and clone 1115 N15 containing the Cγ3 (IgG3) genes. Bac clone 11771 from a different human genomic library (Incyte Genomics, CA, USA) was used as a source of Cγ2 (IgG2) gene and the immunoglobulin heavy chain LCR (Mills et al. (1997) *J. Exp Med.,* 15; 186(6):845-58).

Figure 10:
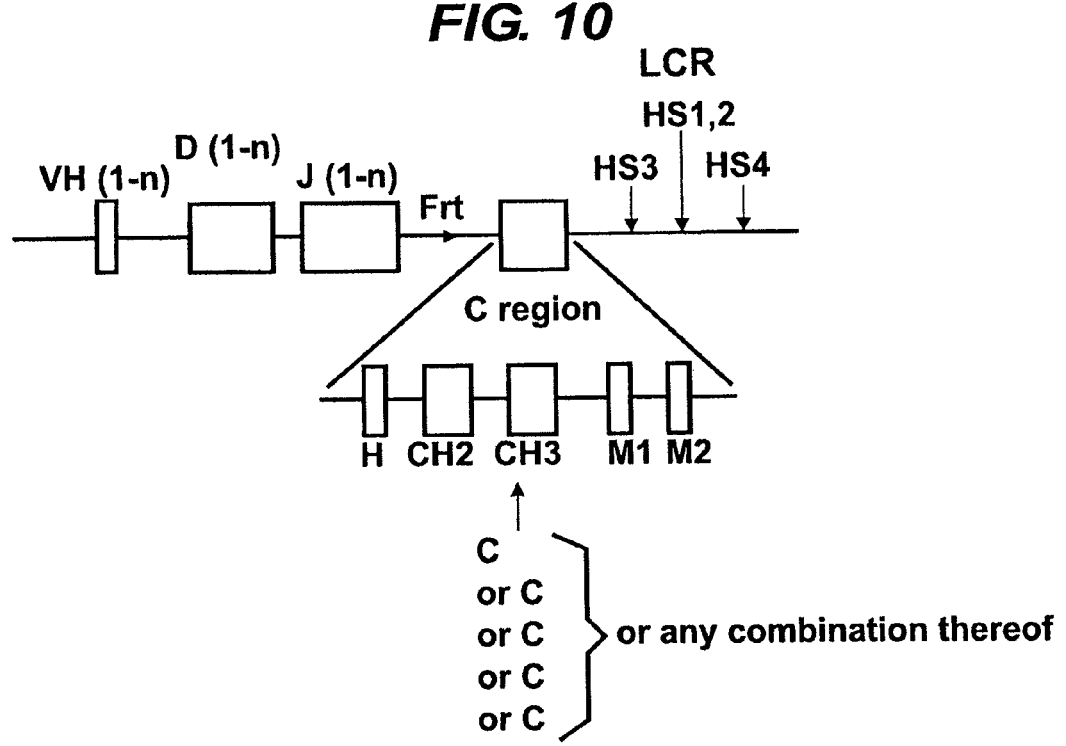
Figure 11:
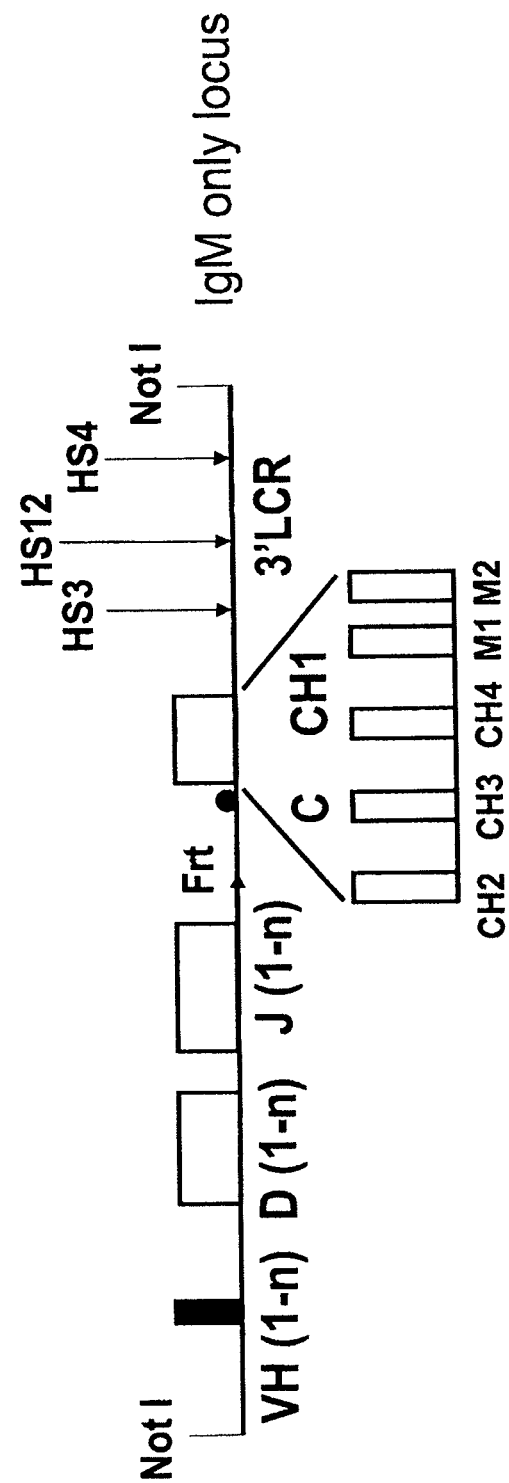
Figure 12:
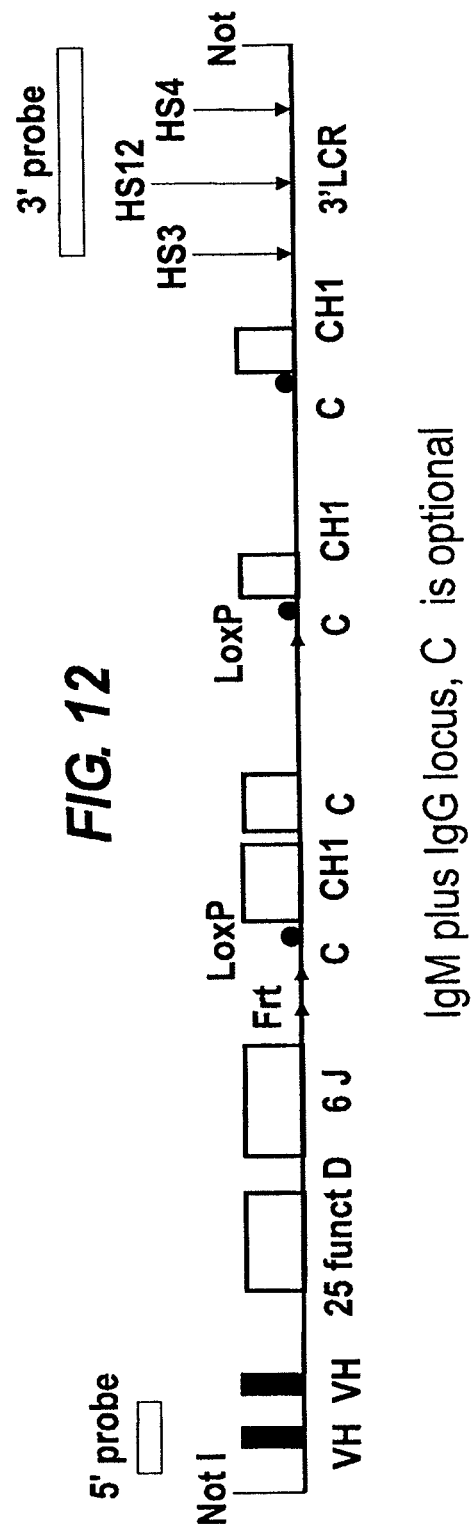
Figure 13:
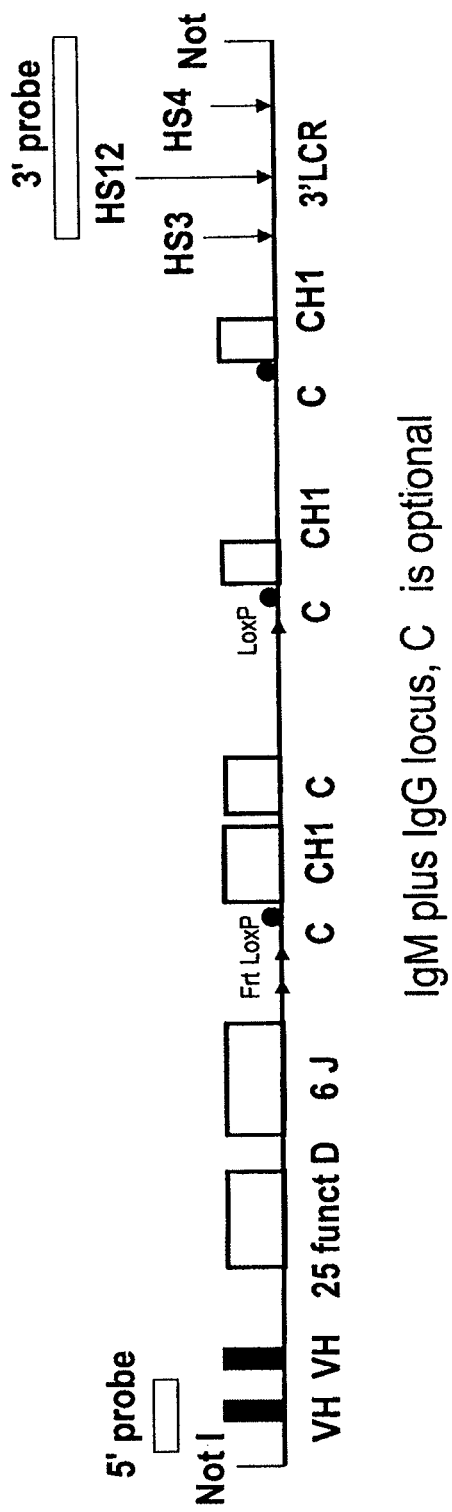

Using standard techniques, the Cγ3 and Cγ2 genes were subcloned separately into pFastBac vector (Invitrogen). Similarly any of the other Ig constant regions can be cloned from these BACs (IgA, IgE). A complete deletion of CH1 exon was achieved by homologous recombination (Imam et al. (2001)) using sequences that flank the CH1 exon of each constant region. An frt site could optionally be introduced in front of the Cμswitch region to allow the generation of single copy loci from multicopy loci by treatment with flp recombinase in vivo by standard means e.g. by breeding to *rosa*-flp mice (FIG. 10).

The separate VH genes, D and J segments and C and LCR exons were cloned into one BAC either by conventional restriction digestion and ligations or by homologous recombination (or a mixture of both) or any other cloning technique.

Further constructs could then be created.
IgM-Only Locus

In order to obtain the IgM construct (FIG. 11), one or more VHs genes (preferably engineered human VH genes to provide solubility or camelid VHH genes), followed by human D and J heavy chain segments and Cμ, were cloned into a BAC. For the methodology see above. In this case only the Cμ region was cloned into the final BAC.
IgM Plus IgG Locus, (Cδ is Optional)

In order to obtain the IgM plus IgG construct (FIG. 12), one or more VHs genes (preferably engineered human VH segments to provide solubility or camelid VHH genes), followed by human D and J heavy chain segments, Cμ (without CH1 but with CH4 exon), (optional Cδ) and the modified human Cγ2 and Cγ3 genes and 3' LCR were cloned into a BAC. In order to generate an IgG only locus loxP sites were introduced during the standard cloning steps (described above) and the BAC is grown in 294 Cre *E. coli* strain (Buscholz et al.) and cre mediated recombination yields bacteria producing an IgG only locus. For further construction details see above.
IgM Plus IgG Locus (Cδ is Optional)

In order to obtain the IgM plus IgG construct (FIG. 13), one or more VHs genes (preferably engineered human VH genes to provide solubility or camelid VHH genes), followed by human D and J heavy chain segments, Cμ (with CH1 and CH4), (optional Cδ) and the modified human Cγ2 and Cγ3 genes and 3' LCR were cloned into a BAC. In order to generate an IgG only locus loxP sites were introduced during the standard cloning steps (described above) and the BAC was grown in 294 Cre *E. coli* strain (Buscholz et al.) and cre mediated recombination yielded bacteria producing an IgG only locus.
Transgenic Mice, Breeding and Genotyping The final BAC was introduced into transgenic mice by standard microinjection of fertilized eggs or via embryonic stem cell transfection technology.

Transgenic loci were checked for integrity and number of copies by Southern blot analysis of tail DNA (Southern 1975) using 5' and 3' end locus probes. Founders were bred as lines in the μMT$_{-/-}$ background. Genotyping was done by standard PCR analysis using primers for each of the different regions of the locus. Sequence analysis of the RT-PCR products derived from BM cDNA of transgenic mice where the entire CH1 exon from both the Cγ2 and the Cγ3 was been deleted (one with (HLL lines) and one without the Cμ and Cδ genes, showed that the transgenic loci are not only capable of VDJ recombination, but that the IgG transcripts resemble those found in llama and camel HCAbs.
Immunohistochemistry Spleens were embedded in OCT compound. Frozen 5 μm cryostat sections were fixed in acetone and single or double labeled as previously described (Leenen et al. 1998). Monoclonal antibodies anti B220/RA3-6B2, anti-CD11c/N418 (Steinman et al., 1997), were applied as hybridoma culture supernatants. Peroxidase coupled goat anti-human IgG and anti-human IgM were from Sigma. Second-step reagents were peroxidase labeled goat anti-rat Ig (DAKO, Glostrup, Denmark) or anti-hamster Ig (Jackson ImmunoResearch Laboratories, West Grove, Pa.) and goat anti-rat Ig alkaline phosphatase (Southern Biotechnology, Birmingam, Ala., USA).

FIG. 15 shows the immunohistochemical analysis of 5 μm frozen sections of spleens from μMT$^{-/-}$, WT and HLL and HLL-MD transgenic mice in the μMT$^{-/-}$ background. Sections were stained with anti B220 (blue) for B cells and anti-CD11c/N418 (brown) for dendritic cells. Arrows indicate the location of small clusters of B cells.
Flow Cytometric Analyses Single cell suspensions were prepared from lymphoid organs in PBS, as described previously (Slieker et al. 1993). Approximately 1×10$^6$ cells were incubated with antibodies in PBS/0.5% bovine serum albumin (BSA) in 96 well plates for 30 min at 4° C. Cells were washed twice in PBS/0.5% BSA. For each sample, 3×10$^4$ events were scored using a FACScan analyzer (Becton Dickinson, Sunnyvale, Calif.). FACS data were analyzed using CellQuest version 1.0 computer software. Four-color analysis was performed on a Becton Dickinson FACS Calibur. The following mAbs were obtained from BD Pharmingen (San Diego, Calif.): FITC conjugated anti B220-RA3-6B2, PE conjugated anti CD19. FACS scan data of spleen cells, stained with anti-CD19 and anti-B220 are displayed in the bottom panel of FIG. 15.

On the left of the figure is a representation of Flp recombination in vivo by breeding HLL lines to a FlpeR transgenic line and supporting FACS scan data on spleen cells of the recombinant, showing B cell rescue as seen in the directly generated original HLL-MD lines. On the right is a representation of Cre recombination in vivo by breeding to Cag Cre transgenic line and FACS data on spleen cells of the single copy recombinant.

Immunization and Hybridoma Production (FIG. 14)

Transgenic mice containing a heavy chain only antibody locus consisting of two llama VHH domains, human D and J regions and IgG2 and 3 constant regions (without a CH1 domain) were created.

8 week old mice were immunized with either *E. Coli* heat shock protein 70 (hsp70). 20 μg or 5 μg of antigen with Specol adjuvant (IDDLO, Lelystadt, N L) was injected respectively s.c. on days 0, 14, 28, 42 and i.p. on day 50. Blood was taken on day 0, 14 and 45. After three boosts a low titer of antigen specific antibodies was detected in 1 out of 3 Hsp70 immunized HLL-MD1 mice (FIG. 14).

A standard spleen cell fusion with a myeloma cell line was performed to generate a monoclonal antibody resulting in a monoclonal hybridoma cell line against the hsp70 protein. The anti-HSP 70 HCAb consists of the llama VHH segment closest to the D region (VHH 2) recombined to the human IgHD3-10 segment (acc.num. X13972) and the human IgHJ4-02 segment (acc.num.X86355). Although not at high frequency, the VHHs has a few mutations that give rise to the amino acid alterations seen in FIG. 9A when compared to the germ line configuration. The RT-PCR analysis also showed only one productive IgH transcript in the hybridoma, suggesting that there are no other transcripts made. The αHSP70 IgG2 antibody is secreted as heavy chain only dimer (Western blots under denaturing gel (dimer) and non denaturing gel (monomer) conditions FIG. 14). Spleen cells were fused with Sp2-O—Ag14 myeloma cells (gift from R. Haperen) on day 56 using a ClonalCellTM-HY kit (StemCell Technologies, UK) according to the manufacturer's instructions.

Transgenic mice containing a heavy chain only antibody locus consisting of two llama VHH domains, human D and J regions, a human IgM and IgG2 and 3 constant regions (all without a CH1 domain, FIG. 12) were immunized with TNFα to obtain HC-IgM antibodies. One out of three mice showed positive sera in standard ELISA assays. A standard myeloma fusion yielded a positive IgM hybridoma (FIG. 16). After gel filtration on Sepharose 6B under non-reduced conditions each fraction was of the column was loaded to a gel under reducing conditions and detected by αhuman IgM-HRP (FIG. 20). Fractionation under non reducing conditions showed that the HC-IgM is secreted as a multimeric antibody with the same size as a human control IgM (after subtraction of the molecular weight of light chains and the CH1 domain that are absent from the HC-IgM). The gel fractionation of each column fraction under reducing conditions showed the expected monomer of (FIG. 20).

Serum Ig ELISA

Blood from 15-25 weeks old mice was collected in EDTA coated tubes, spun for 15' at room temperature (RT) and the supernatant diluted 1:5 in PBS. A 96 well plate was coated for 2 h with 5 mg/ml of a goat anti human IgG (YES Biotechnology) or a goat anti human IgM (Sigma), washed with PBS, blocked for 1 h at RT with blocking solution (1.5% BSA/1.5% powder milk/0.1% tween 20/PBS) and washed three times with PBS. Dilution series of serum samples and standards (human IgG2 or human IgM (Sigma, Zwijndrecht, NL)) were loaded and incubated for 2-4 h and the plates washed 6 times with PBS before addition of a secondary antibody (1:2000 diluted goat anti human IgG or goat anti human IgM coupled to HRP (Sigma, Zwijndrecht, NL)). All dilutions were done in a blocking solution. After 1-2 h incubation at RT and washing in PBS, POD substrate (Roche) was added.

The ELISA for the detection of antigen specific soluble sdAbs from the IgG2 phage library is shown in FIG. 16. Soluble sdAbs were used as primary antibodies on antigen-coated plates, followed by mouse α-myc antibody and HRP conjugated goat α-mouse antibody. POD was used as a substrate. The bottom panel shows fingerprinting of clones with restriction enzyme Hinf I, showing 5 different inserts coding for sdAb against *B. Pertusis*.

Antibody Library Construction and Screening

Total RNA was isolated from spleens of DKTP immunized single copy IgG only mice (FIG. 12 after cre treatment) using an Ultraspec RNA isolation system (Biotecx Laboratories Inc, Houston, Tex., USA). cDNA was made using oligo dT. DNA fragments encoding VHHDJ fragments were amplified by PCR using specific primers: vh1 back Sfi I primer (Dekker et al 2003) in combination with hIgG2hingrev primer (5'-AATCTGGGCAGCGGCCGCCTCGACACAA-CATTTGCGCTC-3', SEQ ID NO:1). The amplified VHH-DJs (~400 bp) were Sfi I/Not I digested, gel purified and cloned into Sfi I/NotI digested phagemid vector pHEN-1.

Transformation into TG1 electro-competent cells yielded in a human single domain antibody library. Two rounds of selection were performed using panning on vaccine antigens adsorbed onto plastic (immunotubes coated with undiluted vaccine). Restriction analysis and sequencing were standard.

RT-PCR of Heavy Chain-Only Locus

It was then investigated whether HLL-MD locus functions as a normal locus in producing a diverse antibody repertoire by sequencing the RT PCR products obtained using IgG2 and IgG3 specific primers on cDNA from Peyer's patches. FIG. 17 shows some examples of somatic mutations of clones from non immunized mice (left panel) and immunized mice (right panel). The mice were IgG only loci, immunized *E. Coli* hsp70, Pertussis lysate, tetanus toxoid. In grey shade is the IgG2 hinge region starting with ERKCCV Although, the RT-PCR analysis on Peyer's patches showed that both VH are used, all the antibodies sequenced rearranged the VH2. The source of repertoire variability is the CDR3 region formed by the selection of D and J segments and by the V-D and D-J junctions. The use of human J segments is similar to that seen in human rearrangements, with the JH4 and JH6 segments being used most often.

This analysis showed that both VHs, different human D and all of the human J segments are used, to contribute to a diverse antibody repertoire. It also showed the presence of IgG3 switched B cells and the occurrence of somatic mutations by comparison of each rearranged gene with its germline counterpart i.e. the original VH in the transgenic construct (see FIG. 17). Therefore, the human heavy chain-only IgG antigen receptor can provide the necessary signals for B cell maturation.

Immunostaining

FIG. 18 shows immunostaining results of one of Tet- on cell line additionally transfected with the response plasmid containing A5 antibody (Dekker et al. 2003). The upper panel shows doxycicline induced production of A5 antibody (red) in cytoplasm and nuclear staining of the cells with DAPI (blue). Lower panel shows that cells expressing rtTA in nucleus are the ones producing the A5 upon induction (upper panel). Staining was done with one of the human HCAb against rtTA (green) with the sequence shown below. The FITC conjugated goat anti human IgG was used as a secondary step. A5 was detected as previously described by Dekker et al 2003. The rTTA antibody was an IgG3 with the following sequence (SEQ ID NOs:2 and 3:

```
241 AGACTCT

80 R   L

301 CCTGTGCAGCCTCTGGAAGCATCTTCAGTATCAATGCCATGGGCTGGTACCGCCAGGCTC

100 S   C   A   A   S   G   S   I   F   S   I   N   A   M   G   W   Y   R   Q   A

361 CAGGGAAGCAGCGCGAGTTGGTCGCAGCTATTACTAGTGGTGGTAGCACAAGGTATGCAG

120 P   G   K   Q   R   E   L   V   A   A   I   T   S   G   G   S   T   R   Y   A

421 ACTCCGTGAAGGGCCGATTCACCATCTCCAGAGACAACGCCAAGAACACGGTGTATCTGC

140 D   S   V   K   G   R   F   T   I   S   R   D   N   A   K   N   T   V   Y   L

481 AAATGAACAGCCTGAAACCTGAGGACACGGCCGTCTATTACTGTTTGATCTCTATGGTTC

160 Q   M   N   S   L   K   P   E   D   T   A   V   Y   Y   C   L   I   S   M   V

541 GGGGAGCCCGTTTTGACTACTGGGGCCAGGGAACCCTGGTCACCGTCTCCTCAGAGCTCA

180 R   G   A   R   F   D   Y   W   G   Q   G   T   L   V   T   V   S   S   E   L

601 AAACCCCACTT

200 K   T   P   L
```

The IgG3 hinge starts at amino acid 198 ELKTPL. For comparison see the IgG2 hinge region in FIG. 17.

Western Blot Analyses

FIG. 19 shows Western blots of sera of different transgenic mouse lines containing the IgM plus IgG locus (FIG. 10) after cre treatment (ie IgM deleted, only IgG left). Sera were purified by prot G and gel fractionated under reducing (FIG. 19 right panel) and non reducing (FIG. 19, left panel) conditions. The controls were the background KO mice and a normal human serum sample. Note the size difference between the two gels showing that the human heavy chain only IgG is a dimer.

The signal shown in FIG. 19 was detected with an anti-human IgG antibody by standard procedures.

Size Fractionation of Human IgM Produced by the IgM Plus IgG Locus Mouse

The serum from the IgM plus IgG mice (FIG. 13) was fractionated by gel filtration under non reducing conditions after mixing with a human serum sample as a control. Results are shown in FIG. 20. Molecular weights of the complexes on the column decrease with each lane (representing each fraction) from left to right. The fractions (each lane) were analysed by gel electrophoresis under reducing conditions.

ELISA analysis was performed on a number of hybridomas made from mice containing the IgM plus IgG (FIG. 13) locus immunized with human TNFα. Results are shown in FIG. 21. The top two rows in FIG. 21 were analysed with an anti-human IgG, the next two rows with an anti human IgM. The serum samples (arrows) show that the mouse has generated both IgG and IgM anti-TNFα antibodies. The single arrow shows a positive IgM hybridoma. The wells were coated with commercially available human TNFα. All procedures were standard.

Example 2

The bi-specific bi-valent antibody was generated by combining two heavy chain only mono-specific antibodies. The first antibody forms the backbone bringing in the first specificity and the effector functions (variable region and constant region respectively). This was combined with the second antibody with the second specificity via a newly designed hinge. This hinge was similar to the existing IgG2 hinge sequence but was altered by replacing the cysteins with prolines to prevent crosslinking of the cysteins in the antibody dimer and providing extra flexibility via the prolines to prevent the second antibody being spatially constrained, which otherwise may have inhibited its function.

The starting backbone antibody was an antibody raised against the E. coli HSP70 protein. The HSP70 antigen was injected into transgenic mice that contained a heavy chain only antibody locus as described in (see above FIG. 14). A monoclonal antibody was raised from these animals by standard hybridoma fusion technology (see above). The cDNA coding for the αHSP-antibody was subsequently cloned by standard RT-PCR recombinant DNA methods resulting in a plasmid containing a full length cDNA that included from the 5' end to the 3' end (in the protein from the N terminus to COOH terminus) the start codon ATG, the signal peptide sequence, the variable domain VHH1 (see Janssens et al.), the recombined D and J region and the constant region of Cγ2 (lacking a CH1 region), but including the stop codon and the polyA site (FIG. 22 upper left). The cDNA coding for the αHSP70 antibody was amplified by PCR for cloning using a forward primer and a reverse primer.

The forward primer was: CTG<u>GAATTC</u>TCAACC ▓▓▓ GAGCTGGGGCTGAGC (SEQ ID NO:4) providing an EcoRI site for cloning purposes (underlined) an efficient translation start sequence (bold) and the normal start codon (greyshade).

The reverse primer was: GAC<u>AAGCTT</u>TACCCGGAGACAGGGAGAGGC (SEQ ID NO:5) providing a HindIII cloning site (underlined) and remaining the normal stop codon.

The amplification therefore leads to a EcoRI/HindIII fragment containing an EcoRI site (underlined), an efficient translation start sequence (bold) and the normal start codon of the aHSP antibody gene (greyshade, see also FIG. 22).

The amplification therefore leads to a EcoRI/HindIII fragment containing an EcoRI site (underlined), an efficient translation start sequence (bold) and the normal start codon of the αHSP antibody gene (greyshade, see also FIG. 22).

The reverse 3' end primer was: GAC AAGCTTTACCCGGAGACAGGGAGAGGC (SEQ ID NO:6) providing a HindIII cloning site (underlined) and removing the normal stop codon. This resulted in a fragment (FIG. 22 left second from top) with an EcoRI site to clone onto a promoter sequence and a HindIII site for cloning the 5' end onto the expression plasmid and the 3' end onto a novel hinge sequence (see below). Lastly the fragment was cut with EcoRI and HindIII to provide the appropriate single stranded ends for cloning.

The second cloned antibody bringing in the second specificity comprised the VHH domain of a llama antibody against the pig retrovirus (PERV) gag antigen (Dekker et al., (2003) J. Virol., 77 (22): 12132-9, FIG. 22 top right). The αgag was amplified via standard PCR amplification using the following primers:

Forward: GTC▓▓▓▓▓▓GCCCAGGTCCAACTGCAG-GAGTCTG (SEQ ID NO:7) and the reverse primer GTC GAATTCTCATTCCGAGGAGACGGTGACCTGGG TC (SEQ ID NO:8). This provides the amplified fragment (FIG. 22 right second from top) with a XhoI site (greyshade) to clone the 5' end in frame with the novel hinge (see below) and an EcoRI site (underlined) for cloning the 3' end into the expression plasmid (FIG. 22, right middle). Lastly the fragment was cut with EcoRI and XhoI to generate single stranded ends for cloning.

The two antibody sequences were combined into one diabody sequence via the novel hinge. The novel hinge was generated from two oligonucleotides that together form a double strand oligonucleotide with 5' and 3' overhangs (respectively HindIII and XhoI compatible) for cloning purposes. It was designed to be in frame with the end of the αHSP70 sequence and the start of the αgag sequence. Formation of the sulphide bridges normally present in the human IgG2 hinge, was prevented by replacing the cysteins (greyshade) with prolines (underlined). The prolines add extra flexibility to the hinge to allow the proper functioning of the second antibody domain that becomes connected to COOH terminus of the first antibody via the hinge.

The normal IgG hinge sequence (cysteine codons in greyshade, proline codons underlined) GAGCGCAAATG ▓▓▓▓▓CGAG▓▓CCACCG▓▓CCA (SEQ ID NO:9) and its complement were replaced by AGCTTCT-GAGCGCAAACCACCAGTCGAGCCACCACCG CCACCAC (SEQ ID NO:10) and its complement TCGAGTGGTGGCGGTGGTGGCTCGACTG-GTGGTTTGCGCTCAGA (SEQ ID NO:11). This also provided the fragment (white box hinge, FIG. 22, center) with two single strand ends compatible with HindIII (bold) and XhoI (italic) sites for cloning purposes.

This also provided the fragment (white box hinge, FIG. 22, center) with two single strand ends compatible with HindIII (bold) and XhoI (italic) sites for cloning purposes.

The three fragments (αHSP70 IgG2, hinge and αgag) were subsequently ligated into a bluescript (Pbluescript11 sk+) expression plasmid that contains a chicken actin promoter and a CMV enhancer sequence (FIG. 22, expression plasmid) by standard recombinant DNA technology. When this plasmid is expressed (see below) it results in the diabody shown at the bottom of FIG. 22.

The diabody expression plasmid was grown and cotransfected with the plasmid pGK-hygro (to allow the selection of transfected cells) by standard methods (Superfect) into CHO cells (FIG. 23). Positive clones were selected in hygromycin containing medium and positively identified as expressing the diabody by performing a standard α gag ELISA (Dekker et al., J. Virol. 2003) of the growth medium containing secreted diabody by the CHO cells using an ahuman IgG-HRP detection. Positively testing for the α-gag activity makes it most likely that a given clone expresses the entire diabody, because the gag specificity is at the back-end (COOH terminus) of the diabody. A subsequent ELISA for HSP70 was also positive. Western blots of these ELISA selected clones under non-reducing and reducing conditions were performed in order to show that the protein expressed from the plasmid was a dimer of 110 kD (as shown at the bottom of FIG. 23), compared to the monomer of 55 kD (non reducing and reducing conditions and Western blots, FIG. 23 right). Thus the ELISA and the Western blot together show that the diabody is expressed and secreted into the medium as a dimer by the transfected CHO cells (at >70 ng/ml) and that the antibody can bind the HSP70 and gag antigens. However it does not show that the same dimer diabody molecule can bind both antigens at the same time.

Therefore, a follow-up experiment was carried out. First the gag antigen was fixed to the bottom of a plastic well (first well FIG. 24 center). The diabody (FIG. 24 top) was subsequently captured by the first antigen (gag) after application of the CHO cell supernatant of clone 1 (second well FIG. 24 center). This was followed by extensive washing and then application of the second antigen (HSP 70, FIG. 24 center third well), again followed by extensive washing. If a diabody molecule could bind both antigens at the same time, it should be captured to the bottom of the well by binding the first antigen (gag) and then capture the second antigen (HSP70). When the entire complex was subsequently eluted form the well (FIG. 24 center, right well) both the diabody and the antigens were visible on a Western blot (FIG. 24 bottom).

In order to collect the secreted diabody the CHO clones were grown under the same standard conditions and in media (SIGMA hybridoma medium, serum-free) used for the collection of antibodies from hybridomas.

Methods: Wells of a Nunc-Immuno plate (Maxisorp) were coated with purified recombinant gag protein (12.5 μg/ul in PBS) O/N 4C. Blocked for two hrs with 1% milk/1% BSA in PBS. CHO-DB clone-1 medium ½ diluted in PBS-Milk-BSA (or controls) were incubated for 3 hrs at room temperature (RT). Bacterial B121 cell lysate (containing HSP70 protein) ½ diluted in PBS-Milk-BSA was incubated for 3 hrs at RT and washed. Bound proteins were eluted with Laemmli sample buffer containing 2-Mercaptoethanol. The samples were analysed by Western blot and therefore run on a 10% SDS-PAGE and blotted on nitrocellulose membrane. The blot was blocked for two hrs with PBS-Milk-BSA and incubated with primary antibodies. The products were visualized by standard methods using secondary antibodies coupled to enzymes that allow visual staining. The reagent used were:
α Gag: Rabbit polyclonal (1:2000) 2 hrs RT
α Diabody: Goat a human IgG-HRP (1:2500) 2 hrs RT
α HSP70: Monoclonal G20-380 medium (1:2) 2 hrs RT.
Secondary antibodies were: Goat α Rabbit-AP (1:2000) 2 hrs RT and Goat α Human IgG-HRP (1:2500) 2 hrs RT against the HSP70 monoclonal.

To visualize the protein bands first NBT/BCIP substrate (purple) reacting with alkaline phosphatase (AP) and second DAB substrate (brown) reacting with horseradish peroxidase (HRP) was used.

All washing steps were done with PBS-0.05% Tween-20.

Controls were carried out by leaving out one of the components or adding medium from CHO cells not producing diabodies (FIG. 24), i.e; lacking no diabody application (medium from non transfected CO cells) and has therefore only gag (lane 2); lacking gag at the bottom of the well (replaced by milk protein) and should therefore have none of the products (lane 3); lacking gag and diabody and should have none of the products (lane 4); lacking HSP70 antigen (replaced by milk antigen) and should therefore have only the diabody and gag (lane 5); lacking HSP70 and diabody and should have only gag (lane 6).

The fact that all three components (the diabody plus both antigens) were only present in the well of lane 1 that received all three components (see also legend bottom of FIG. 24) shows that the single diabody binds both antigens at the same time.

Generation of Bispecific IgA or Multi-Specific IgM

Figure 25:
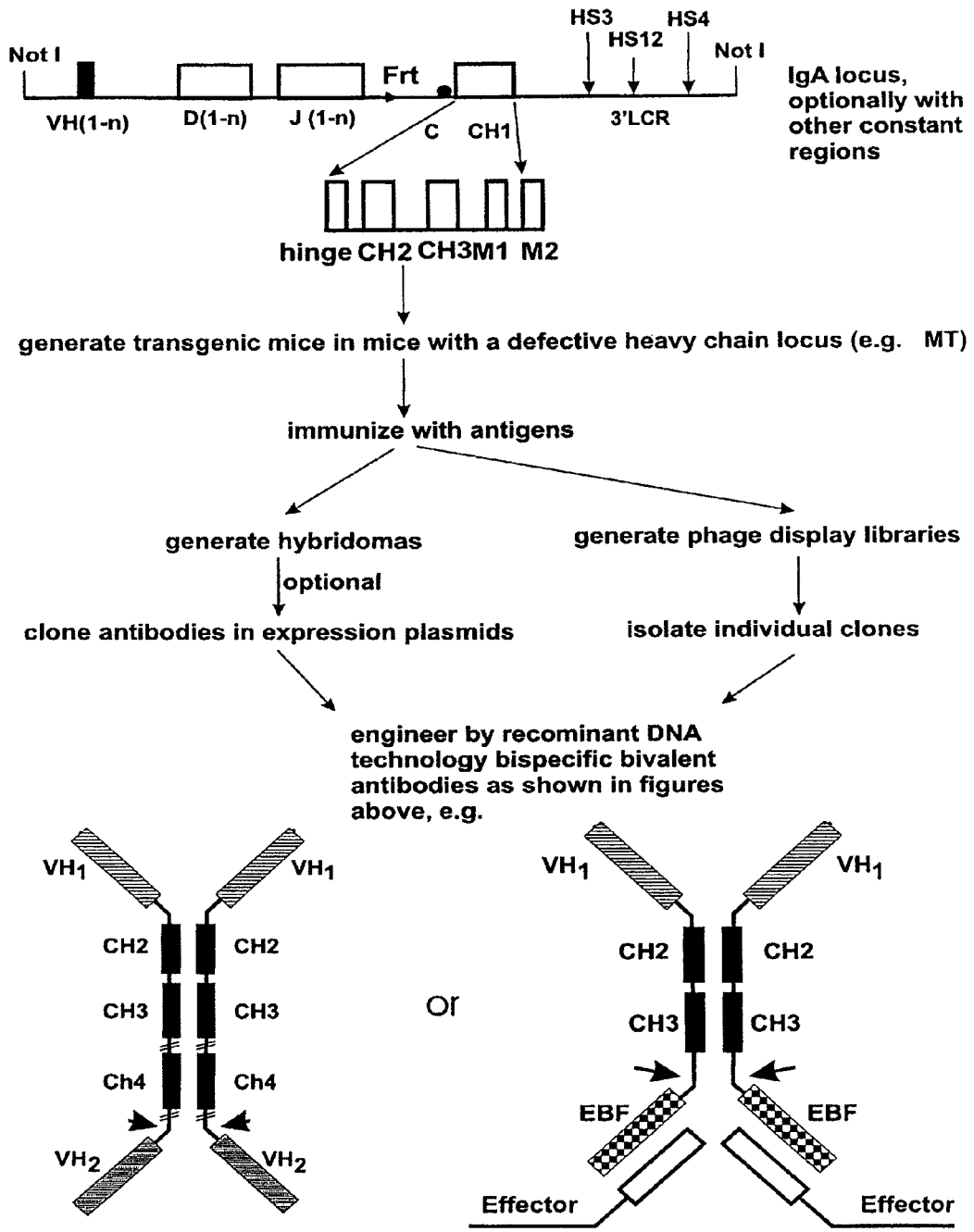

The generation of bispecific IgA is essentially as described for IgG (above), but using in addition to the Vhsol, D and J, the constant region Cα leading to the generation of IgA (FIG. 25).

The generation of IgM is largely similar, but offers an additional possibility because IgM molecules can form large multimers (with or without J chains). Thus in addition to molecules similar to those described above (FIG. 26 right bottom, after elimination of the multimerisation sequences), one can also generate multimers simply by co-expressing IgM's with different specificities (FIG. 26 left bottom).

Example 3

An expression vector encoding a polypeptide complex comprising: a heavy chain including a binding domain which binds to PSCA (prostate stem cell antigen), an assembly domain consisting the leucine zipper motif of Jun and antibody hinge, CH2 and CH3 domains; and a light chain including a complementary assembly domain consisting of the leucine zipper motif of Fos is constructed using molecular biology techniques as described in Sambrook et al ((1989) Molecular Cloning—A Laboratory Manual, Cold Spring Harbor Laboratory Press).

The expression vector is then transferred to a suitable host cell by conventional techniques to produce a transfected host cell for optimized expression of the vector. The transfected or transformed host cell is then cultured using any suitable technique known to these skilled in the art to produce the polypeptide complex of the invention. Once produced, the polypeptide complexes are purified by standard procedures of the art, including cross-flow filtration, ammonium sulphate precipitation and affinity column chromatography (e.g., protein A).

The soluble effector domain consisting of 3,3'-diindolylmethane (DIM) is then fused to the complementary assembly domain using techniques known to those skilled in the art.

Example 4

An expression vector encoding the heavy chain of the polypeptide complex of the present invention comprising; a soluble VHH binding domain which binds to AFP (Alpha-Fetoprotein) and an assembly domain consisting the leucine zipper motif of Jun, and antibody hinge, CH2 and CH3 domains is constructed using molecular biology techniques as described in Sambrook et al.

A second expression vector encoding the light chain of the polypeptide complex of the present invention is also constructed. This comprises a complementary assembly domain consisting of the leucine zipper motif of Fos.

The expression vectors are then transferred to a suitable host cell by conventional techniques to produce a co-transfected host cell for optimized expression of the vector. The transfected or transformed host cell is then cultured using any suitable technique known to these skilled in the art to produce the polypeptide complex of the invention.

Once produced, the polypeptide complexes are purified by standard procedures of the art, including cross-flow filtration, ammonium sulphate precipitation and affinity column chromatography (e.g., protein A).

The soluble effector domain consisting of 3,3'-diindolylmethane (DIM) is then fused to the complementary assembly domain using techniques known to those skilled in the art.

Example 5

VCAM and VLA-4

An expression vector encoding a polypeptide complex comprising: a heavy chain including a binding domain which binds to PSCA (prostate stem cell antigen), an assembly domain consisting VCAM and antibody hinge, CH2 and CH3 domains; and a light chain including a complementary assembly domain consisting of VLA-4 fused to ricin A toxin is constructed using molecular biology techniques as described in Sambrook et al.

The expression vector is then transferred to a suitable host cell by conventional techniques to produce a transfected host cell for optimized expression of the vector. The transfected or transformed host cell is then cultured using any suitable technique known to these skilled in the art to produce the polypeptide complex of the invention.

Once produced, the polypeptide complexes are purified by standard procedures of the art, including cross-flow filtration, ammonium sulphate precipitation and affinity column chromatography (e.g., protein A).

Example 6

An expression vector encoding a polypeptide complex comprising: a heavy chain including a binding domain which binds to PSCA (prostate stem cell antigen), an assembly domain consisting the leucine zipper motif of Jun and antibody hinge, CH2 and CH3 domains; and a light chain including a complementary assembly domain consisting of the leucine zipper motif of Fos and a soluble effector domain encoding purine nucleoside phosphorylase (PNP) is constructed using molecular biology techniques as described in Sambrook et al.

The expression vector is then transferred to a suitable host cell by conventional techniques to produce a transfected host cell for optimized expression of the vector. The transfected or transformed host cell is then cultured using any suitable technique known to these skilled in the art to produce the polypeptide complex of the invention.

Once produced, the polypeptide complexes are purified by standard procedures of the art, including cross-flow filtration, ammonium sulphate precipitation and affinity column chromatography (e.g., protein A).

PNP converts fludarabine to the toxic metabolite 2-fluoroadenine which kills the cells that comprise the PNP enzyme and in addition diffuses to kill surrounding uninfected cells, a local bystander effect.

Example 7

An expression vector encoding a first heavy chain of the polypeptide complex of the present invention comprising; a soluble VHH binding domain which binds to V3-PND region of glycoprotein antigen gp120 and an assembly domain consisting the leucine zipper motif of Jun and antibody hinge, CH2 and CH3 domains is constructed using molecular biology techniques as described in Sambrook et al.

A second expression vector encoding a second heavy chain of the polypeptide complex of the present invention is also constructed comprising: a soluble VHH binding domain which binds to GP-41, an assembly domain consisting of the leucine zipper motif of Jun and antibody hinge, CH2 and CH3 domains.

A third expression vector encoding the light chain of the polypeptide complex of the present invention is also constructed. This comprises a complementary assembly domain consisting of the leucine zipper motif of Fos.

The expression vectors are then transferred to a suitable host cell by conventional techniques to produce a co-transfected host cell for optimized expression of the vector. The transfected or transformed host cell is then cultured using any suitable technique known to these skilled in the art to produce the polypeptide complex of the invention.

Once produced, the polypeptide complexes are purified by standard procedures of the art, including cross-flow filtration, ammonium sulphate precipitation and affinity column chromatography (e.g., protein A).

The soluble effector domain consisting of HIV-1 MN V3 (PND) peptide immunogen is then fused to the complementary assembly domain using techniques known to those skilled in the art.

Example 8

An expression vector encoding a first heavy chain of the polypeptide complex of the present invention comprising: a soluble VHH binding domain which binds to V3-PND region of glycoprotein antigen constructed using molecular biology techniques as described in Sambrook et al ((1989) Molecular Cloning—A Laboratory Manual, Cold Spring Harbor Laboratory Press).

A second expression vector encoding a second heavy chain of the polypeptide complex of the present invention is also constructed comprising: a soluble VHH binding domain which binds to GP-41.

The two heavy chains are characterised in that the constant regions for the two heavy chains comprise identical μ, CH2, CH3 and CH4 domains.

The expression vectors are then transferred a host cell which constitutively expresses a J chain by conventional techniques to produce a co-transfected host cell for optimized expression of the vector. The transfected or transformed host cell is then cultured using any suitable technique known to these skilled in the art to produce the polypeptide complex of the invention.

Once produced, the polypeptide complexes are purified by standard procedures of the art, including cross-flow filtration, ammonium sulphate precipitation and affinity column chromatography (e.g., protein A).

The soluble effector domain consisting of HIV-1 MN V3 (PND) peptide immunogen is then fused to the complementary assembly domain using techniques known to those skilled in the art.

All publications mentioned in the above specification are herein incorporated by reference.

Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, molecular biology and biotechnology or related fields are intended to be within the scope of the following claims.

What is claimed is:

1. A method for the production of a soluble, antigen-specific $V_H$ binding domain comprising:
   a. immunising a transgenic mouse expressing a heterologous $V_H$ heavy chain locus with an antigen wherein:
      i. the $V_H$ heavy chain locus comprises a variable region comprising at least one naturally occurring human $V_H$ gene segment, at least one D gene segment, at least one J gene segment and at least one heavy chain constant region;
      ii. each constant region does not encode a functional $C_H1$ domain;
      iii. the $V_H$ gene segment, D gene segment and J gene segment are capable of recombining to form a VDJ coding sequence;
      iv. the recombined $V_H$ heavy chain locus, when expressed upon antigen challenge, is capable of forming a soluble, heavy chain-only antibody comprising a soluble, antigen-specific $V_H$ binding domain and a constant effector region devoid of a functional $C_H1$ domain with an antigen;
   b. cloning a $V_H$ locus resulting from recombination between single V, D and J gene segments encoding a soluble, antigen-specific $V_H$ binding domain from an antibody-producing cell of said immunised transgenic mouse after affinity maturation via somatic mutation; and
   c. producing said soluble, antigen specific $V_H$ binding domain from the clone of step b.

2. The method of claim 1, wherein steps b to c of claim 1 are carried out by:
   a. isolating a cell or tissue expressing an antigen-specific, heavy chain-only antibody of interest;
   b. producing a hybridoma from the cell or tissue of step (b);
   c. cloning the heavy chain-only antibody mRNA from said hybridoma; and
   d. producing said soluble, antigen-specific $V_H$ domain by identifying and isolating mRNA encoding said soluble, antigen-specific $V_H$ domain from the mRNA of step c.

3. The method of claim 1, wherein steps b to c of claim 1 are carried out by:
   a. isolating a cell or tissue expressing an antigen-specific, heavy chain-only antibody of interest;
   b. cloning the $V_H$ locus from mRNA derived from the isolated cell or tissue;
   c. displaying the encoded protein using phage or similar library;
   d. identifying soluble, antigen-specific $V_H$ domain(s); and
   e. expressing the soluble, antigen-specific $V_H$ domain(s) alone or as a fusion.

4. The method of claim 1, wherein the $V_H$ heavy chain locus comprises naturally occurring human D and J gene segments.

5. The method of claim 1, wherein the $V_H$ heavy chain locus comprises more than one $V_H$ gene segment, more than one D gene segment and more than one J gene segment.

* * * * *

UNITED STATES PATENT AND TRADEMARK OFFICE
CERTIFICATE OF CORRECTION

PATENT NO. : 8,921,522 B2  
APPLICATION NO. : 12/645653  
DATED : December 30, 2014  
INVENTOR(S) : Franklin Gerardus Grosveld et al.

It is certified that error appears in the above-identified patent and that said Letters Patent is hereby corrected as shown below:

IN THE CLAIMS:

In Col. 59, line 29, Claim 1, "domain with an antigen;" should read -- domain; --.

Signed and Sealed this
Twenty-fourth Day of November, 2015

Michelle K. Lee
*Director of the United States Patent and Trademark Office*

SEQUENCE LISTING

<160> NUMBER OF SEQ ID NOS: 35

<210> SEQ ID NO 1
<211> LENGTH: 39
<212> TYPE: DNA
<213> ORGANISM: Artificial Sequence
<220> FEATURE:
<223> OTHER INFORMATION: PCR primer

<400> SEQUENCE: 1
aatctgggca gcggccgcct cgacacaaca tttgcgctc                          39

<210> SEQ ID NO 2
<211> LENGTH: 318
<212> TYPE: DNA
<213> ORGANISM: Homo sapiens

<400> SEQUENCE: 2
agactctcct gtgcagcctc tggaagcatc ttcagtatca atgccatggg ctggtaccgc    60
caggctccag ggaagcagcg cgagttggtc gcagctatta ctagtggtgg tagcacaagg   120
tatgcagact ccgtgaaggg ccgattcacc atctccagag acaacgccaa gaacacggtg   180
tatctgcaaa tgaacagcct gaaacctgag gacacggccg tctattactg tttgatctct   240

```
atggttcggg gagcccgttt tgactactgg ggccagggaa ccctggtcac cgtctcctca      300
gagctcaaaa ccccactt                                                    318
```

<210> SEQ ID NO 3
<211> LENGTH: 106
<212> TYPE: PRT
<213> ORGANISM: Homo sapiens

<400> SEQUENCE: 3

```
Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Arg Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Leu Ile Ser
65                  70                  75                  80

Met Val Arg Gly Ala Arg Phe Asp Tyr Trp Gly Gln Gly Thr Leu Val
                85                  90                  95

Thr Val Ser Ser Glu Leu Lys Thr Pro Leu
            100                 105
```

<210> SEQ ID NO 4
<211> LENGTH: 33
<212> TYPE: DNA
<213> ORGANISM: Artificial Sequence
<220> FEATURE:
<223> OTHER INFORMATION: PCR primer

<400> SEQUENCE: 4

```
ctggaattct caaccatgga gctggggctg agc                                   33
```

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5

```
gacaagcttt acccggagac agggagaggc                                       30
```

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6

```
gacaagcttt acccggagac agggagaggc                                       30
```

<210> SEQ ID NO 7
<211> LENGTH: 34
<212> TYPE: DNA
<213> ORGANISM: Artificial Sequence
<220> FEATURE:
<223> OTHER INFORMATION: PCR primer
```

```
<400> SEQUENCE: 7
gtcctcgagg cccaggtcca actgcaggag tctg                                34

<210> SEQ ID NO 8
<211> LENGTH: 37
<212> TYPE: DNA
<213> ORGANISM: Artificial Sequence
<220> FEATURE:
<223> OTHER INFORMATION: PCR primer

<400> SEQUENCE: 8
gtcgaattct cattccgagg agacggtgac ctgggtc                             37

<210> SEQ ID NO 9
<211> LENGTH: 36
<212> TYPE: DNA
<213> ORGANISM: Homo sapiens

<400> SEQUENCE: 9
gagcgcaaat gttgtgtcga gtgcccaccg tgccca                              36

<210> SEQ ID NO 10
<211> LENGTH: 44
<212> TYPE: DNA
<213> ORGANISM: Homo sapiens

<400> SEQUENCE: 10
agcttctgag cgcaaaccac cagtcgagcc accaccgcca ccac                     44

<210> SEQ ID NO 11
<211> LENGTH: 44
<212> TYPE: DNA
<213> ORGANISM: Homo sapiens

<400> SEQUENCE: 11
tcgagtggtg gcggtggtgg ctcgactggt ggtttgcgct caga                     44

<210> SEQ ID NO 12
<211> LENGTH: 404
<212> TYPE: DNA
<213> ORGANISM: Homo sapiens

<400> SEQUENCE: 12
gacacggccg tgtagtatct gtaaggcaga tggggtagta ctatggttcg gggagtccac    60
cactgcggct agaggggcca gggaacactg gtcgcggtgt catcagcctc caccaagggc    120
ccatcggtct tccccctggc gccctgctcc aggagcacct ccgagagcac agcggccctg    180
ggctgcctgg tcaaggacta cttccccgaa ccggtgacgg tgtcgtggaa ctcaggcgct    240
ctgaccagcg gcgtgcacac cttcccagct gtcctacagt cctcaggact ctactccctc    300
agcagcgtgg tgaccgtgcc ctccagcaac ttcggcaccc agacctacac ctgcaacgta    360
gatcacaagc ccagcaacac caagagcgca atgttgtgt cgag                     404

<210> SEQ ID NO 13
<211> LENGTH: 352
<212> TYPE: DNA
<213> ORGANISM: Homo sapiens

<400> SEQUENCE: 13
gacattccca cttcgatctc tggggccgtg gcaccctggt cactgtctcc tcagcctcca    60
ccaagggccc atcggtcttc cccctggcgc cctgctccag gagcacctcc gagagcacag    120
```

```
cggccctggg ctgcctggtc aaggactact tccccgaacc ggtgacggtg tcgtggaact      180
caggcgctct gaccagcggc gtgcacacct tcccagctgt cctacagtcc tcaggactct      240
actccctcag cagcgtggtg accgtgccct ccagcaactt cggcacccag acctacacct      300
gcaacgtaga tcacaagccc agcaacacca agagcgcaaa tgttgtgtcg ag              352

<210> SEQ ID NO 14
<211> LENGTH: 394
<212> TYPE: DNA
<213> ORGANISM: Homo sapiens

<400> SEQUENCE: 14
gacacggccg tctattactg taatgccact acgatatttt gactggttat tatagacgct      60
actggggcca gggaaccctg gtcaccgtct cctcagcctc cgccaagggc ccatcggtct      120
tccccctggc gccctgctcc aggagcacct ccgagagcac agcggccctg ggctgcctgg      180
tcaaggacta cttccccgaa ccggtgacgg tgtcgtggaa ctcaggcgct ctgaccagcg      240
gcgtgcacac cttcccagct gtcctacagt cctcaggact ctactccctc agcagcgtgg      300
tgaccgtgcc ctccagcaac ttcggcaccc agacctacac ctgcaacgta gatcacaagc      360
ccagcaacac caagagcgca aatgttgtgt cgag                                  394

<210> SEQ ID NO 15
<211> LENGTH: 380
<212> TYPE: DNA
<213> ORGANISM: Homo sapiens

<400> SEQUENCE: 15
gacacggccg tccaatcgga tacagctatg gttacgtact ttgactactg gggccaggga      60
accctggtca ccgtctcctc agcctccacc aagggcccat cggtcttccc cctggcgccc      120
tgctccagga gcacctccga gagcacagcg ccctgggct gcctggtcaa ggactacttc       180
cccgaaccgg tgacggtgtc gtggaactca ggcgctctga ccagcggcgt gcacaccttc      240
ccagctgtcc tacagtcctc aggactctac tccctcagca gcgtggtgac cgtgccctcc      300
agcaacttcg gcacccagac ctacacctgc aacgtagatc acaagcccag caacaccaag      360
agcgcaaatg ttgtgtcgag                                                  380

<210> SEQ ID NO 16
<211> LENGTH: 417
<212> TYPE: DNA
<213> ORGANISM: Homo sapiens

<400> SEQUENCE: 16
gacacggccg tctattactg taatgcagat gtattactat ggttcgggga gcctatagcc      60
ttactactac tacggtatgg acgtctgggg ccaagggacc acggtcaccg tctcctcagc      120
ctccaccaag ggcccatcgg tcttcccccct ggcgccctgc tccaggagca cctccgagag     180
cacagcggcc ctgggctgcc tggtcaagga ctacttcccc gaaccggtga cggtgtcgtg      240
gaactcaggc gctctgacca gcggcgtgca caccttccca gctgtcctac agtcctcagg      300
actctactcc ctcagcagcg tggtgaccgt gccctccagc aacttcggca cccagaccta      360
cacctgcaac gtagatcaca agcccagcaa caccaagagc gcaaatgttg tgtcgag         417

<210> SEQ ID NO 17
<211> LENGTH: 108
<212> TYPE: PRT
<213> ORGANISM: Homo sapiens
```

```
<400> SEQUENCE: 17

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Lys
65                  70                  75                  80

Gly Pro Ile Thr His Val Arg Gly Val His Tyr Trp Gly Gln Gly Thr
                85                  90                  95

Leu Val Thr Val Ser Ser Glu Arg Lys Cys Cys Val
            100                 105

<210> SEQ ID NO 18
<211> LENGTH: 108
<212> TYPE: PRT
<213> ORGANISM: Homo sapiens

<400> SEQUENCE: 18

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Lys
65                  70                  75                  80

Thr Pro Ile Thr His Ile Arg Gly Val His His Trp Gly Gln Gly Thr
                85                  90                  95

Leu Val Thr Val Ser Ser Glu Arg Lys Cys Cys Val
            100                 105

<210> SEQ ID NO 19
<211> LENGTH: 108
<212> TYPE: PRT
<213> ORGANISM: Homo sapiens

<400> SEQUENCE: 19

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Arg
65                  70                  75                  80
```

Thr Pro Ile Thr Val Arg Gly Val His Tyr Trp Gly Gln Gly Thr
            85                  90                  95

Leu Val Thr Val Ser Ser Glu Arg Lys Cys Cys Val
            100                 105

<210> SEQ ID NO 20
<211> LENGTH: 108
<212> TYPE: PRT
<213> ORGANISM: Homo sapiens

<400> SEQUENCE: 20

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Lys Ala Lys Asn Thr Val Tyr Leu Gln Met
    50                  55                  60

Asn Ser Leu Lys Pro Glu Asp Ser Ala Val Tyr Tyr Cys Asn Arg Thr
65                  70                  75                  80

Gly Pro Ile Thr His Val Arg Gly Val Asp Tyr Trp Gly Arg Gly Thr
            85                  90                  95

Leu Val Thr Val Ser Ser Glu Arg Lys Cys Cys Val
            100                 105

<210> SEQ ID NO 21
<211> LENGTH: 108
<212> TYPE: PRT
<213> ORGANISM: Homo sapiens

<400> SEQUENCE: 21

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn His Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Glu
65                  70                  75                  80

Ser Pro Ile Thr Lys Val Arg Gly Val Ser Tyr Trp Gly Gln Gly Thr
            85                  90                  95

Leu Val Thr Val Ser Ser Glu Arg Lys Cys Cys Val
            100                 105

<210> SEQ ID NO 22
<211> LENGTH: 59
<212> TYPE: PRT
<213> ORGANISM: Homo sapiens

<400> SEQUENCE: 22

Arg Leu Ser Cys Ala Ala Ser Gly Phe Thr Leu Asp Tyr Tyr Ala Ile
1               5                   10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Ala Asp Ser Val Lys Gly
        35                  40                  45

Arg Phe Thr Ile Ser Arg Asp Asn Ala Lys Asn
    50                  55

<210> SEQ ID NO 23
<211> LENGTH: 59
<212> TYPE: PRT
<213> ORGANISM: Homo sapiens

<400> SEQUENCE: 23

Arg Leu Ser Cys Ala Ala Ser Gly Phe Thr Leu Asp Tyr Tyr Ala Ile
1               5                   10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Ala Asp Ser Val Lys Gly
        35                  40                  45

Arg Phe Thr Ile Ser Arg Asp Asn Ala Lys Asn
    50                  55

<210> SEQ ID NO 24
<211> LENGTH: 59
<212> TYPE: PRT
<213> ORGANISM: Homo sapiens

<400> SEQUENCE: 24

Arg Leu Ser Cys Ala Ala Ser Gly Phe Thr Leu Asp Tyr Tyr Val Ile
1               5                   10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Ala Asp Ser Val Lys Gly
        35                  40                  45

Arg Phe Thr Ile Ser Arg Asp Asn Ala Lys Asn
    50                  55

<210> SEQ ID NO 25
<211> LENGTH: 59
<212> TYPE: PRT
<213> ORGANISM: Homo sapiens

<400> SEQUENCE: 25

Arg Leu Ser Cys Ala Ala Ser Gly Phe Thr Leu Asp Tyr Tyr Ala Ile
1               5                   10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Gly Asp Ser Val Lys Gly
        35                  40                  45

Arg Phe Thr Ile Ser Arg Asp Lys Ala Lys Asn
    50                  55

<210> SEQ ID NO 26
<211> LENGTH: 58
<212> TYPE: PRT
<213> ORGANISM: Homo sapiens

<400> SEQUENCE: 26

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
            35                  40                  45

Phe Thr Ile Ser Arg Asp Asn Ala Lys Asn
    50                  55

<210> SEQ ID NO 27
<211> LENGTH: 58
<212> TYPE: PRT
<213> ORGANISM: Homo sapiens

<400> SEQUENCE: 27

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Lys Tyr Ala Asp Ser Val Lys Gly Arg
            35                  40                  45

Phe Thr Ile Ser Arg Asp Asn Ala Lys Asn
    50                  55

<210> SEQ ID NO 28
<211> LENGTH: 58
<212> TYPE: PRT
<213> ORGANISM: Homo sapiens

<400> SEQUENCE: 28

Arg Leu Ser Cys Ala Ala Ser Gly Ser Ile Phe Ser Ile Asn Val Met
1               5                   10                  15

Gly Trp Tyr Arg Gln Pro Pro Gly Lys Gln Arg Glu Leu Val Ala Gly
            20                  25                  30

Val Thr Ser Gly Gly Ser Thr Ser Tyr Ala Asp Ser Val Lys Gly Arg
            35                  40                  45

Phe Thr Ile Ser Arg Asp Asn Ala Lys Asn
    50                  55

<210> SEQ ID NO 29
<211> LENGTH: 58
<212> TYPE: PRT
<213> ORGANISM: Homo sapiens

<400> SEQUENCE: 29

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Pro
            20                  25                  30

Ile Thr Ser Gly Gly Ser Thr Asn Tyr Ala Asp Ser Val Lys Gly Arg
            35                  40                  45

Phe Thr Ile Ser Arg Asp Asn Ala Lys Asn
    50                  55

<210> SEQ ID NO 30
<211> LENGTH: 78
<212> TYPE: PRT
<213> ORGANISM: Homo sapiens

<400> SEQUENCE: 30

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

```
Ile Thr Ser Gly Gly Ser Thr Asn Tyr Ala Asp Ser Val Lys Gly Arg
            35                  40                  45

Phe Thr Ile Ser Arg Asp Asn Ala Lys Asn Thr Val Tyr Leu Gln Met
        50                  55                  60

Asn Ser Leu Lys Pro Glu Asp Thr Ala Val Tyr Tyr Cys Asn
 65                  70                  75

<210> SEQ ID NO 31
<211> LENGTH: 105
<212> TYPE: PRT
<213> ORGANISM: Homo sapiens

<400> SEQUENCE: 31

Arg Leu Ser Cys Ala Ala Ser Gly Ser Ile Phe Ser Ile Asn Ala Met
 1               5                  10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
            35                  40                  45

Phe Thr Ile Ser Arg Asp Asn Ala Lys Asn Thr Val Tyr Leu Gln Met
        50                  55                  60

Asn Ser Leu Lys Pro Glu Asp Thr Ala Val Tyr Tyr Cys Asn Ala Glu
 65                  70                  75                  80

Arg Ala Gly Asp Pro Phe Asp Tyr Trp Gly Gln Gly Thr Leu Val Thr
                85                  90                  95

Val Ser Ser Glu Arg Lys Cys Cys Val
                100                 105

<210> SEQ ID NO 32
<211> LENGTH: 108
<212> TYPE: PRT
<213> ORGANISM: Homo sapiens

<400> SEQUENCE: 32

Arg Leu Ser Cys Ala Ala Ser Gly Ser Ile Phe Ser Ile Asn Ala Met
 1               5                  10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
            35                  40                  45

Phe Thr Ile Ser Arg Asp Asn Ala Lys Asn Thr Val Tyr Leu Gln Met
        50                  55                  60

Asn Ser Leu Lys Pro Glu Asp Thr Ala Val Tyr Tyr Cys Gly Val Leu
 65                  70                  75                  80

Trp Phe Gly Glu Leu Ser Asp Trp Phe Asp Tyr Trp Gly Gln Gly Thr
                85                  90                  95

Leu Val Thr Val Ser Ser Glu Arg Lys Cys Cys Val
                100                 105

<210> SEQ ID NO 33
<211> LENGTH: 108
<212> TYPE: PRT
<213> ORGANISM: Homo sapiens
```

```
<400> SEQUENCE: 33

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Asp
65                  70                  75                  80

Cys Trp Gly Ser Arg Trp Tyr Phe Asp His Tyr Trp Gly Arg Gly Thr
                85                  90                  95

Leu Val Thr Val Ser Ser Glu Arg Lys Cys Cys Val
            100                 105

<210> SEQ ID NO 34
<211> LENGTH: 111
<212> TYPE: PRT
<213> ORGANISM: Homo sapiens

<400> SEQUENCE: 34

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Asp
65                  70                  75                  80

Thr Ser Pro Pro Arg Tyr Phe Asp Trp Leu Pro Phe Asp Tyr Trp Gly
                85                  90                  95

Gln Gly Thr Leu Val Thr Val Ser Ser Glu Arg Lys Cys Cys Val
            100                 105                 110

<210> SEQ ID NO 35
<211> LENGTH: 112
<212> TYPE: PRT
<213> ORGANISM: Homo sapiens

<400> SEQUENCE: 35

Arg Leu Ser Cys Ala Ala Ser Gly Ser Ile Phe Ser Ser Asn Ala Met
1               5                   10                  15

Gly Trp Ser Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val His Leu Gln Met
    50                  55                  60

Asn Ser Leu Lys Pro Glu Asp Thr Ala Val Tyr Tyr Cys Asn Ala Gly
65                  70                  75                  80
```

```
-continued

Asn Thr Met Val Arg Gly Val Ile Ile Lys Tyr Arg Phe Asp Tyr Trp
                85                  90                  95
Gly Gln Gly Thr Leu Val Thr Val Ser Ser Glu Arg Lys Cys Cys Val
            100                 105                 110
```